US010879470B2

(12) United States Patent
Kim et al.

(10) Patent No.: US 10,879,470 B2
(45) Date of Patent: Dec. 29, 2020

(54) CONDENSED CYCLIC COMPOUND AND ORGANIC LIGHT-EMITTING DEVICE INCLUDING THE SAME

(71) Applicant: Samsung Display Co., Ltd., Yongin-si (KR)

(72) Inventors: Seulong Kim, Yongin-si (KR); Illsoo Park, Yongin-si (KR); Hyosup Shin, Yongin-si (KR); Sunghun Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 142 days.

(21) Appl. No.: 15/375,015

(22) Filed: Dec. 9, 2016

(65) Prior Publication Data
US 2017/0170401 A1 Jun. 15, 2017

(30) Foreign Application Priority Data

Dec. 11, 2015 (KR) .................. 10-2015-0177362

(51) Int. Cl.
*H01L 51/00* (2006.01)
*C07C 13/72* (2006.01)
(Continued)

(52) U.S. Cl.
CPC .......... *H01L 51/0056* (2013.01); *C07C 13/72* (2013.01); *C09K 11/025* (2013.01);
(Continued)

(58) Field of Classification Search
CPC ......... H01L 51/003–0095; H01L 51/50–5296; H01L 2251/50–558; H01L 51/0052;
(Continued)

(56) References Cited

U.S. PATENT DOCUMENTS 7,701,131 B2   4/2010   Gerhard et al.
9,517,977 B2   12/2016  Spreitzer et al.
(Continued)

FOREIGN PATENT DOCUMENTS

CN     100469204 C    3/2009
CN     104795504 A    7/2015
(Continued)

OTHER PUBLICATIONS

Baranoff et al., Dalton Trans., 2015, 44, 8318-8329.*
(Continued)

*Primary Examiner* — Dylan C Kershner
*Assistant Examiner* — Elizabeth M. Dahlburg
(74) *Attorney, Agent, or Firm* — Lewis Roca Rothgerber Christie LLP

(57) ABSTRACT

Provided are condensed cyclic compounds represented by Formula 1:

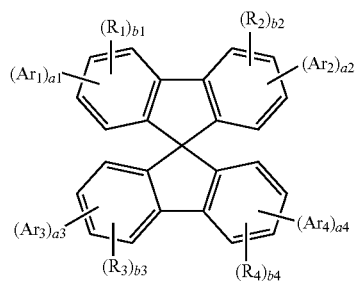

and an organic light-emitting device having the compounds which has decreased driving voltage, higher efficiency, and increased overall lifespan.

17 Claims, 4 Drawing Sheets

(51) Int. Cl.
*H01L 51/50* (2006.01)
*C09K 11/02* (2006.01)
*C09K 11/06* (2006.01)
*H01L 51/52* (2006.01)

(52) U.S. Cl.
CPC ............ C09K 11/06 (2013.01); H01L 51/005 (2013.01); H01L 51/5004 (2013.01); *C07C 2603/94* (2017.05); *C07C 2603/97* (2017.05); *C09K 2211/1007* (2013.01); *C09K 2211/1011* (2013.01); *C09K 2211/1029* (2013.01); *C09K 2211/185* (2013.01); *H01L 51/0085* (2013.01); *H01L 51/5016* (2013.01); *H01L 51/5262* (2013.01); *H01L 51/5278* (2013.01); *H01L 2251/552* (2013.01)

(58) Field of Classification Search
CPC ............... H01L 51/0056; H01L 51/005; H01L 51/0085; H01L 51/5004; H01L 51/5016; H01L 51/5262; H01L 51/5278; H01L 51/5048; H01L 51/5056; H01L 51/506; H01L 51/564; H01L 51/5088; H01L 51/5096; C09K 11/06; C09K 2211/00–188; C07C 2603/18; C07C 2603/94; C07C 2603/97; C07C 13/72
USPC ................... 428/690, 691, 917; 427/58, 66; 313/498–512; 257/40, 88–103, 257/E51.001–E51.052; 252/301.16–301.35
See application file for complete search history.

(56) References Cited

U.S. PATENT DOCUMENTS

| | | | |
|---|---|---|---|
| 9,543,538 B2 | 1/2017 | Kim et al. | |
| 10,227,528 B2 | 3/2019 | Jatsch et al. | |
| 2003/0044642 A1* | 3/2003 | Lee | C08G 61/10 428/690 |
| 2006/0088728 A1* | 4/2006 | Kwong | C07D 209/82 428/690 |
| 2006/0159951 A1* | 7/2006 | Falcou | C07C 13/567 428/690 |
| 2007/0087220 A1* | 4/2007 | Alvarado | H01L 51/5012 428/690 |
| 2009/0015144 A1* | 1/2009 | Takashima | C07C 13/62 313/504 |
| 2009/0167161 A1 | 7/2009 | Yabunouchi et al. | |
| 2010/0001636 A1* | 1/2010 | Yabunouchi | C07D 307/91 313/504 |
| 2010/0096622 A1* | 4/2010 | Iizumi | H01L 51/5012 257/40 |
| 2011/0121274 A1 | 5/2011 | Parham et al. | |
| 2012/0126179 A1* | 5/2012 | Parham | C07C 13/72 252/500 |
| 2012/0146014 A1* | 6/2012 | Kato | C07D 209/86 257/40 |
| 2013/0207046 A1 | 8/2013 | Pflumm et al. | |
| 2015/0243897 A1 | 8/2015 | Montenegro et al. | |
| 2017/0222172 A1* | 8/2017 | Watabe | H01L 51/5028 313/504 |

FOREIGN PATENT DOCUMENTS

| | | | |
|---|---|---|---|
| CN | 104903328 A | 9/2015 | |
| JP | 2002-356449 A | 12/2002 | |
| JP | 5833013 B2 | 11/2015 | |
| KR | 10-2010-0097180 A | 9/2010 | |
| KR | 10-2011-0052540 A | 5/2011 | |
| KR | 10-2013-0099098 A | 9/2013 | |
| KR | 10-2014-0145452 A | 12/2014 | |
| KR | 10-2015-0041652 A | 4/2015 | |
| WO | WO 2005011334 A1 * | 2/2005 | ........... C07C 13/567 |
| WO | WO 2013/017192 A1 | 7/2012 | |
| WO | WO 2014/109274 A1 | 7/2014 | |

OTHER PUBLICATIONS

"Substituent group", Cammack, R. Attwood, T. K. Campbell, P. N. Parish, J. H. Smith, A. D. Stirling, J. L. Vella, F. (2006). Oxford Dictionary of Biochemistry and Molecular Biology (2nd Edition). Oxford University Press, p. 639 (Year: 2006).*

Schmidbauer, S. et al., Chemical Degradation in Organic Light-Emitting Devices: Mechanisms and Implications for the Design of New Materials, Adv. Mater. 25(15):2114-2129, 2013.

Thiery, S., et al., 9,9'-Spirobifluorene and 4-Phenyl-9,9'-Spriobifluorene: Pure Hydrocarbon Small Molecules as Hosts for Efficient Green and Blue PhOLEDs, J. Mater. Chem. C, 2:4156-4166, 2014.

Theiry, S., et al., 2-Substituted vs 4-Substituted-9,9'-Spriobifluorene Host Materials for Green and Blue Phosphorescent OLEDs: a Structure-Property Relationship Study, Tetrahedron 70:6337-6351, 2014.

Chinese Intellectual Property Office Action for corresponding Chinese Patent Application No. 201611108231.X, dated Sep. 28, 2020, 14 pages.

Lee, Seung Eun, et al.; Novel Synthesis of Highly Phenyl-Substituted Spirobifluorene and Carbazole Derivatives Through Diels-Alder Reaction for Light-Emitting Diodes, Journal of Non-linear Optical Physics & Materials, vol. 14, No. 4, World Scientific, 2005, pp. 469-474.

Spehr, Till et al.; Highly efficient light emitters based on the spiro concept, Organic Electronics 4, Elsevier, 2003, pp. 61-69.

* cited by examiner

| 190 |
|---|
| 150 |
| 110 |

| 190 |
|-----|
| 150 |
| 110 |
| 210 |

| 220 |
|-----|
| 190 |
| 150 |
| 110 |

| 220 |
|---|
| 190 |
| 150 |
| 110 |
| 210 |

CONDENSED CYCLIC COMPOUND AND ORGANIC LIGHT-EMITTING DEVICE INCLUDING THE SAME

CROSS-REFERENCE TO RELATED APPLICATION

This application claims the benefit of Korean Patent Application No. 10-2015-0177362, filed on Dec. 11, 2015, in the Korean Intellectual Property Office, the disclosure of which is incorporated herein in its entirety by reference.

BACKGROUND

Field

One or more example embodiments relate to a condensed cyclic compound and an organic light-emitting device including the same.

Description of the Related Art

Organic light-emitting devices are self-emission devices that have wide viewing angles, high contrast ratios, short response times, and excellent brightness, driving voltage, and response speed characteristics, compared to conventional devices, and produce full-color images.

Organic light-emitting devices may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit from an excited state to a ground state, thereby generating light.

SUMMARY

One or more example embodiments include a condensed cyclic compound and an organic light-emitting device including the same.

Additional aspects will be set forth in part in the description which follows and, in part, will be apparent from the description, or may be learned by practice of the presented embodiments.

According to one or more example embodiments, a condensed cyclic compound is represented by Formula 1:

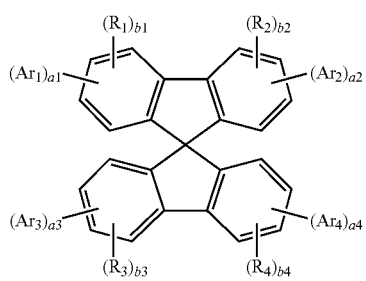

<Formula 1>

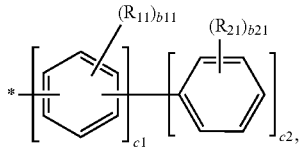

<Formula 2> wherein, in Formulae 1 and 2, $Ar_1$ to $Ar_4$ are each independently a group represented by Formula 2, $R_1$ to $R_4$, $R_{11}$, and $R_{21}$ are each independently selected from hydrogen, deuterium, a $C_1$-$C_{60}$ alkyl group, a $C_1$-$C_{60}$ alkoxy group, and a phenyl group; and a $C_1$-$C_{60}$ alkyl group, a $C_1$-$C_{60}$ alkoxy group, and a phenyl group, each substituted with at least one deuterium, a1 to a4, b1 to b4, b11, and b21 are each independently an integer of 0 to 4, c1 and c2 are each independently an integer of 1 to 5, and the sum of a1, a2, a3, and a4 is 1 or more.

According to one or more example embodiments, an organic light-emitting device includes: a first electrode; a second electrode facing the first electrode; and an organic layer between the first electrode and the second electrode, the organic layer comprising an emission layer, wherein the organic layer comprises one or more of the condensed cyclic compounds provided herein.

BRIEF DESCRIPTION OF THE DRAWINGS

These and/or other aspects will become apparent and more readily appreciated from the following description of the example embodiments, taken in conjunction with the accompanying drawings in which:

FIG. 1 is a schematic view of an organic light-emitting device according to an embodiment;

FIG. 2 is a schematic view of an organic light-emitting device according to an embodiment;

FIG. 3 is a schematic view of an organic light-emitting device according to an embodiment; and FIG. 4 is a schematic view of an organic light-emitting device according to an embodiment.

DETAILED DESCRIPTION

Reference will now be made in detail to example embodiments, examples of which are illustrated in the accompanying drawings, wherein like reference numerals refer to like elements throughout. In this regard, the present example embodiments may have different forms and should not be construed as being limited to the descriptions set forth herein. Accordingly, the example embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

A condensed cyclic compound in one embodiment may be represented by Formula 1:

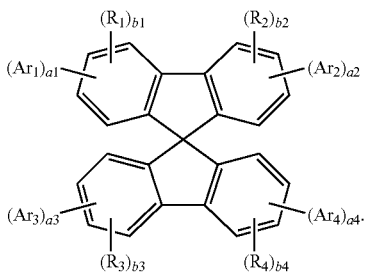

<Formula 1>

$Ar_1$ to $Ar_4$ in Formula 1 may each independently be a group represented by Formula 2:

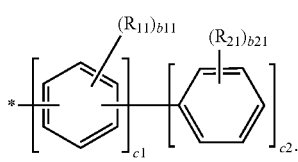

<Formula 2>

$R_1$ to $R_4$, $R_{11}$, and $R_{21}$ in Formulae 1 and 2 may each independently be selected from:

hydrogen, deuterium, a $C_1$-$C_{60}$ alkyl group, a $C_1$-$C_{60}$ alkoxy group, and a phenyl group; and a $C_1$-$C_{60}$ alkyl group, a $C_1$-$C_{60}$ alkoxy group, and a phenyl group, each substituted with at least one deuterium.

For example, $R_1$ to $R_4$, $R_{11}$, and $R_{21}$ in Formulae 1 and 2, may each independently be selected from:

hydrogen, deuterium, and a phenyl group; and a phenyl group substituted with at least one deuterium, but are not limited thereto.

In one embodiment, in Formulae 1 and 2, $R_1$ to $R_4$, $R_{11}$, and $R_{21}$ may be each independently selected from:

hydrogen, —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an isobutyl group, a sec-butyl group, a tert-butyl group, an n-pentyl group, an isopentyl group, a sec-pentyl group, a tert-pentyl group, a methoxy group, an ethoxy group, a propoxy group, butoxy group, a pentoxy group, and a phenyl group; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a methoxy group, an ethoxy group, a propoxy group, butoxy group, a pentoxy group, and a phenyl group, each substituted with at least one deuterium.

In some embodiments, in Formulae 1 and 2, $R_1$ to $R_4$, $R_{11}$, and $R_{21}$ may each independently be selected from hydrogen, deuterium, and a phenyl group.

a1 to a4, b1 to b4, b11, and b21 in Formulae 1 and 2, may each independently be an integer selected of 0 to 4.

a1 to a4 in Formula 1 may represent the number of $Ar_1$ to $Ar_4$, respectively. When a1 is two or more, two or more $Ar_1(s)$ may be identical to or different from each other, when a2 is two or more, two or more $Ar_2(s)$ may be identical to or different from each other, when a3 is two or more, two or more $Ar_3(s)$ may be identical to or different from each other, and when a4 is two or more, two or more $Ar_4(s)$ may be identical to or different from each other.

In Formulae 1 and 2, b1 to b4, b11, and b21 may represent the number of $R_1$ to $R_4$, $R_{11}$, and $R_{21}$, respectively. When b1 is two or more, two or more $R_1(s)$ may be identical to or different from each other, when b2 is two or more, two or more $R_2(s)$ may be identical to or different from each other, when b3 is two or more, two or more $R_3(s)$ may be identical to or different from each other, when b4 is two or more, two or more $R_4(s)$ may be identical to or different from each other, when b11 is two or more, two or more $R_{11}(s)$ may be identical to or different from each other, and when b21 is two or more, two or more $R_{21}(s)$ may be identical to or different from each other.

In Formula 2, c1 and c2 may each independently be an integer selected of 1 to 5. Since the minimum values of c1 and c2 may be 1, respectively, Formula 2 may include at least two substituted or unsubstituted benzene rings.

For example, c1 and c2 in Formula 2 may each independently be 1, 2, or 3.

In Formula 1, the sum of a1, a2, a3, and a4 may be 1 or more. Thus, Formula 1 may essentially include at least one group represented by Formula 2.

In one embodiment, in Formula 1, the sum of a1, a2, a3, and a4 may be 1, 2, or 3.

In some embodiments, in Formula 1, the sum of a1, a2, a3, and a4 may be 1.

In some embodiments, in Formula 1, a1 may be equal to 1, and a2, a3, and a4 may be equal to 0 at the same time;

both a1 and a2 may be equal to 1, and both a3 and a4 may be equal to 0;

both a1 and a3 may be equal to 1, and both a2 and a4 may be equal to 0;

a1, a2, and a3 may be equal to 1 at the same time, and a4 may be equal to 0; or a1, a2, a3, and a4 may be equal to 1 at the same time, but may not be limited thereto.

In one embodiment, $Ar_1$ to $Ar_4$ in Formula 1 may each independently be selected from groups represented by Formulae 2-1 to 2-40:

Formula 2-1

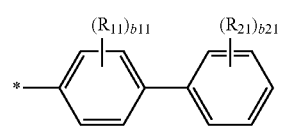

Formula 2-2

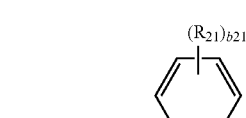

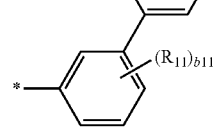

-continued

Formula 2-3

Formula 2-4

Formula 2-5

Formula 2-6

Formula 2-7

Formula 2-8

Formula 2-9

Formula 2-10

Formula 2-11

Formula 2-12

Formula 2-13

-continued
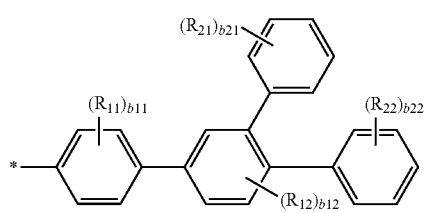
Formula 2-14
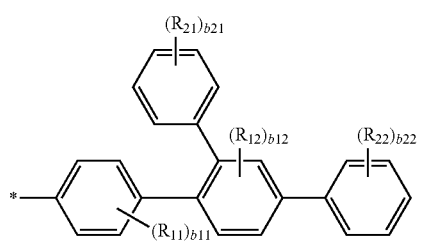
Formula 2-15
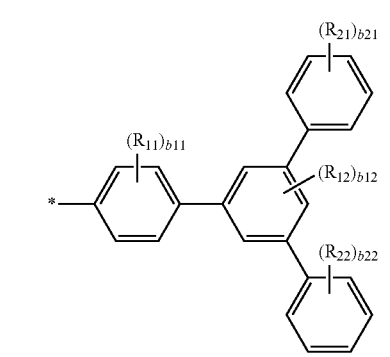
Formula 2-16
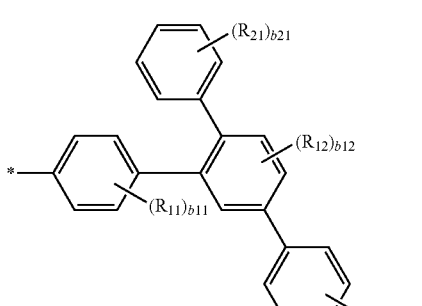
Formula 2-17
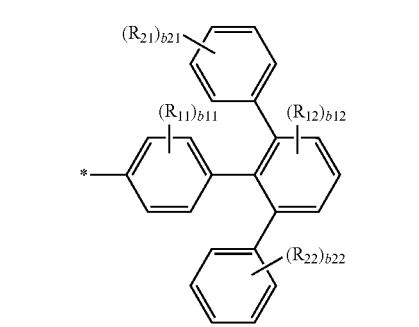
Formula 2-18
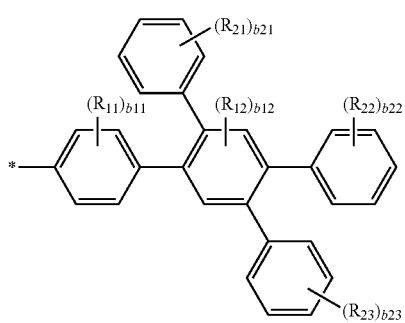
Formula 2-19
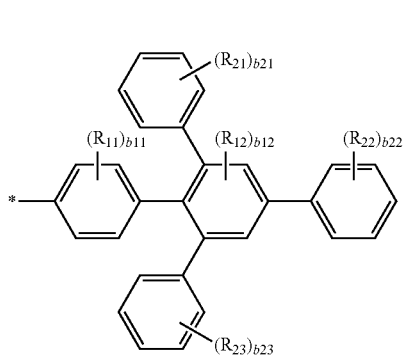
Formula 2-20
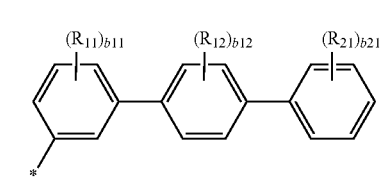
Formula 2-21
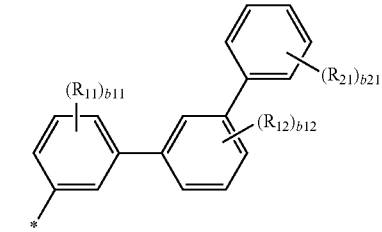
Formula 2-22
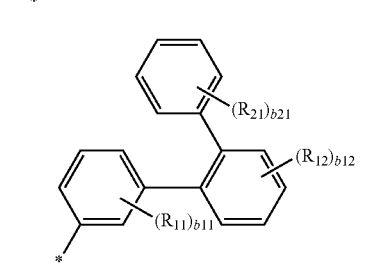
Formula 2-23
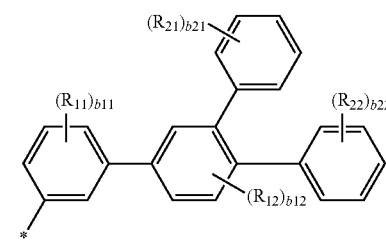
Formula 2-24

-continued

Formula 2-25

Formula 2-26

Formula 2-27

Formula 2-28

Formula 2-29

Formula 2-30

Formula 2-31

Formula 2-32

Formula 2-33

Formula 2-34

Formula 2-35

-continued

Formula 2-36
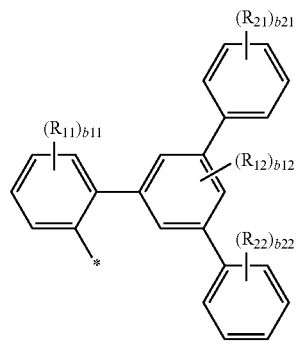

Formula 2-37
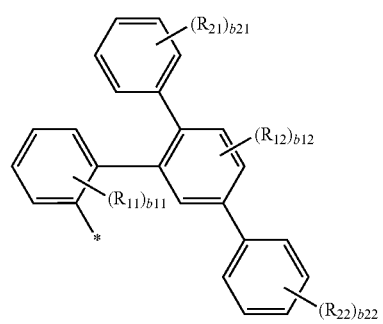

Formula 2-38
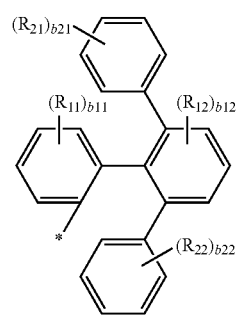

Formula 2-39
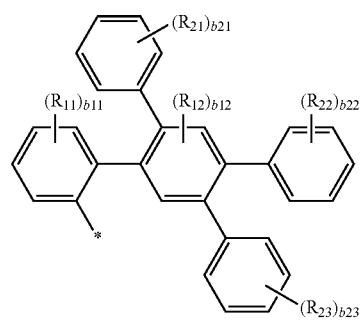

Formula 2-40
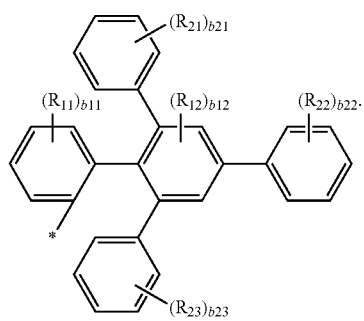

In Formulae 2-1 to 2-40, $R_{11}$ and $R_{21}$ may be the same as described above, $R_{12}$ may be the same as described above in connection with $R_{11}$, $R_{22}$ and $R_{23}$ may be the same as described above in connection with $R_{21}$, b11, b12, and b21 to b23 may each independently be 0, 1, or 2, and

* may represent a binding site to a neighboring atom.

For example, $R_{11}$, $R_{12}$, and $R_{21}$ to $R_{23}$ in Formulae 2-1 to 2-40 may each independently be hydrogen, deuterium, or a phenyl group.

In some embodiments, in Formula 1, $Ar_1$ to $Ar_4$ may each independently be selected from groups represented by Formulae 2-(1) to 2-(54):

Formula 2(1)
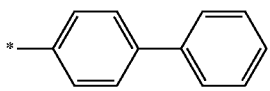

Formula 2(2)
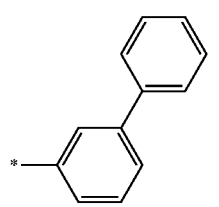

Formula 2(3)
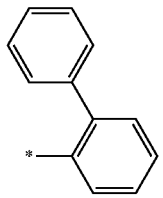

Formula 2(4)
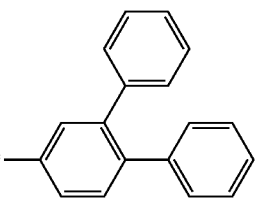

Formula 2(5)
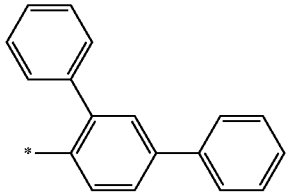

Formula 2(6)
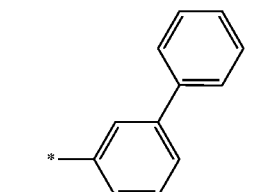

-continued
Formula 2(7)
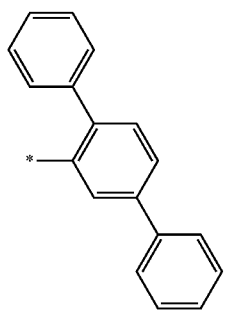
Formula 2(8)
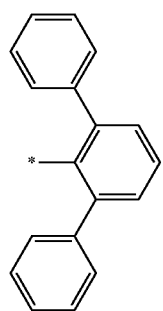
Formula 2(9)
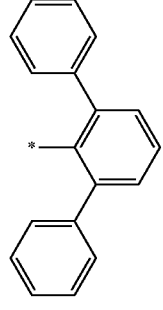
Formula 2(10)
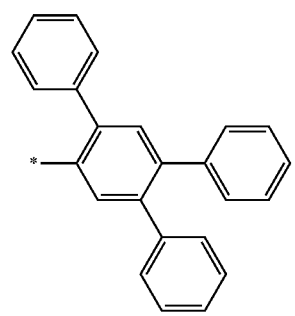
Formula 2(11)
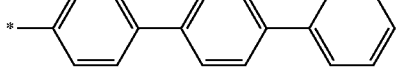
Formula 2(12)
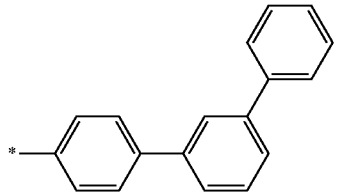
Formula 2(13)
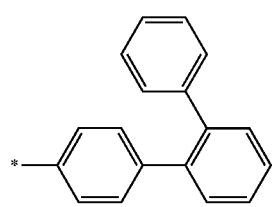
Formula 2(14)
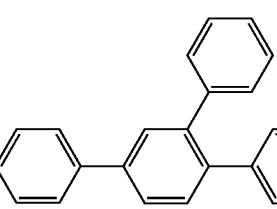
Formula 2(15)
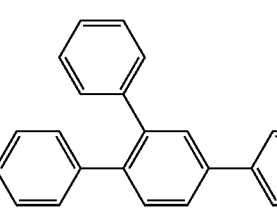
Formula 2(16)
Formula 2(17)
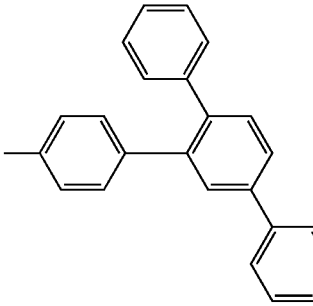
Formula 2(18)
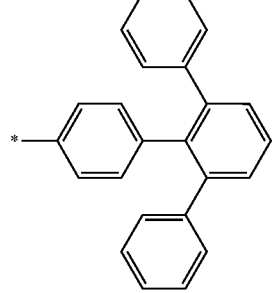

Formula 2(19)
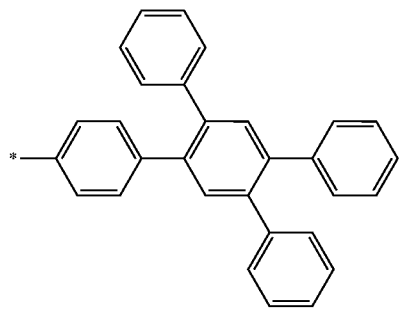
Formula 2(20)
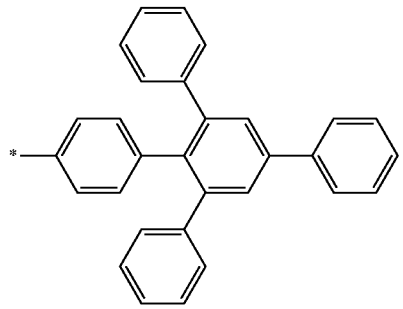
Formula 2(21)
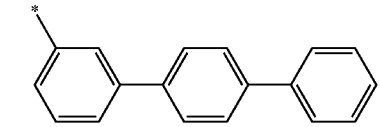
Formula 2(22)
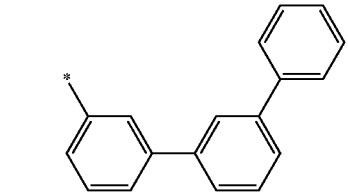
Formula 2(23)
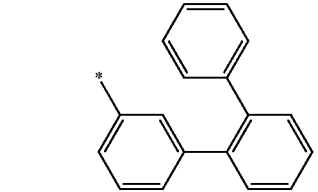
Formula 2(24)
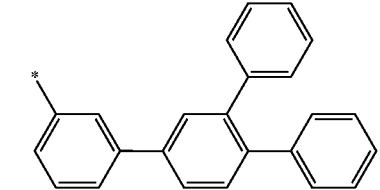
Formula 2(25)
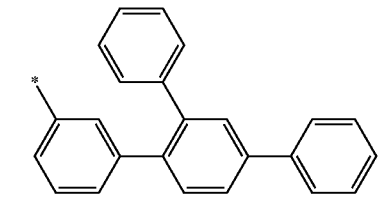
Formula 2(26)
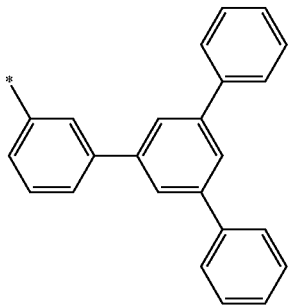
Formula 2(27)
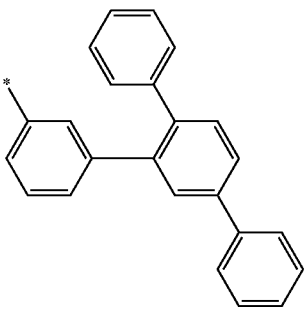
Formula 2(28)
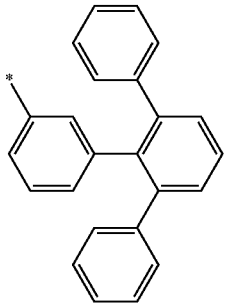
Formula 2(29)
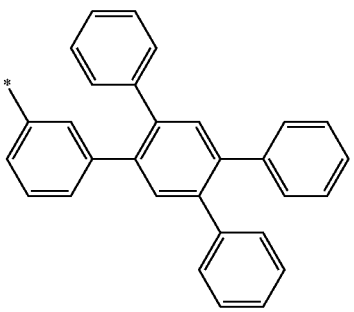
Formula 2(30)
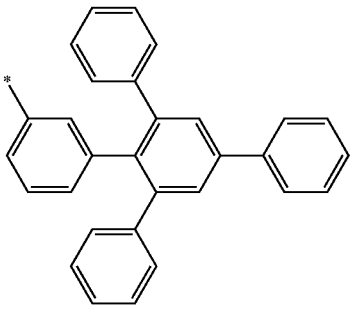

Formula 2(31)
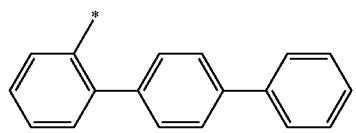
Formula 2(32)
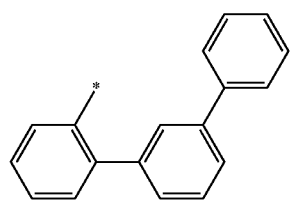
Formula 2(33)
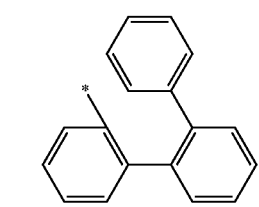
Formula 2(34)
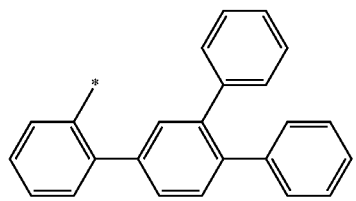
Formula 2(35)
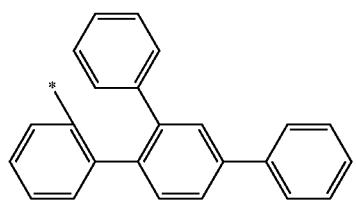
Formula 2(36)
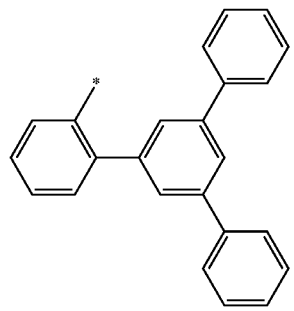
Formula 2(37)
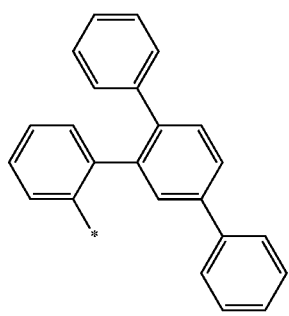
Formula 2(38)
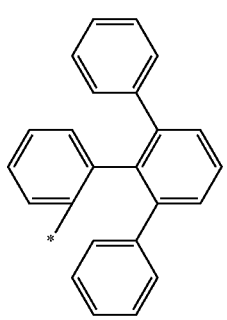
Formula 2(39)
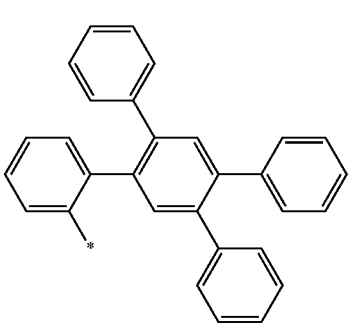
Formula 2(40)
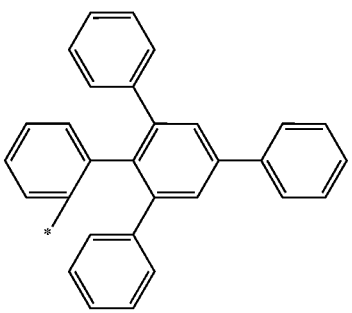
Formula 2(41)
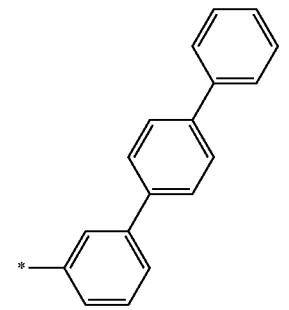

Formula 2(42)
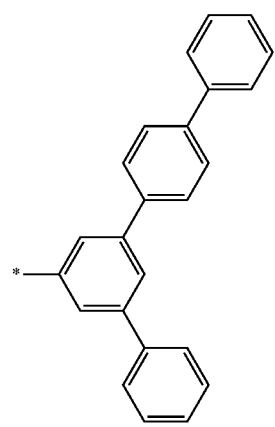
Formula 2(45)
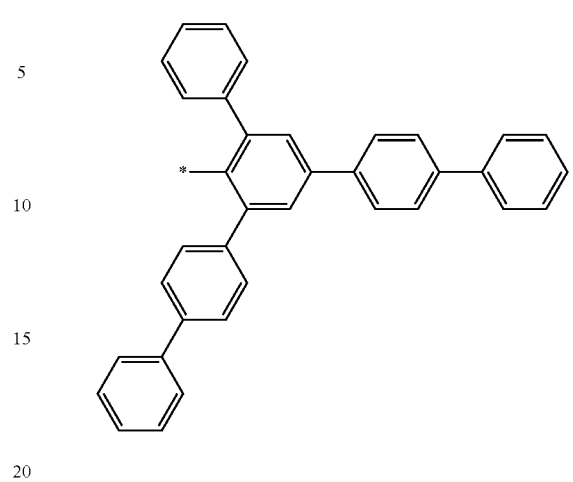
Formula 2(43)
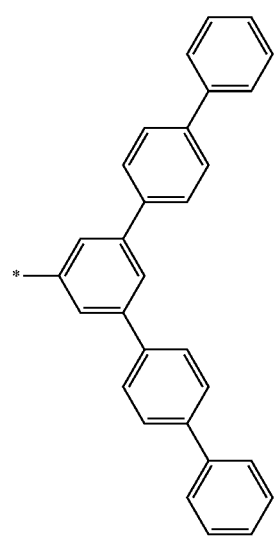
Formula 2(46)
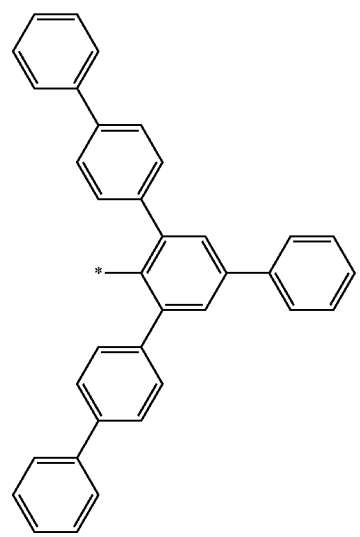
Formula 2(44)
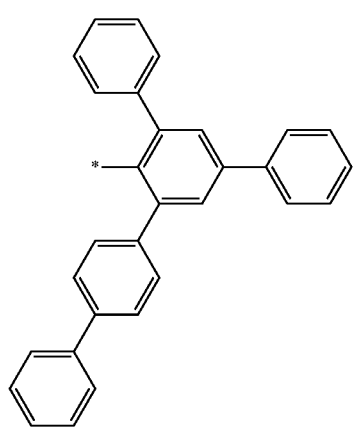
Formula 2(47)
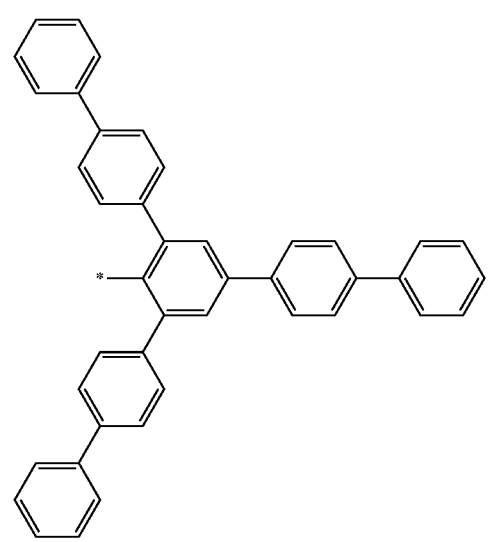

Formula 2(48)
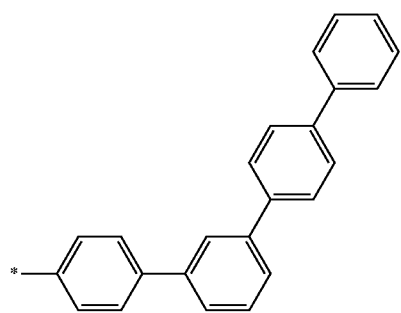
Formula 2(49)
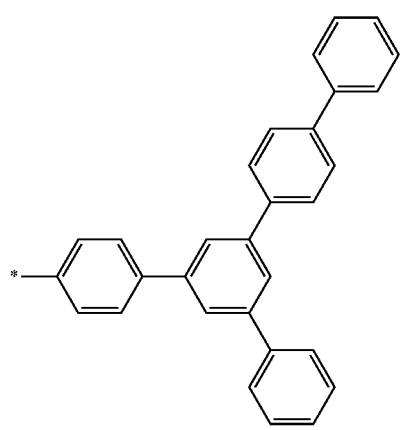
Formula 2(50)
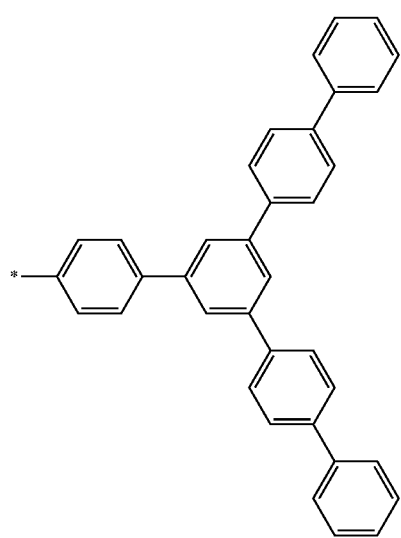
Formula 2(51)
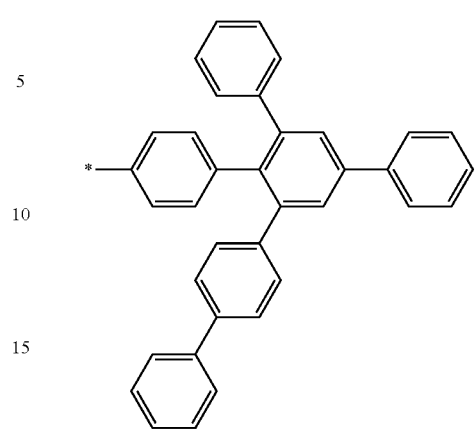
Formula 2(52)
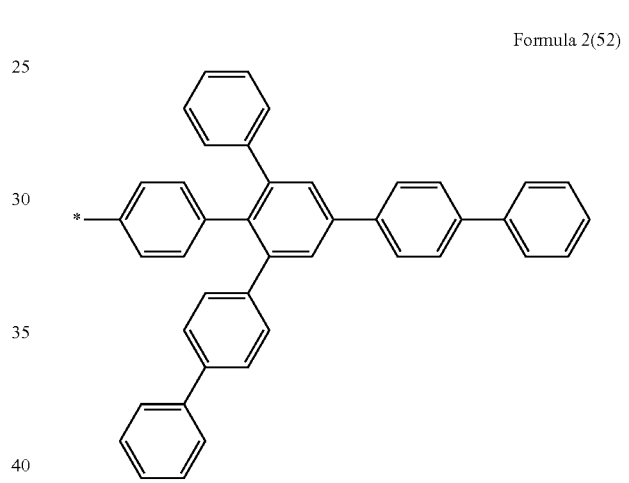
Formula 2(53)
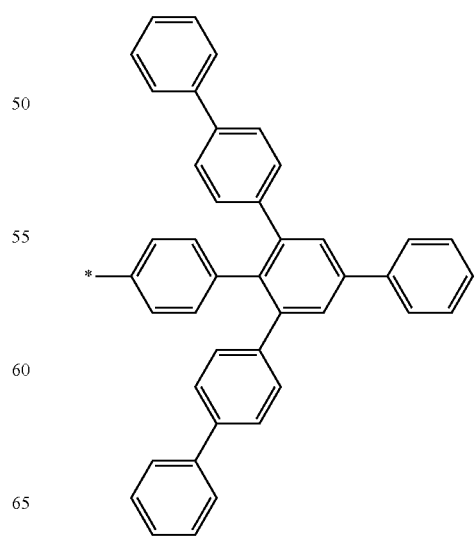

-continued
Formula 2(54)
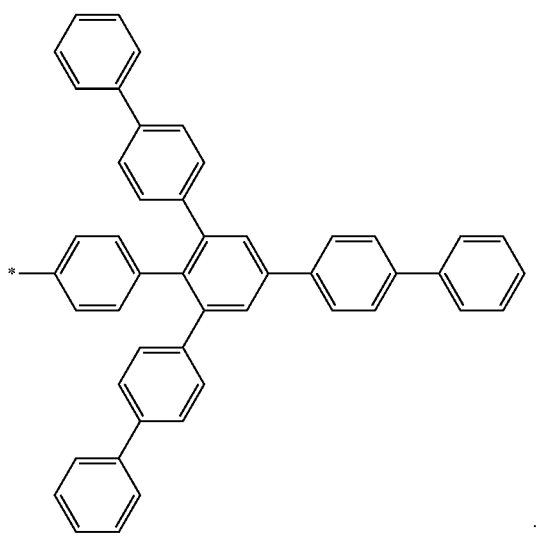
In Formulae 2(1) to 2(54), * may represent a binding site to a neighboring atom.
In some embodiments, a condensed cyclic compound may be represented by one of Formulae 1-1 to 1-11:
Formula 1-1
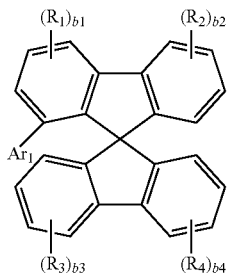
Formula 1-2
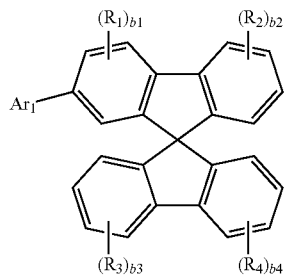
Formula 1-3
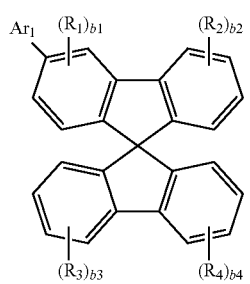
Formula 1-4
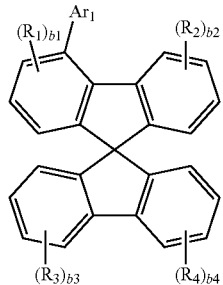
Formula 1-5
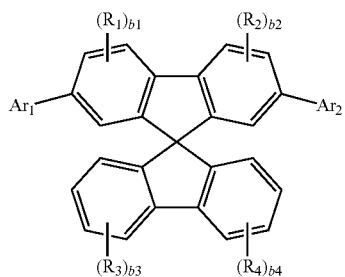
Formula 1-6
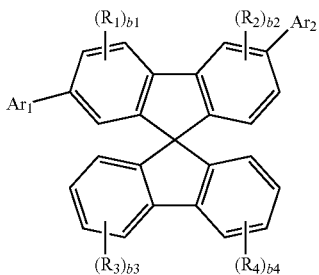
Formula 1-7
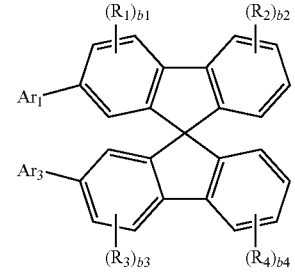
Formula 1-8
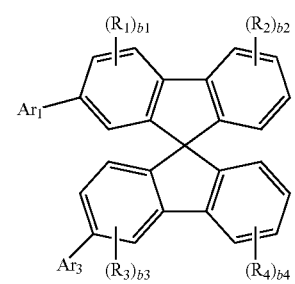

Formula 1-9

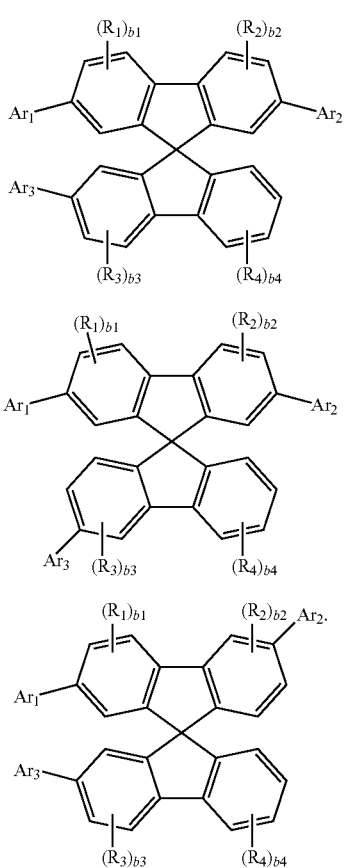

Formula 1-10

Formula 1-11

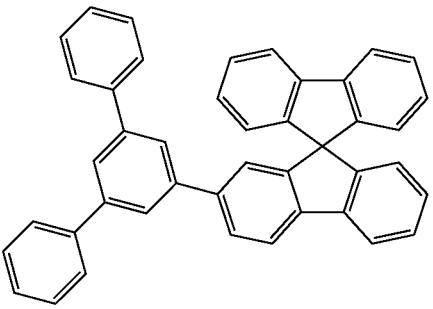
1

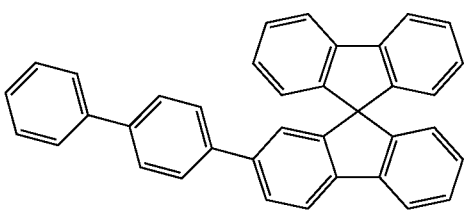
2

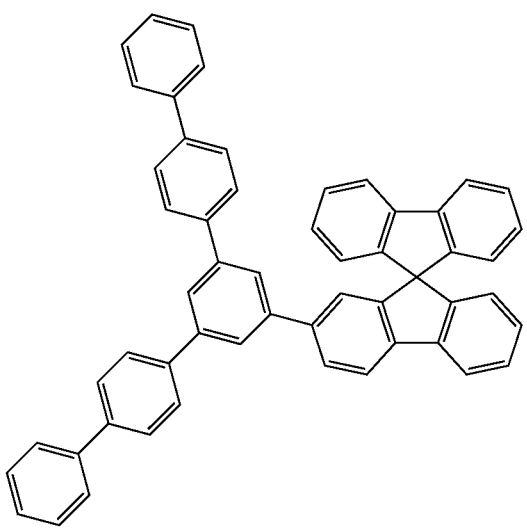
3

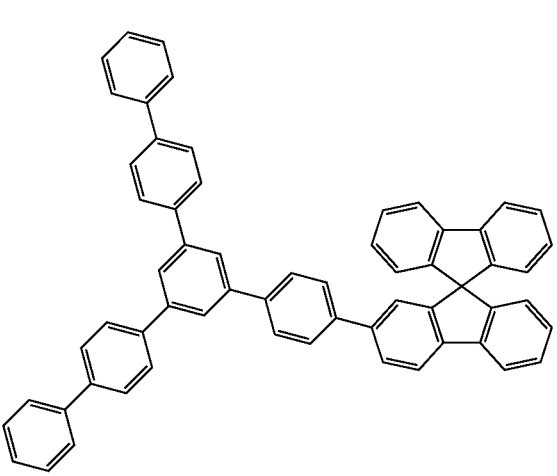
4

$Ar_1$ to $Ar_3$, $R_1$ to $R_4$, and b1 to b4 in Formulae 1-1 to 1-11 are the same as described above.

For example, $Ar_1$ to $Ar_3$ in Formulae 1-1 to 1-11 may each independently be selected from groups represented by Formulae 2-1 to 2-40.

In some embodiments, $Ar_1$ to $Ar_3$ in Formulae 1-1 to 1-11 may each independently be selected from groups represented by Formulae 2(1) to 2(40).

The condensed cyclic compound may have a molecular weight from 450 to 1000. Accordingly, sublimation/refinement of the condensed cyclic compound may be effectively performed, and a thin film formed by using the condensed cyclic compound may have an excellent morphology.

The condensed cyclic compound may have a triplet ($T_1$) energy level from 2.7 eV to 3.0 eV, for example, the condensed cyclic compound may have a triplet ($T_1$) energy level from 2.7 eV to 2.95 eV, for example, 2.75 eV to 2.82 eV. The condensed cyclic compound may have a lowest unoccupied molecular orbital (LUMO) energy level (found value) less than −2.4 eV, for example, may have a LUMO energy level (found value) less than −2.4 eV and more than or equal to −3.0 eV. Accordingly, the condensed cyclic compound may have electric characteristics appropriate for being used as a material for an electronic device, for example a material for forming an emission layer of an organic light-emitting device. In one embodiment, the condensed cyclic compound having those triplet ($T_1$) energy level ranges may effectively transfer energy to a blue phosphorescent dopant that emits deep blue light.

The condensed cyclic compound may be one selected from Compounds 1 to 14.

5
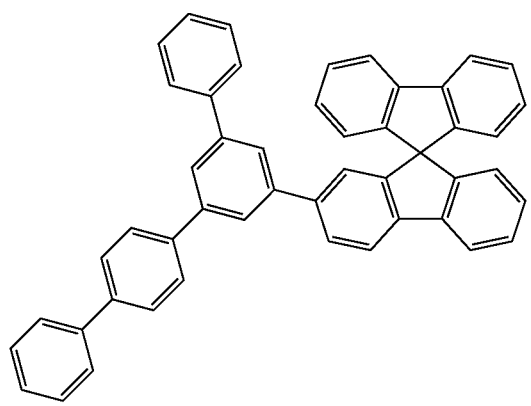
6
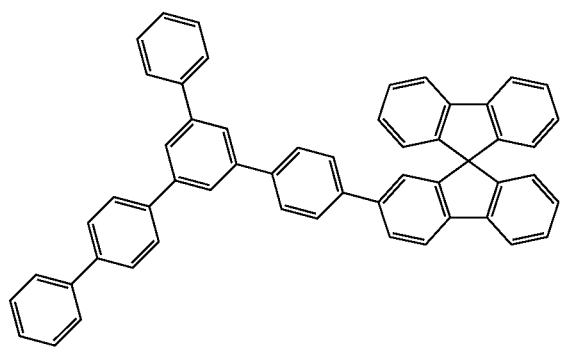
7
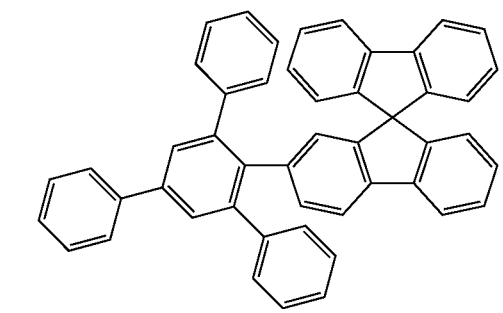
8
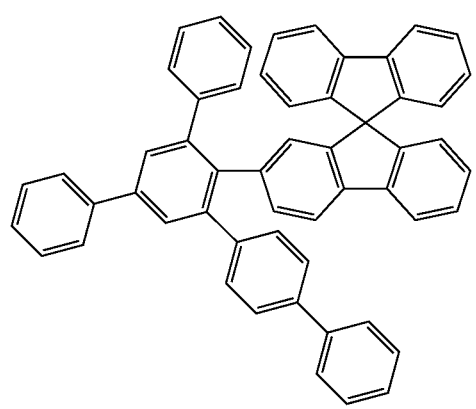
9
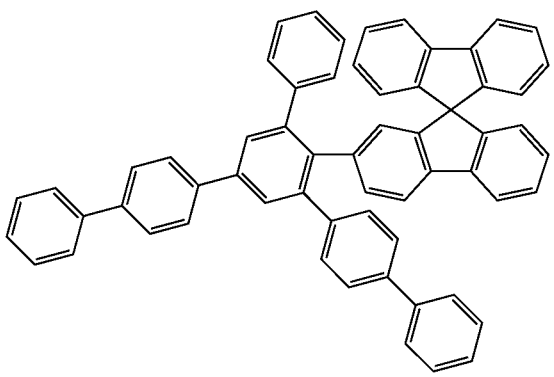
10
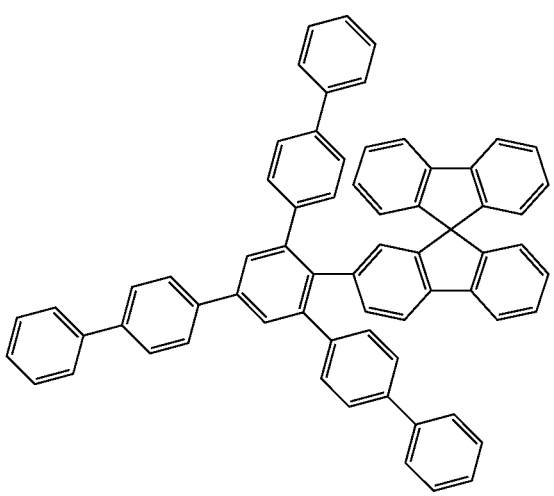
11
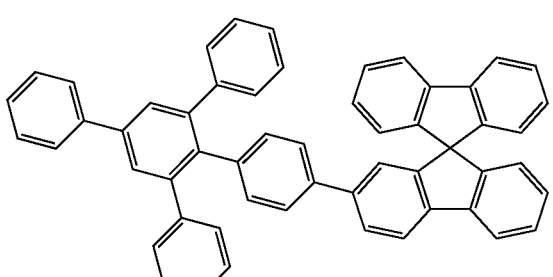
12
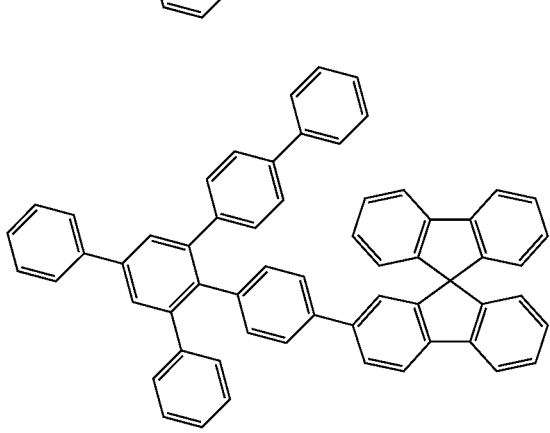

-continued

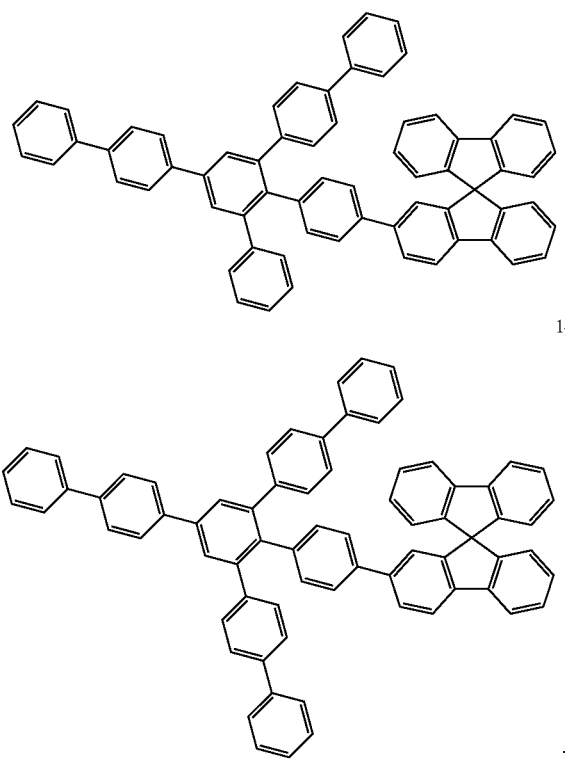

13

14

The condensed cyclic compound may have a spiro-bifluorene based core represented by Formula 1. Accordingly, the condensed cyclic compound may have a high decomposition resistance even when the condensed cyclic compound contacts charges, such as holes and electrons, and/or excitons. Accordingly, an electronic device employing the condensed cyclic compound, for example, an organic light-emitting device employing the condensed cyclic compound may have high efficiency and a long lifespan.

In addition, $Ar_1$ to $Ar_4$ in Formula 1 may be a group represented by Formula 2. Since the sum of a1 to a4 respectively representing the number of $Ar_1$ to $Ar_4$ is 1 or more, the condensed cyclic compound may essentially include at least one group represented by Formula 2. Here, since the minimum values of c1 and c2 in the group represented by Formula 2 may each be two or more, the group represented by Formula 2 may have two or more substituted or unsubstituted benzene rings. Accordingly, the condensed cyclic compound represented by Formula 1 may have a triplet energy level. Thus, without limitation to a particular theory, a triplet energy level difference between the condensed cyclic compound and a blue phosphorescent dopant may be relatively small (for example, less than 0.2 eV) in an electronic device (for example, an organic light-emitting device) that includes a thin film including the condensed cyclic compound and blue phosphorescent dopant, and thus the electronic device may have high efficiency and a long lifespan.

The condensed cyclic compound represented by Formula 1 may be synthesized by using a known organic synthetic method. A synthesis method of the condensed cyclic compound may be recognizable by one of ordinary skill in the art in view of the following embodiments.

At least one of the condensed cyclic compounds of Formula 1 may be used between a pair of electrodes of an organic light-emitting device. For example, the condensed cyclic compound may be included in an emission layer. In some embodiments, the condensed cyclic compound of Formula 1 may be used as a material for a capping layer located outside a pair of electrodes of an organic light-emitting device.

Accordingly, provided is an organic light-emitting device including: a first electrode; a second electrode facing the first electrode; and an organic layer between the first electrode and the second electrode, the organic layer including an emission layer, wherein the organic layer includes at least one condensed cyclic compound represented by Formula 1.

The expression that "(an organic layer) includes at least one of the condensed cyclic compounds" used herein includes a case in which "(an organic layer) includes identical condensed cyclic compounds represented by Formula 1 and a case in which (an organic layer) includes two or more different condensed cyclic compounds represented by Formula 1."

For example, the organic layer may include, as the condensed cyclic compound, only Compound 1. In this regard, Compound 1 may exist in an emission layer of the organic light-emitting device. In some embodiments, the organic layer may include, as the condensed cyclic compound, Compound 1 and Compound 2. In this regard, Compound 1 and Compound 2 may exist in an identical layer (for example, Compound 1 and Compound 2 may all exist in an emission layer), or different layers (for example, Compound 1 may exist in a hole transport layer and Compound 2 may exist in an emission layer).

The organic layer may include a hole transport region between a first electrode (anode) and an emission layer and an electron transport region between the emission layer and a second electrode (cathode). The hole transport region may include a hole injection layer, a hole transport layer, an emission auxiliary layer, an electron blocking layer, or any combination thereof, and the electron transport region may include a hole blocking layer, a buffer layer, an electron transport layer, an electron controlling layer, an electron injection layer, or any combination thereof.

In some embodiments, the emission layer of the organic light-emitting device may include the condensed cyclic compound. The emission layer may further include a dopant. The dopant may be a phosphorous dopant or a fluorescent dopant. For example, the dopant may be a blue phosphorescent dopant. The blue phosphorescent dopant may be a compound that emits blue light (for example, deep blue light) by a phosphorescent emission mechanism (for example, a dexter energy transfer mechanism) in which an x-coordinate and a y-coordinate of the blue light may each independently be from about 0.03 to about 0.3.

In some embodiments, the emission layer may include a host and a dopant, the host may include the condensed cyclic compound represented by Formula 1, and the dopant may include the blue phosphorescent dopant as described above.

The triplet energy level of the condensed cyclic compound included in the emission layer may be higher than the triplet energy level of the blue phosphorescent dopant, and a difference between the triplet energy level of the condensed cyclic compound and the triplet energy level of the blue phosphorescent dopant may be less than 0.2 eV (for example, more than or equal to 0.01 eV and less than or equal to 0.15 eV). In some embodiments, the triplet energy level of the condensed cyclic compound included in the emission layer may be higher than the triplet energy level of the blue phosphorescent dopant, and a difference between the triplet energy level of the condensed cyclic compound and the triplet energy level of the blue phosphorescent dopant may be more than or equal to 0.05 eV and less than or equal to 0.12 eV.

Accordingly, an energy transfer from the condensed cyclic compound (host) to the blue phosphorescent dopant may be effectively accomplished without decomposition/dissociation of the condensed cyclic compound and the blue phosphorescent dopant, the organic light-emitting device including the condensed cyclic compound and blue phosphorescent dopant may have high efficiency and a long lifespan.

For reference, a highest occupied molecular orbital (HOMO) energy level, a LUMO energy level, and a triplet ($T_1$) energy level of Compounds A to C have been evaluated by using a DFT method of the Gaussian program (structurally optimized at the level of B3LYP and 6-31G(d,p)) and thus the results are illustrated in Table 1.

TABLE 1

| | HOMO (eV) calculation value | LUMO (eV) calculation value | $T_1$ (eV) calculation value |
|---|---|---|---|
| Compound A | −5.51 | −1.10 | 2.79 |
| Compound B | −5.69 | −1.89 | 2.59 |
| Compound C | −4.81 | −0.89 | 2.63 |

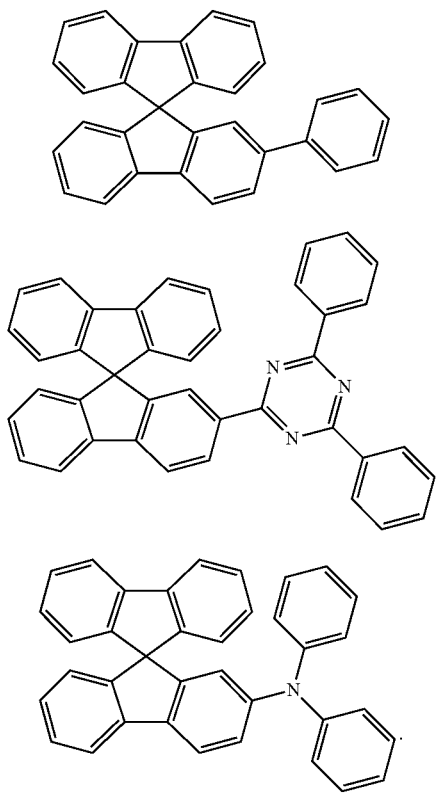

Without limitation to a particular theory, since in Compound A, only one phenyl group is bound to a spiro-bifluorene core, Compound A may have a relatively high LUMO energy level. An organic light-emitting device employing Compound A may not effectively achieve a charge movement balance during driving, to thus cause a lower efficiency. Since Compound B may have a relatively small $T_1$ energy, the $T_1$ energy of Compound B may be smaller than that of a conventional phosphorescent dopant. An organic light-emitting device employing Compound B may have reduced energy transfer efficiency in an emission layer, to thus cause a lower efficiency. In addition, Compound C may include a hole transporting group such as a diphenylamino group, to thus have a relatively low $T_1$ energy and a poor charge movement characteristic. Due to the inclusion of Compound C, a formed organic light-emitting device may have lower efficiency and a shorter lifetime.

In one embodiment, the triplet energy level of the blue phosphorescent dopant in the organic light-emitting device may be 2.7 eV or more and 2.9 eV or less, but is not limited thereto. When the blue phosphorescent dopant has the above-described triplet energy level range, and is used together with the condensed cyclic compound represented by Formula 1, a blue organic light-emitting device having high efficiency and a long lifespan may be implemented.

In some embodiments, a hole transport region of the organic light-emitting device may include the emission auxiliary layer, in which the condensed cyclic compound may be included in the emission auxiliary layer. The emission auxiliary layer may directly contact the emission layer, and may not include a dopant included in the emission layer.

In some embodiments, a hole transport region of the organic light-emitting device may include the emission auxiliary layer, in which the condensed cyclic compound may be included in the emission layer and the emission auxiliary layer. The condensed cyclic compound included in the emission layer may be the same as the condensed cyclic compound included in the emission auxiliary layer, and the emission layer may further include a blue phosphorescent dopant.

The emission auxiliary layer may prevent charges (for example, electrons) and/or excitons from moving from the emission layer to the hole transport region, and may promote holes to be transferred from the hole transport region to the emission layer. Accordingly, an organic light-emitting device including the emission auxiliary layer may have high efficiency and a long lifespan.

The term "organic layer" as used herein, refers to a single layer and/or a plurality of layers between the first electrode and the second electrode of an organic light-emitting device. A material included in the "organic layer" is not limited to an organic material.

[Description of FIG. 1]

Figure 1:
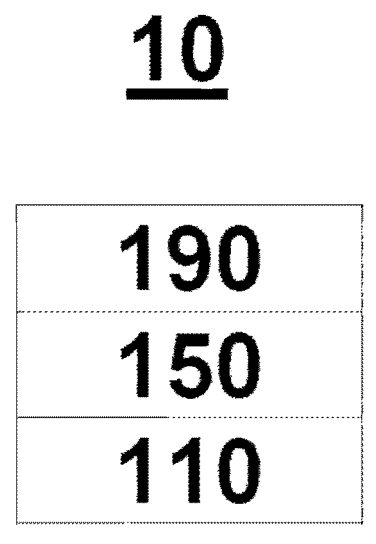

FIG. 1 is a schematic view of an organic light-emitting device 10 In one embodiment. The organic light-emitting device 10 includes a first electrode 110, an organic layer 150, and a second electrode 190.

Hereinafter, the structure of the organic light-emitting device 10 In one embodiment and a method of manufacturing the organic light-emitting device 10 will be described in connection with FIG. 1.

[First Electrode 110]

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water-resistance.

The first electrode 110 may be formed by depositing or sputtering a material for forming the first electrode 110 on the substrate. When the first electrode 110 is an anode, the material for forming the first electrode 110 may be selected from materials with a high work function to facilitate hole injection.

The first electrode 110 may be a reflective electrode, a semi-transmissive electrode, or a transmissive electrode. When the first electrode 110 is a transmissive electrode, a material for forming a first electrode may be selected from indium tin oxide (ITO), indium zinc oxide (IZO), tin oxide (SnO$_2$), zinc oxide (ZnO), and any combinations thereof, but is not limited thereto. When the first electrode 110 is a semi-transmissive electrode or a reflective electrode, as a material for forming the first electrode 110, magnesium (Mg), silver (Ag), aluminum(Al), aluminum-lithium(Al—Li), calcium (Ca), magnesium-indium(Mg—In), magnesium-silver (Mg—Ag), or any combination thereof may be used. However, the material for forming the first electrode 110 is not limited thereto.

The first electrode 110 may have a single-layer structure, or a multi-layer structure including two or more layers. For example, the first electrode 110 may have a three-layered structure of ITO/Ag/ITO, but the structure of the first electrode 110 is not limited thereto.

[Organic Layer 150]

The organic layer 150 is disposed on the first electrode 110. The organic layer 150 may include an emission layer.

The organic layer 150 may further include a hole transport region between the first electrode 110 and the emission layer, and an electron transport region between the emission layer and the second electrode 190.

[Hole Transport Region in Organic Layer 150]

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer (HIL), a hole transport layer (HTL), an emission auxiliary layer, and an electron blocking layer (EBL).

For example, the hole transport region may have a single-layer structure including a single layer including a plurality of different materials, or a multi-layer structure having a structure of hole injection layer/hole transport layer, hole injection layer/hole transport layer/emission auxiliary layer, hole injection layer/emission auxiliary layer, hole transport layer/emission auxiliary layer or hole injection layer/hole transport layer/electron blocking layer, wherein for each structure, constituting layers are sequentially stacked from the first electrode 110 in this stated order, but the structure of the hole transport region is not limited thereto.

In some embodiments, the hole transport region may include at least one selected from m-MTDATA, TDATA, 2-TNATA, NPB(NPD), β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrene sulfonate) (PEDOT/PSS), polyaniline/camphor sulfonic acid (Pani/CSA), polyaniline/poly(4-styrenesulfonate) (PANI/PSS), a compound represented by Formula 201, and a compound represented by Formula 202:

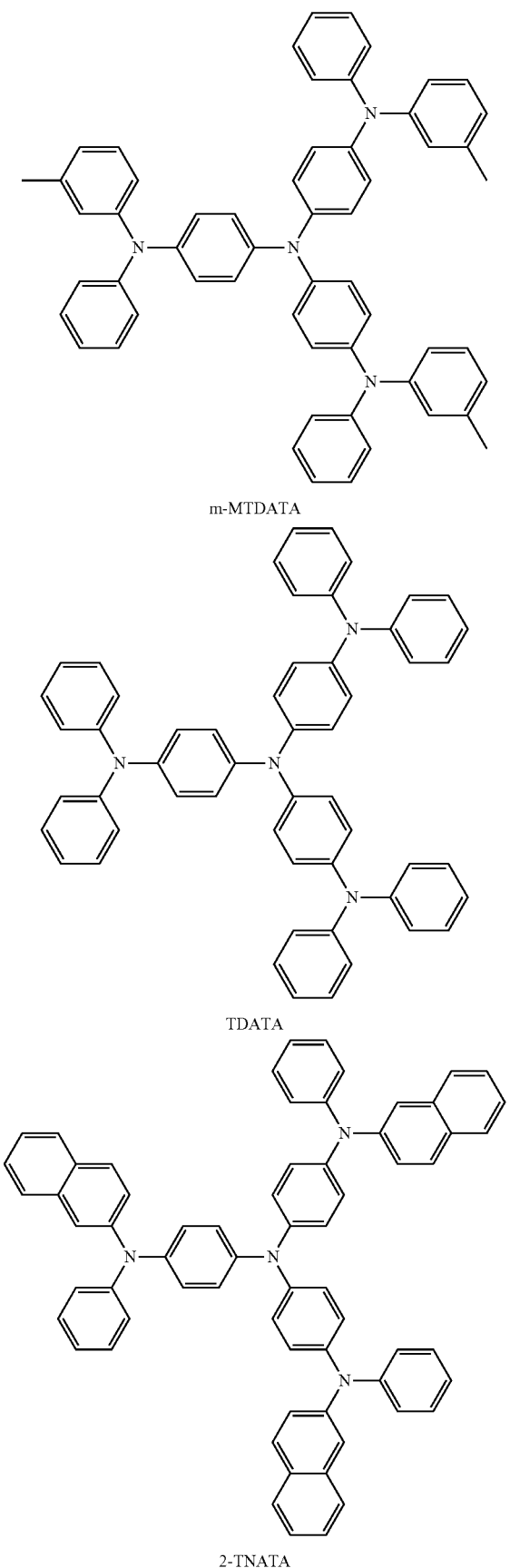

m-MTDATA

TDATA

2-TNATA

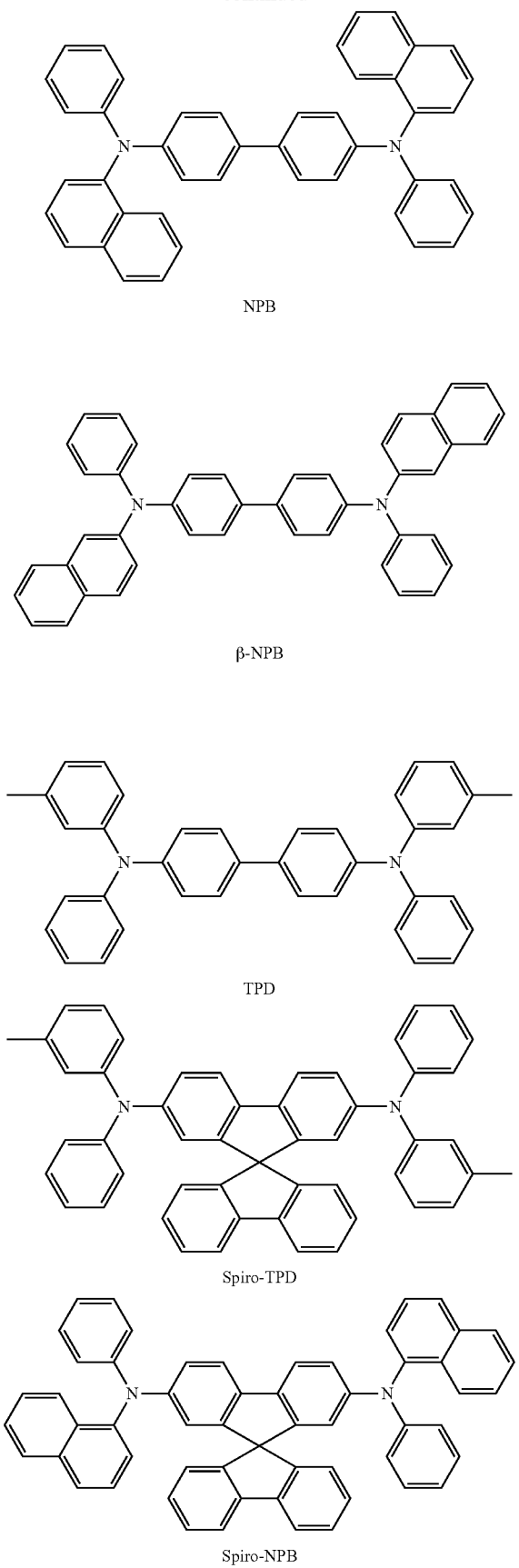

NPB

β-NPB

TPD

Spiro-TPD

Spiro-NPB

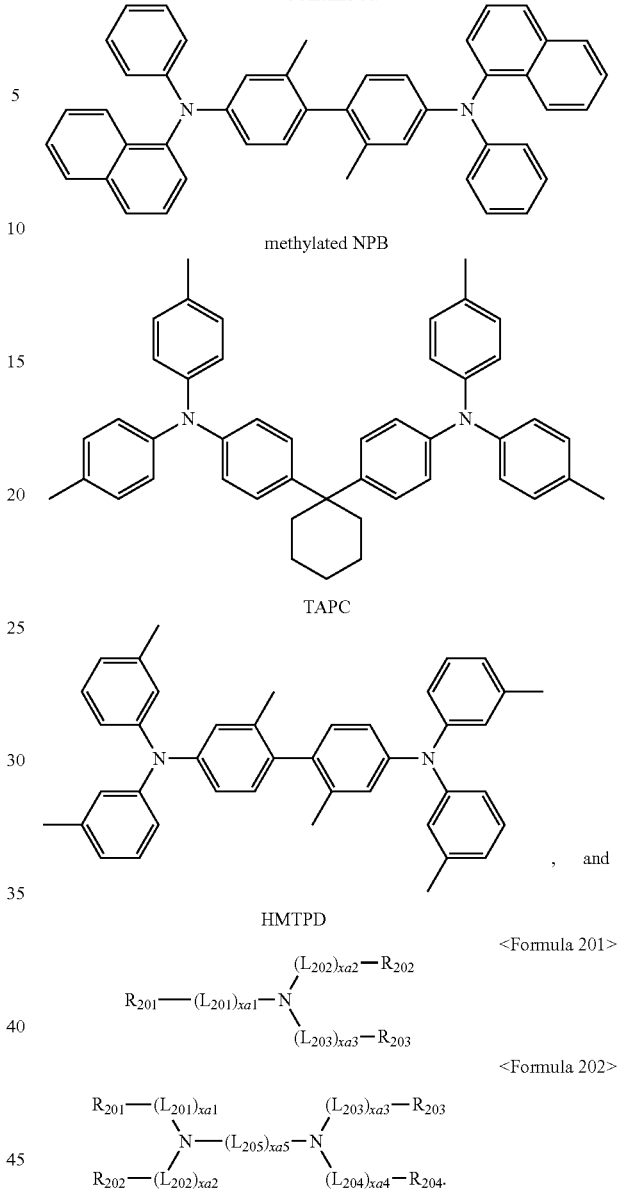

methylated NPB

TAPC

HMTPD

, and

<Formula 201>

$$R_{201}—(L_{201})_{xa1}—N\begin{smallmatrix}(L_{202})_{xa2}—R_{202}\\(L_{203})_{xa3}—R_{203}\end{smallmatrix}$$

<Formula 202>

$$\begin{matrix}R_{201}—(L_{201})_{xa1}&&(L_{203})_{xa3}—R_{203}\\&N—(L_{205})_{xa5}—N&\\R_{202}—(L_{202})_{xa2}&&(L_{204})_{xa4}—R_{204}.\end{matrix}$$

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—N($Q_{201}$)—*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer selected of 0 to 3, xa5 may be an integer selected of 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 202, $R_{201}$ and $R_{202}$ may be optionally linked with each other through a single bond, a dimethyl-methylene group, or a diphenyl-methylene group, and $R_{203}$ and $R_{204}$ may be optionally linked with each other through a single bond, a dimethyl-methylene group, or a diphenyl-methylene group.

In one embodiment, $L_{201}$ to $L_{205}$ in Formulae 201 and 202 may each independently be selected from:

a phenylene group, a pentalenylene group, an indenylene group, a naphthylene group, an azulenylene group, a heptalenylene group, an indacenylene group, an acenaphthenylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthenylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthenyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si$(Q_{31})(Q_{32})(Q_{33})$, and —N$(Q_{31})(Q_{32})$, and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In some embodiments, xa1 to xa4 may each independently be 0, 1, or 2.

In some embodiments, xa5 may be 1, 2, 3, or 4.

In some embodiments, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthenyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group and a pyridinyl group; and a phenyl group, a biphenyl group, a terphenyl group, a pentalenyl group, an indenyl group, a naphthyl group, an azulenyl group, a heptalenyl group, an indacenyl group, an acenaphthenyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthenyl group, a fluorenyl group, a spirobifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$).

$Q_{31}$ to $Q_{33}$ may be to the same as described above.

In some embodiments, at least one selected from $R_{201}$ to $R_{203}$ in Formula 201 may each independently be selected from a fluorenyl group, a spiro-bifluorenyl group, a carbazolyl group, a dibenzofuranyl group and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but is not limited thereto.

In some embodiments, in Formula 202, i) $R_{201}$ and $R_{202}$ may be linked with each other through a single bond, and/or ii) $R_{203}$ and $R_{204}$ may be linked with each other through a single bond.

In some embodiments, at least one of $R_{201}$ to $R_{204}$ in Formula 202 may be selected from:

a carbazolyl group; and a carbazolyl group, substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but are not limited thereto.

A compound represented by Formula 201 may be represented by Formula 201A:

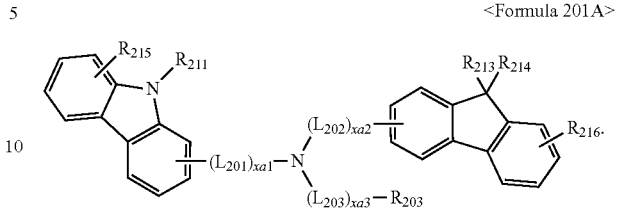

<Formula 201A>

For example, the compound represented by Formula 201 may be represented by Formula 201A(1), but is not limited thereto:

<Formula 201A(1)>

In some embodiments, the compound represented by Formula 201 may be represented by Formula 201A-1, but is not limited thereto:

<Formula 201A-1>

The compound represented by Formula 202 may be represented by Formula 202A:

<Formula 202A>

In some embodiments, the compound represented by Formula 202 may be represented by Formula 202A-1:

<Formula 202A-1>

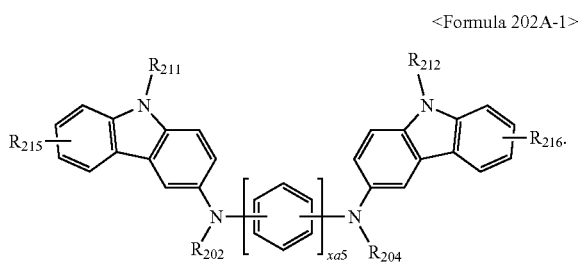

In Formulae 201A, 201A(1), 201A-1, 202A, and 202A-1, $L_{201}$ to $L_{203}$, xa1 to xa3, xa5, and $R_{202}$ to $R_{204}$ may be the same as described above, $R_{211}$ and $R_{212}$ may be the same as described above in connection with $R_{203}$, $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthenyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but is not limited thereto:

HT1

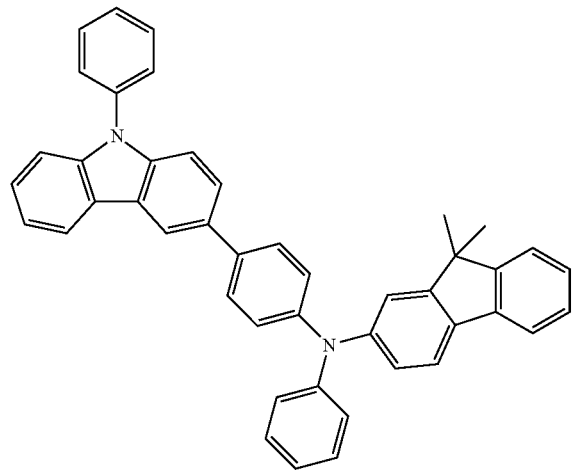

HT2

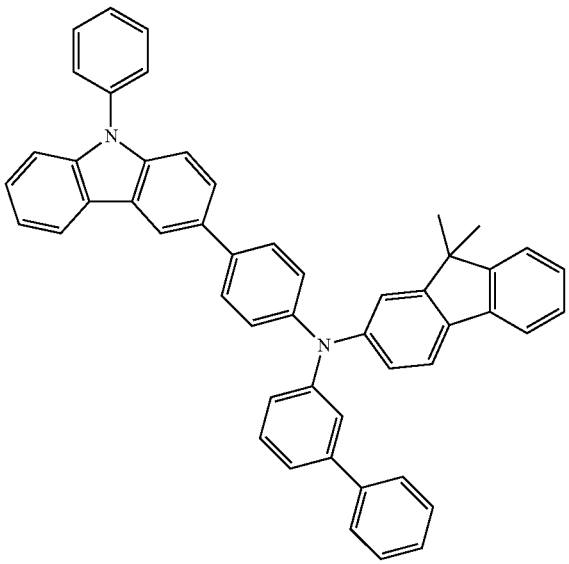

-continued
HT3
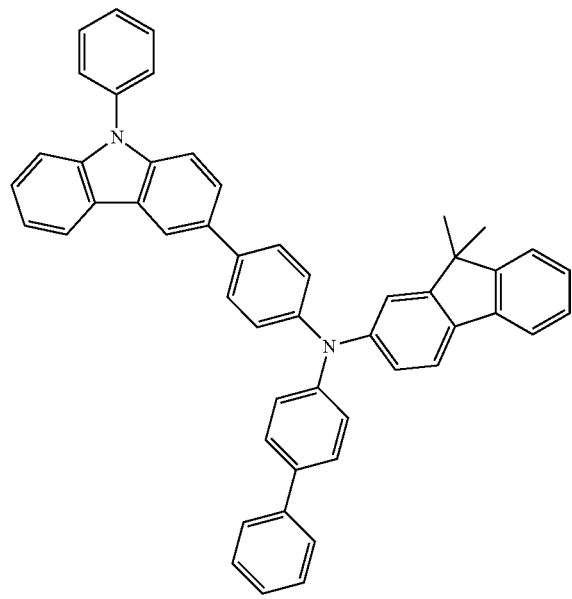
HT4
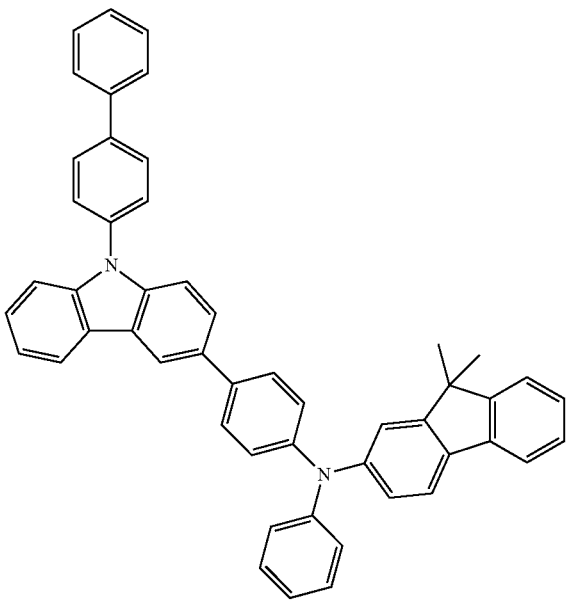
HT5
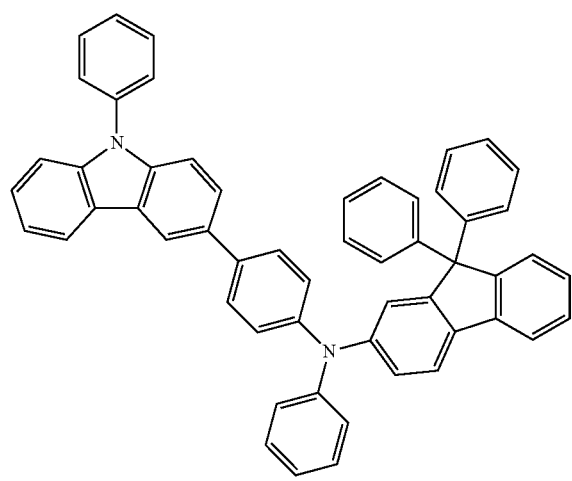
HT6
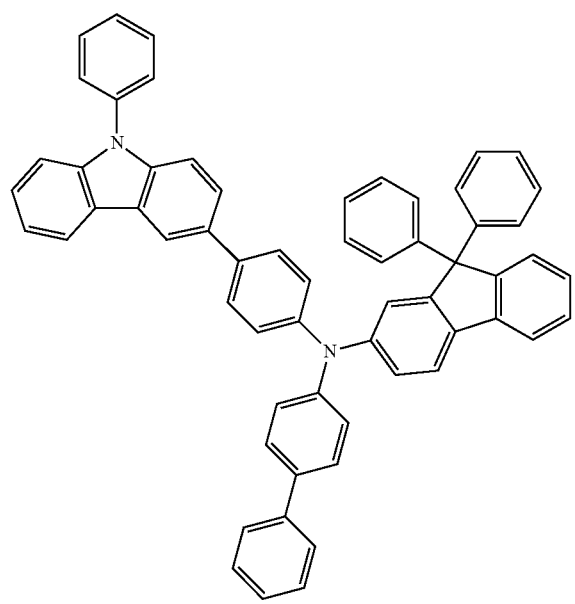

-continued
HT7
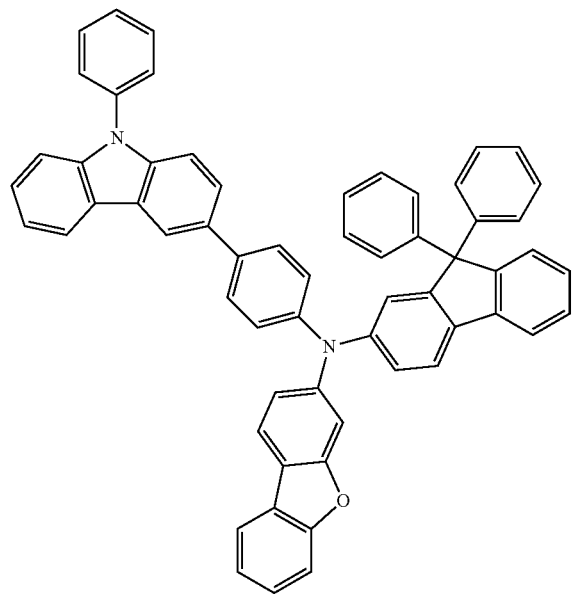
HT8
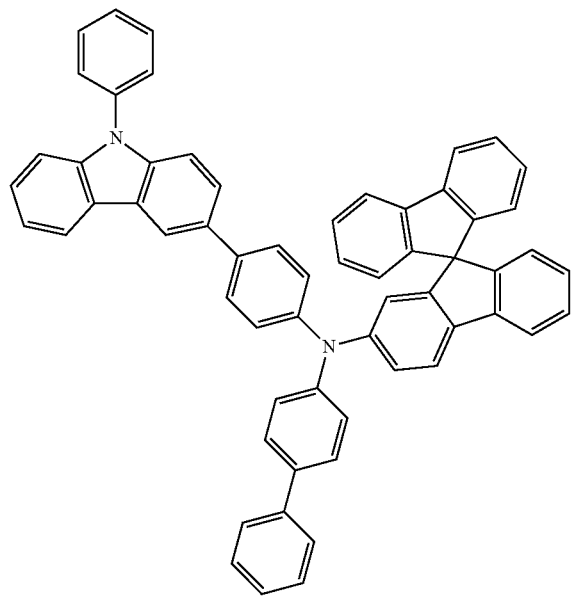
HT9
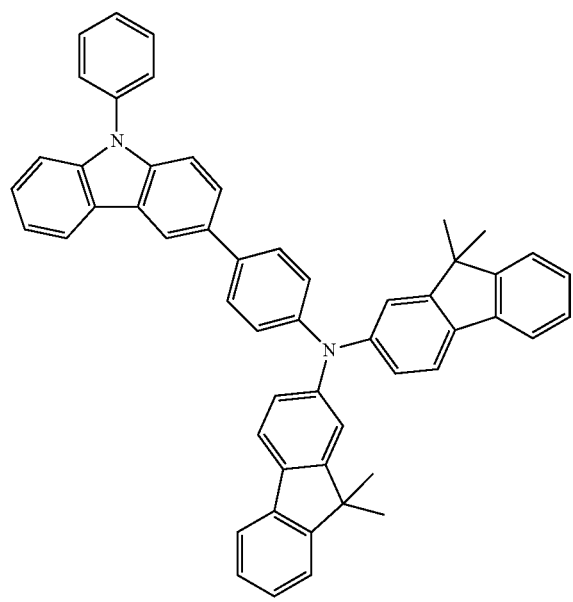
HT10
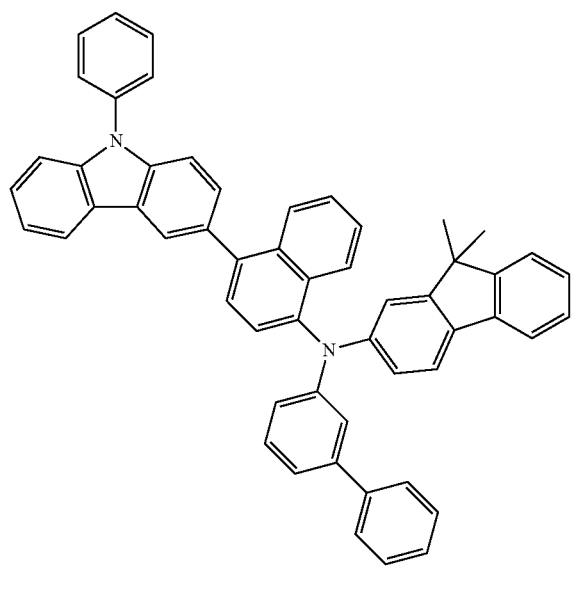

-continued
HT11
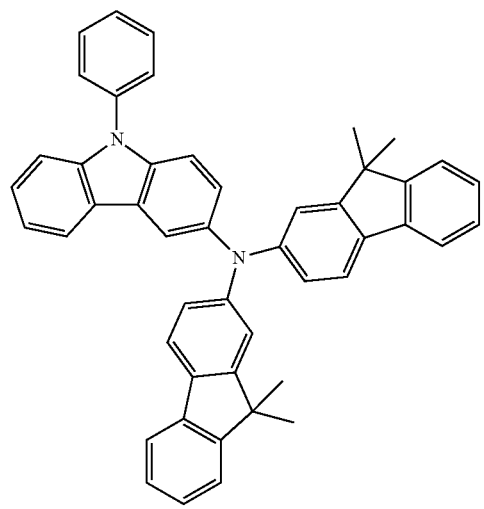
HT12
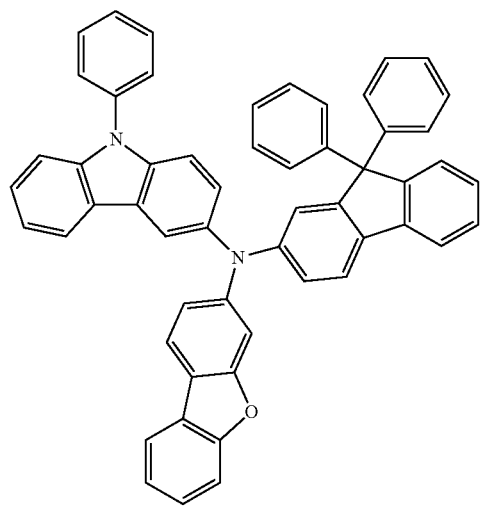
HT13
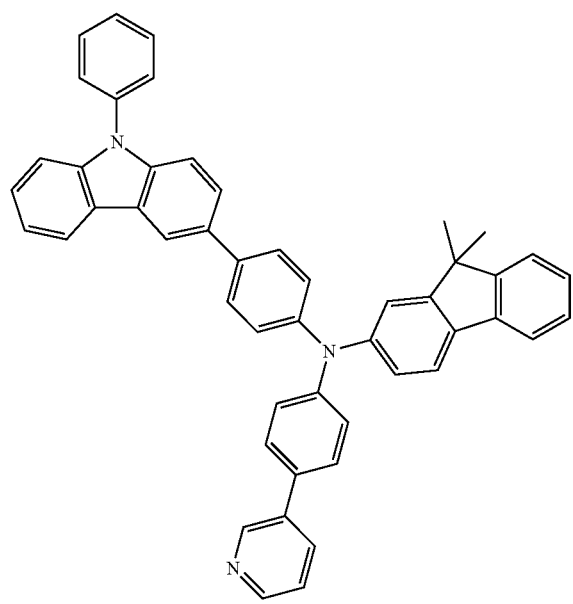
HT14
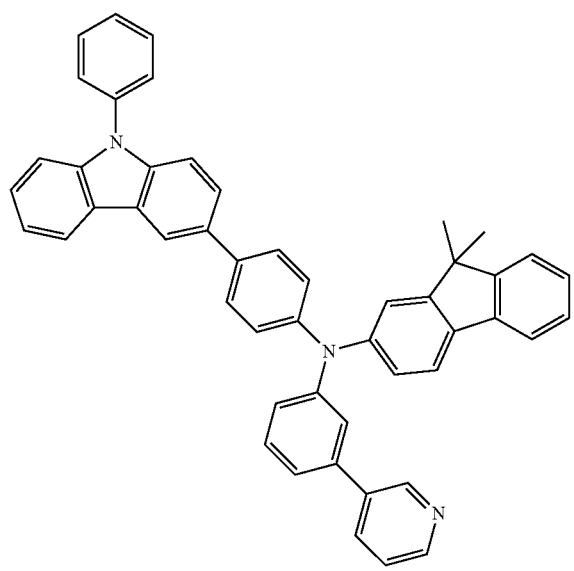
HT15
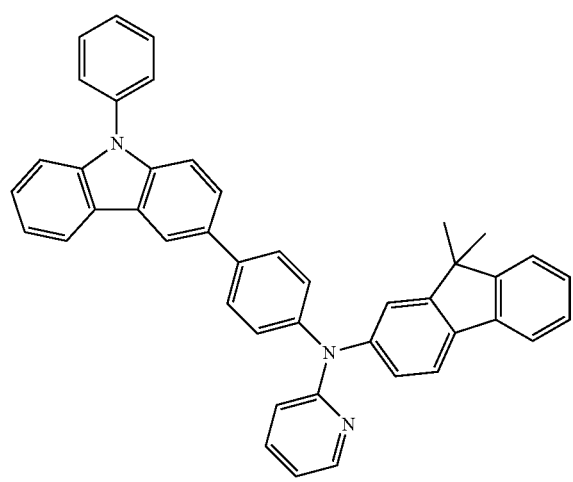
HT16
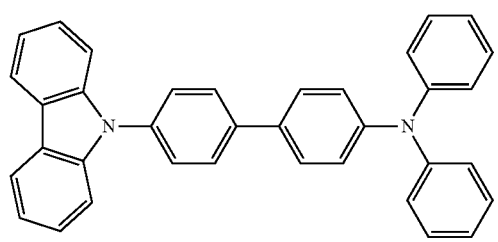

-continued
HT17
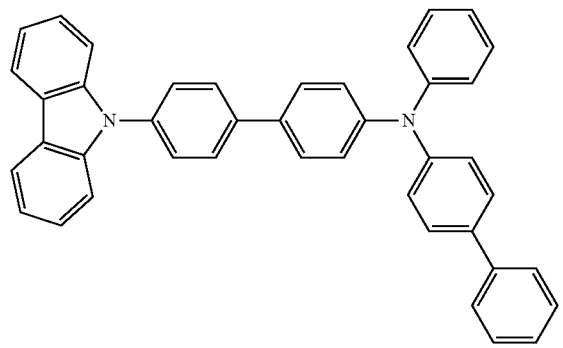
HT18
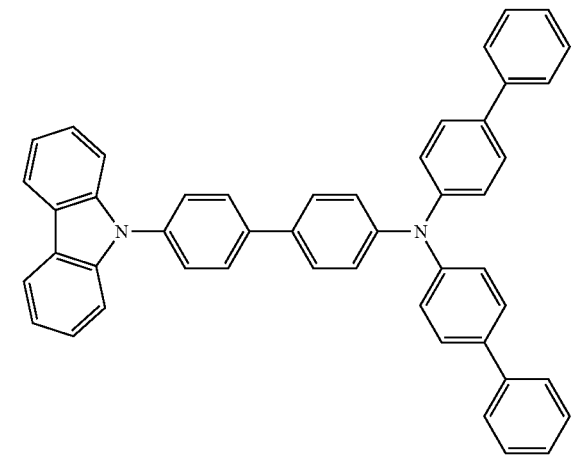
HT19
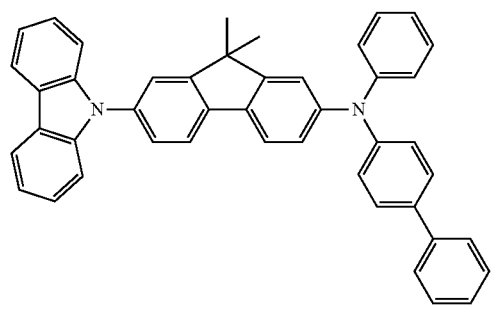
HT20
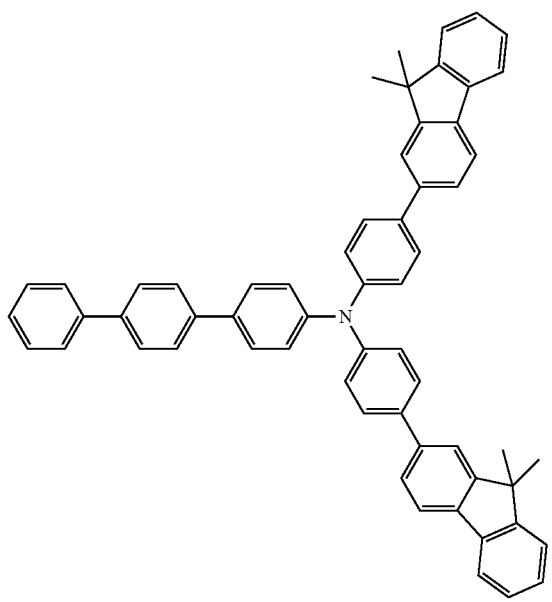
HT21
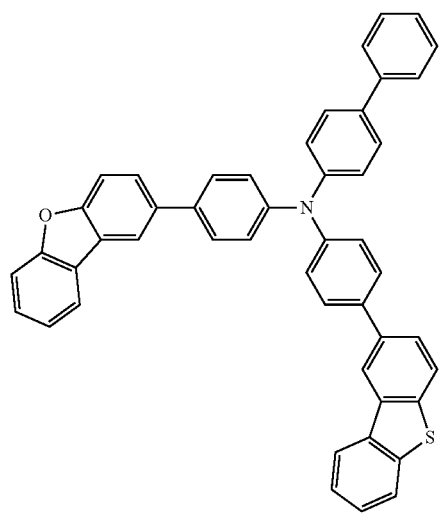
HT22
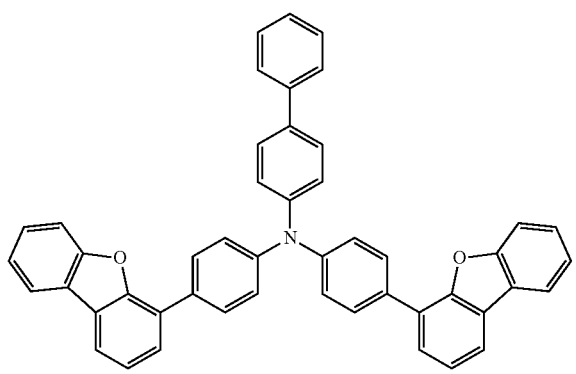

-continued
HT23
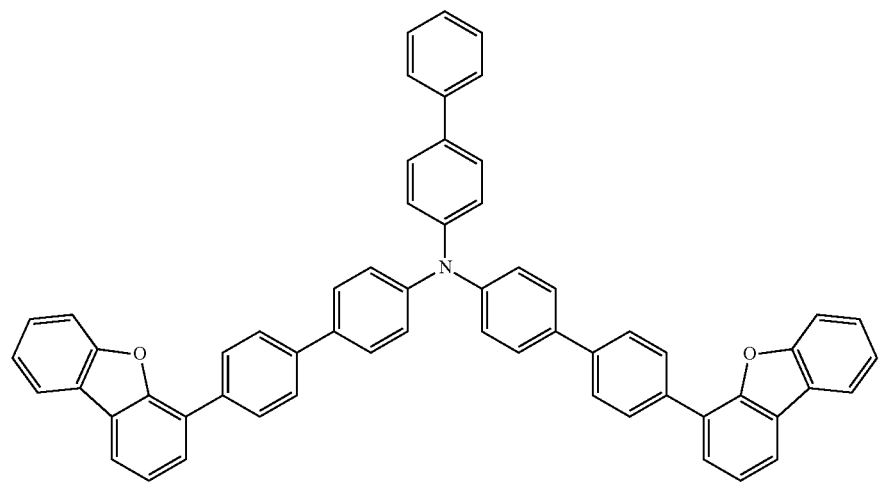
HT24
HT25
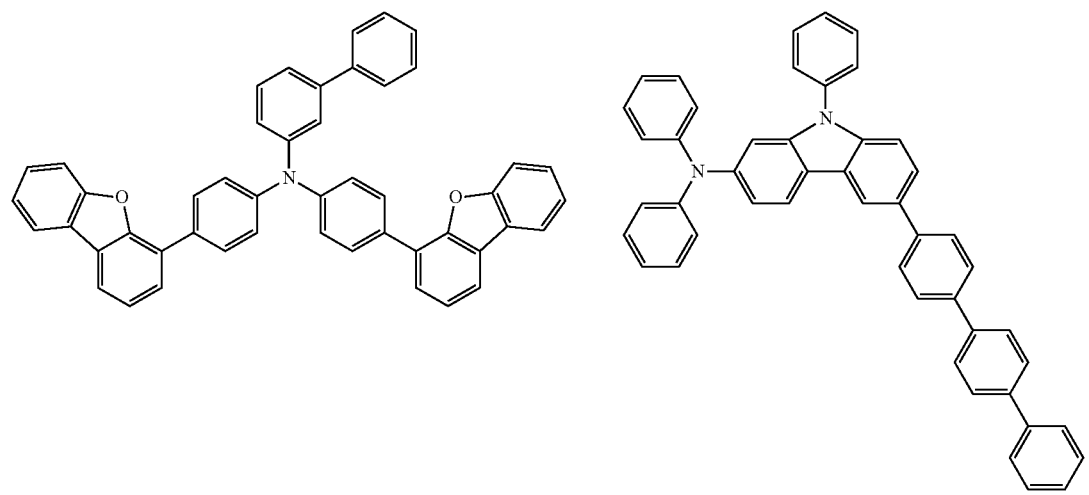
HT26
HT27
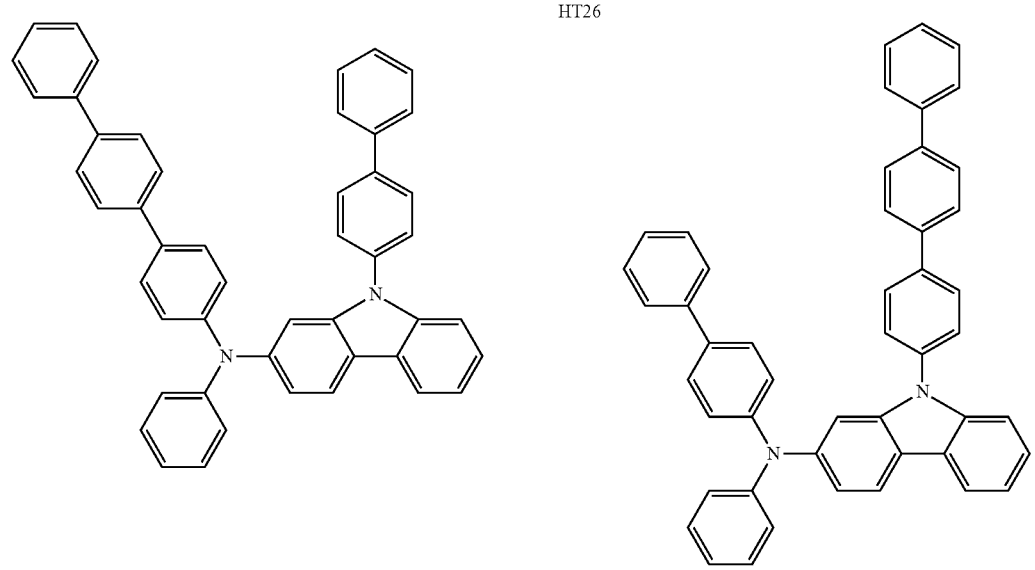

-continued
HT28
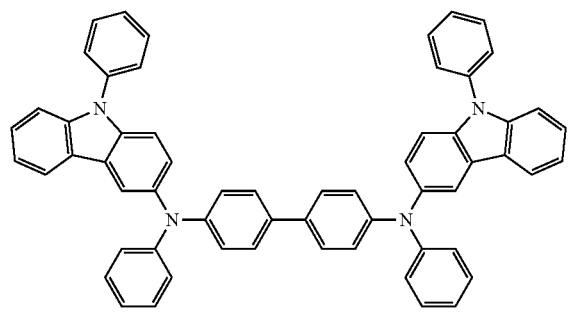
HT29
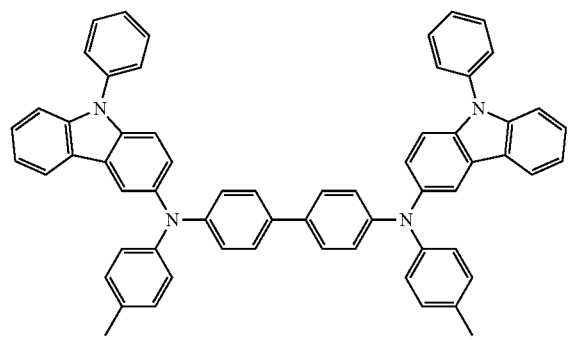
HT30
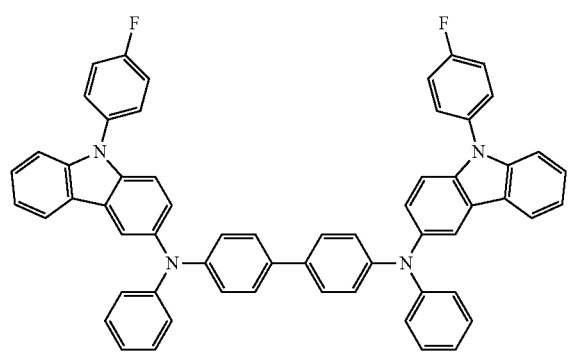
HT31
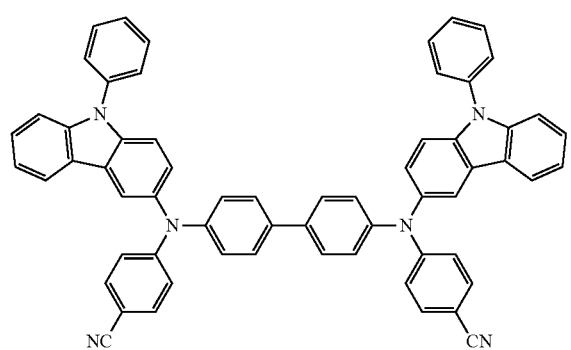
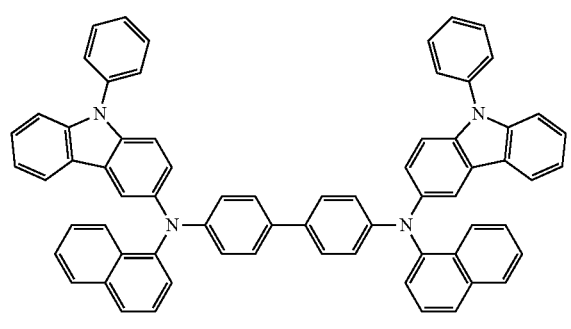
HT33
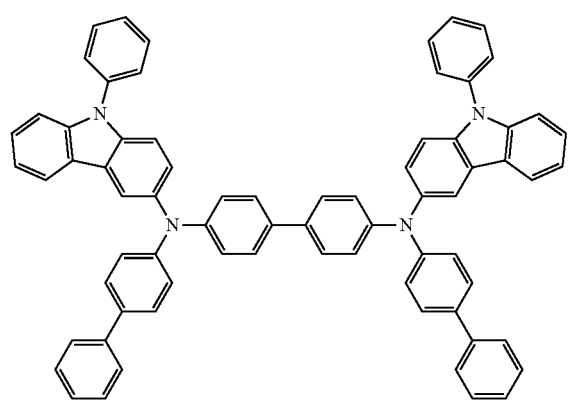

-continued
HT34
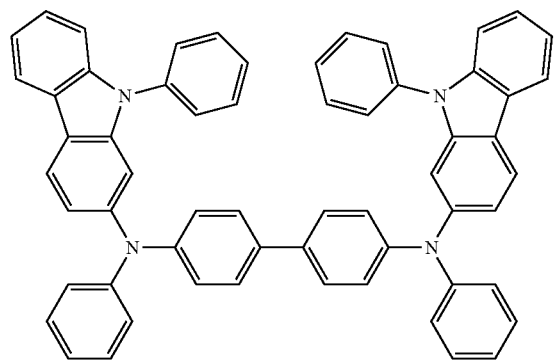
HT35
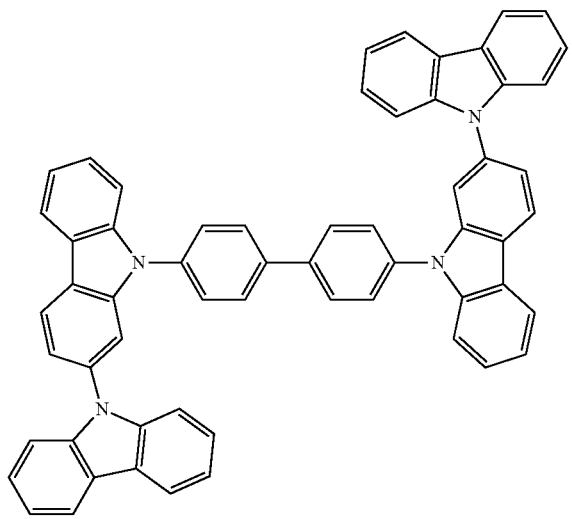
HT36
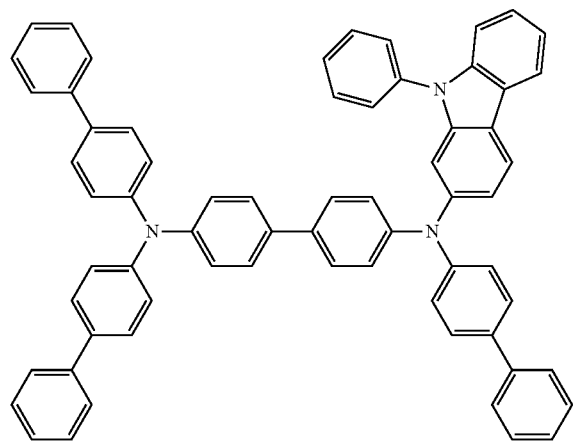
HT37
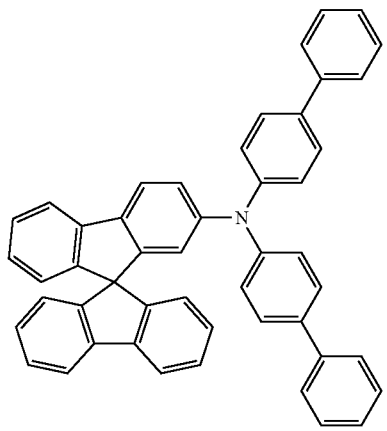
HT38
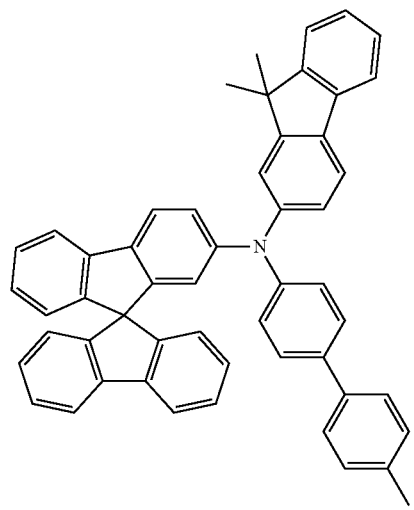
HT39
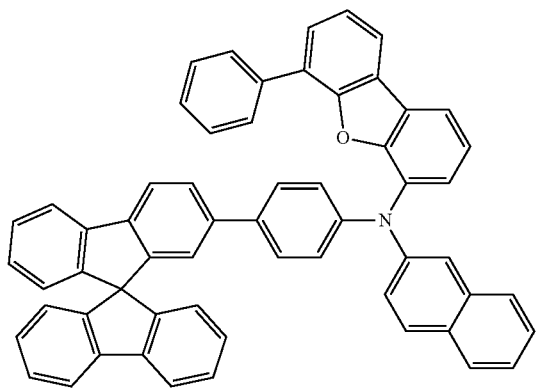

A thickness of the hole transport region may be from about 100 Å to about 10000 Å, for example, about 100 Å to about 1,000 Å. When the hole transport region includes at least one of a hole injection layer and a hole transport layer, the thickness of the hole injection layer may be from about 100 Å to about 9,000 Å, and for example, about 100 Å to about 1,000 Å, and the thickness of the hole transport layer may be from about 50 Å to about 2,000 Å, and for example, about 100 Å to about 1,500 Å. When the thicknesses of the hole transport region, the hole injection layer and the hole transport layer are within these ranges, satisfactory hole transporting characteristics may be obtained without a substantial increase in driving voltage.

The electron blocking layer prevents injection of electrons from the electron transport region. The emission auxiliary layer and the electron blocking layer may include those materials as described above. The emission auxiliary layer may include the condensed cyclic compound represented by Formula 1.

[p-dopant]

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, a lowest unoccupied molecular orbital (LUMO) of the p-dopant may be −3.5 eV or less.

The p-dopant may include at least one selected from a quinone derivative, a metal oxide, and a cyano group-containing compound, but embodiments are not limited thereto.

For example, the p-dopant may include at least one selected from a quinone derivative, such as tetracyanoquinodimethane (TCNQ) and 2,3,5,6-tetrafluoro-7,7,8,8-tetracyanoquinodimethane (F4-TCNQ);

a metal oxide, such as tungsten oxide, and molybdenum oxide;

1,4,5,8,9,11-hexaazatriphenylene-hexacarbonitrile (HAT-CN); and a compound represented by Formula 221, but is not limited thereto:

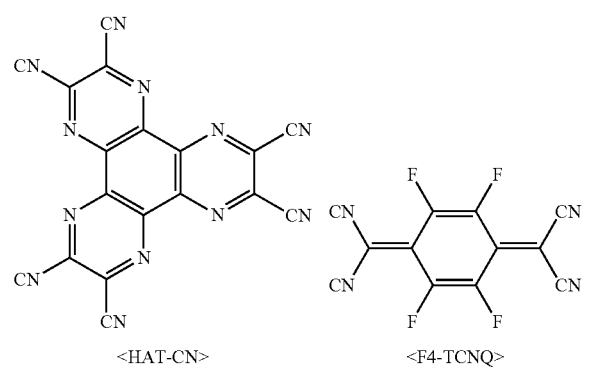

<HAT-CN>          <F4-TCNQ>

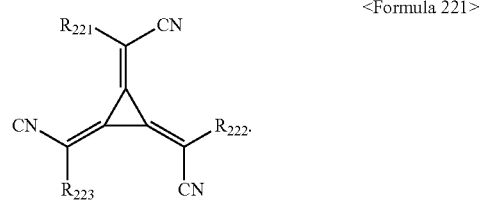

<Formula 221>

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one selected from $R_{221}$ to $R_{223}$ has at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with Br, and a $C_1$-$C_{20}$ alkyl group substituted with -I.

[Emission Layer in Organic Layer 150]

When the organic light-emitting device 10 is a full color organic light-emitting device, the emission layer may be patterned into a red emission layer, a green emission layer, or a blue emission layer, according to a sub pixel. In some embodiments, the emission layer may have a stacked structure of two or more layers selected from a red emission layer, a green emission layer, and a blue emission layer, in which the two or more layers contact each other or are separated from each other. In some embodiments, the emission layer may include two or more materials selected from a red-light emission material, a green-light emission material, and a blue-light emission material, in which the two or more materials are mixed with each other in a single layer to emit white light.

The emission layer may include a host and a dopant. The dopant may be at least one selected from a phosphorescent dopant and a fluorescent dopant.

An amount of the dopant in the emission layer may be, in general, from about 0.01 to about 15 parts by weight based on 100 parts by weight of the host, but is not limited thereto.

A thickness of the emission layer may be from about 100 Å to about 1000 Å, for example, about 200 Å to about 600 Å. When the thickness of the emission layer is within this range, excellent light-emission characteristics may be obtained without a substantial increase in driving voltage.

[Host in Emission Layer]

The host may include the condensed cyclic compound represented by Formula 1.

In one embodiment, the emission layer includes a host and a dopant, the host may include the condensed cyclic compound represented by Formula 1, and the dopant may include a blue phosphorescent dopant.

[Phosphorescent Dopant Included in Emission Layer in Organic Layer 150]

The phosphorescent dopant may include an organometallic complex represented by Formula 401 below:

$$M(L_{401})_{xc1}(L_{402})_{xc2}$$  <Formula 401>

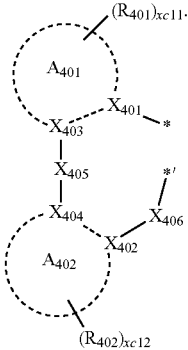

<Formula 402>

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be a ligand represented by Formula 402, and xc1 may be 1, 2 or 3, wherein when xc1 is two or more two or more $L_{401}$(s) may be identical to or different from each other, $L_{402}$ may be an organic ligand, and xc2 may be an integer selected of 0 to 4, wherein when xc2 is two or more, two or more $L_{402}$(s) may be identical to or different from each other, $X_{401}$ to $X_{404}$ may each independently be nitrogen or carbon, $X_{401}$ and $X_{403}$ may be linked to each other through a single bond or a double bond, and $X_{402}$ and $X_{404}$ may be linked to each other through a single bond or a double bond, $A_{401}$ and $A_{402}$ may each independently be a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)—*', *—C($Q_{411}$)($Q_{412}$)—*', *—C($Q_{411}$)=C($Q_{412}$)—*', *—C($Q_{411}$)*', or *C($Q_{411}$)=*', and $Q_{411}$ and $Q_{412}$ may be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), and $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer selected of 0 to 10, In Formula 402, * and *' may be a binding site for M in Formula 401.

In one embodiment, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzoimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In some embodiments, in Formula 402, i) $X_{401}$ may be nitrogen, $X_{402}$ may be carbon, or ii) both $X_{401}$ and $X_{402}$ may be nitrogen.

In some embodiments, in Formula 402, R401 and R402 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a C1-C20 alkoxy group;

a C1-C20 alkyl group, and a C1-C20 alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si(Q$_{401}$)(Q$_{402}$)(Q$_{403}$), —N(Q$_{401}$)(Q$_{402}$), —B(Q$_{401}$)(Q$_{402}$), —C(=O)(Q$_{401}$), —S(=O)$_2$(Q$_{401}$), and —P(=O)(Q$_{401}$)(Q$_{402}$), wherein Q$_{401}$ to Q$_{403}$ may each independently be selected from a C$_1$-C$_{10}$ alkyl group, a C$_1$-C$_{10}$ alkoxy group, a phenyl group, a biphenyl group, and a naphthyl group, but are not limited thereto.

In some embodiments, in Formula 401, when xc1 is two or more, two A$_{401}$(s) of two or more L$_{401}$ may be optionally linked with each other through X$_{407}$ that is a linking group, or two A$_{402}$(s) may be optionally linked with each other through X$_{408}$ that is a linking group (see Compounds PD1 to PD4 and PD7). X$_{407}$ and X$_{408}$ may each independently be a single bond, *—O—*', *—S—*', *—C(=O)—*', *—N(Q$_{413}$)—*', *—C(Q$_{413}$)(Q$_{414}$)—*', or *—C(Q$_{413}$)C(Q$_{414}$)—*' (wherein, Q$_{413}$ and Q$_{414}$ may each independently be hydrogen, deuterium, a C$_1$-C$_{20}$ alkyl group, a C$_1$-C$_{20}$ alkoxy group, a phenyl group, a biphenyl group, a terphenyl group, or a naphthyl group), but are not limited thereto.

L$_{402}$ in Formula 401 may be a monovalent, divalent, or trivalent organic ligand. For example, L$_{402}$ may be selected from halogen, diketone (for example, acetylacetonate), a carboxylic acid (for example, picolinate), —C(=O), isonitrile, —CN and phosphorus (for example, phosphine), and phosphite, but is not limited thereto.

In some embodiments, the phosphorescent dopant may be selected from, for example, Compounds PD1 to PD25 and Firpic, but is not limited thereto

PD1

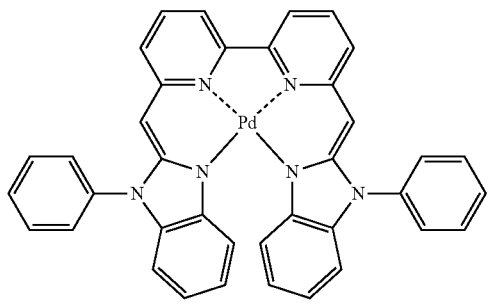

PD2

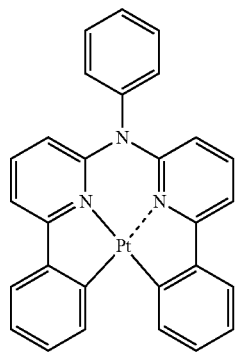

PD3

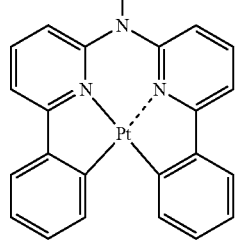

PD4

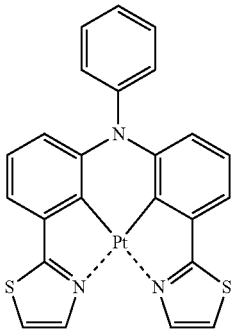

PD5

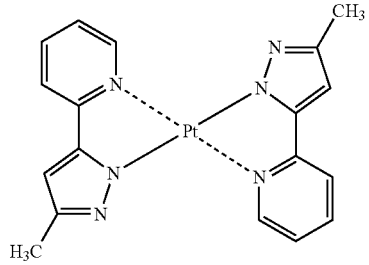

PD6

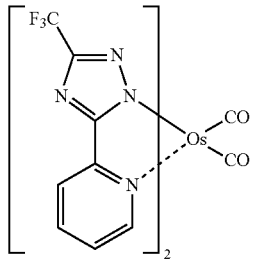

PD7

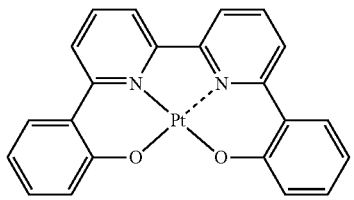

PD8

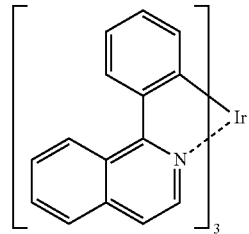

PD9

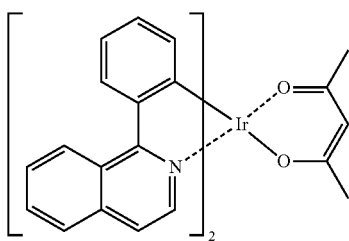

PD10
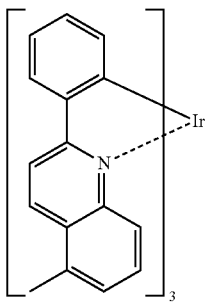
PD11
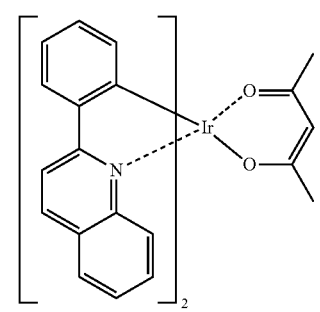
PD12
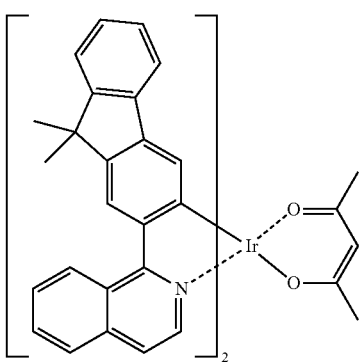
PD13
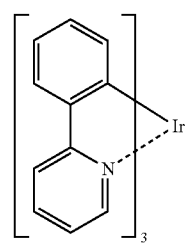
PD14
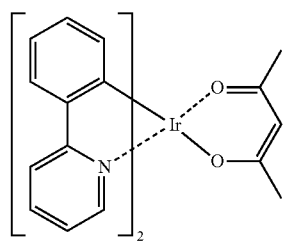
PD15
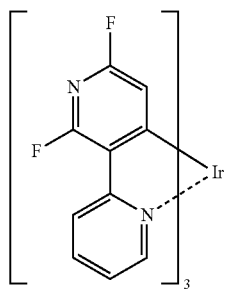
PD16
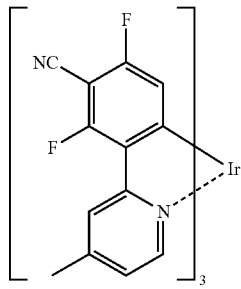
PD17
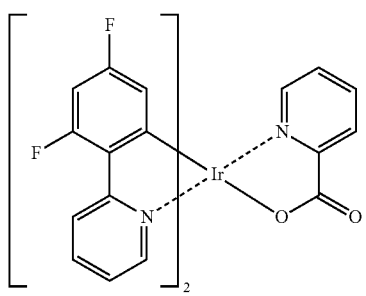
PD18
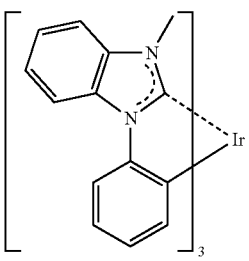
PD19
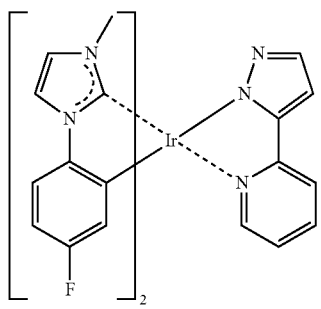

PD20 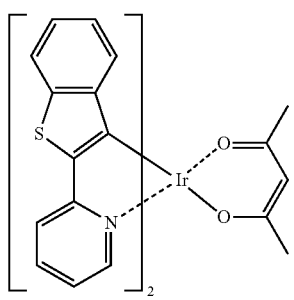

PD21 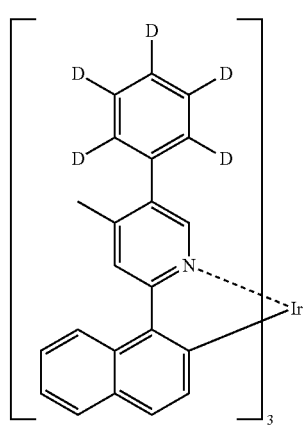

PD22 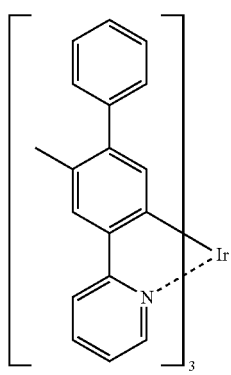

PD23 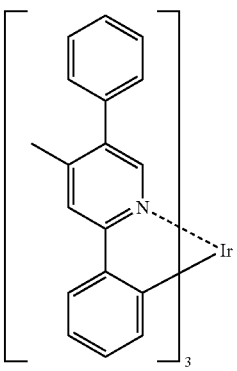

PD24 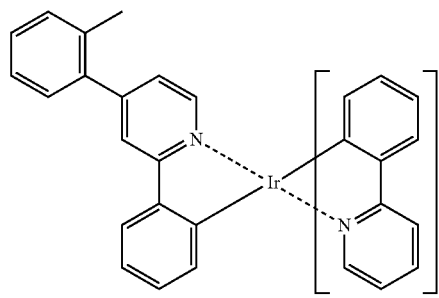

PD25 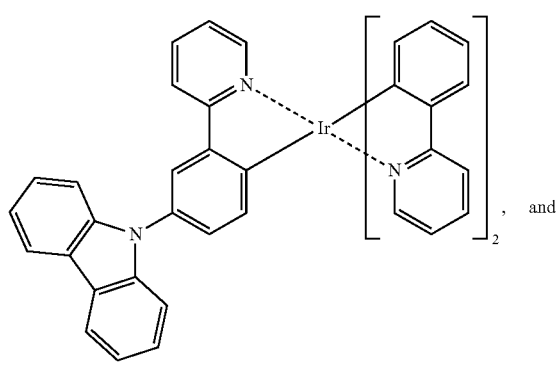

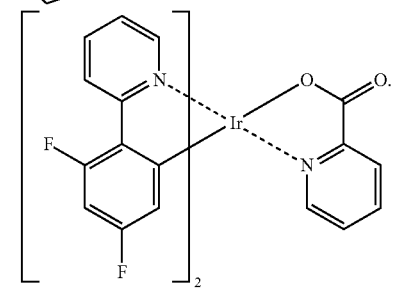
<Firpic>

[Fluorescent Dopant in Emission Layer]

The fluorescent dopant may include an arylamine compound or styrylamine compound.

The fluorescent dopant may include a compound represented by Formula 501 below.

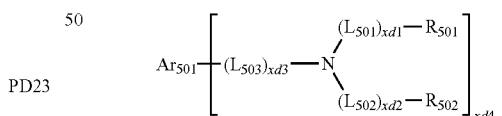
<Formula 501>

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer of 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer of 1 to 6.

In one embodiment, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In some embodiments, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a benzosilolylene group, a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In some embodiments, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), wherein $Q_{31}$ to $Q_{33}$ may be selected from a $C_1$-$C_{10}$ alkyl group, a $C_1$-$C_{10}$ alkoxy group, a phenyl group, a biphenyl group, a terphenyl group, and a naphthyl group.

In some embodiments, xd4 in Formula 501 may be 2, but is not limited thereto.

For example, the fluorescent dopant may be selected from Compounds FD1 to FD22:
FD1
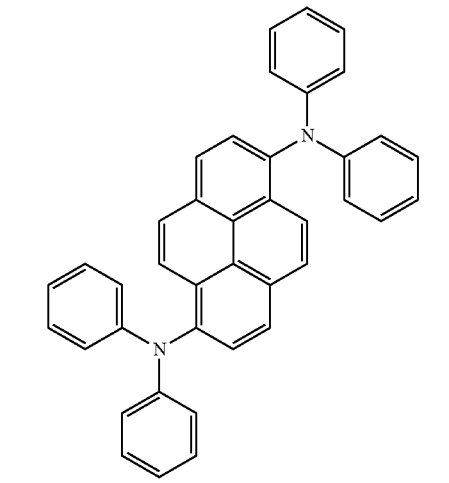
FD2
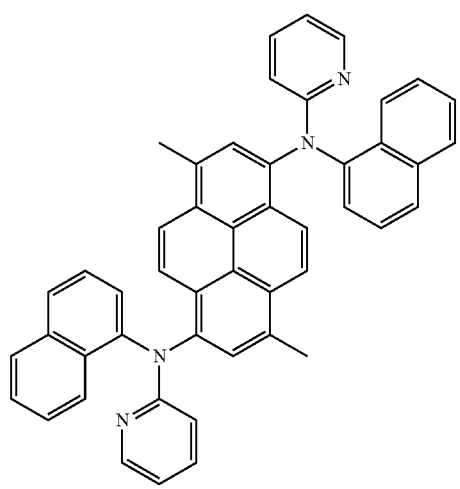
FD3
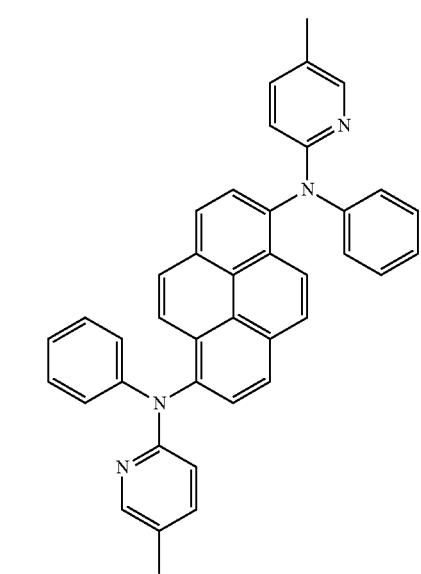
-continued
FD4
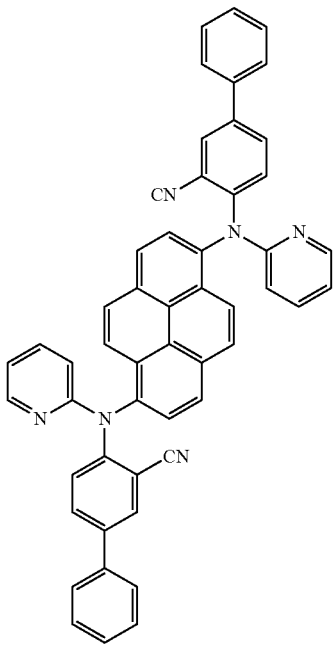
FD5
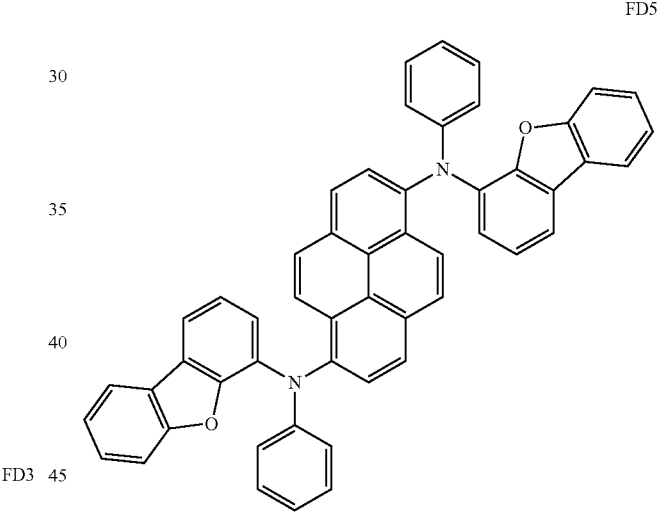
FD6
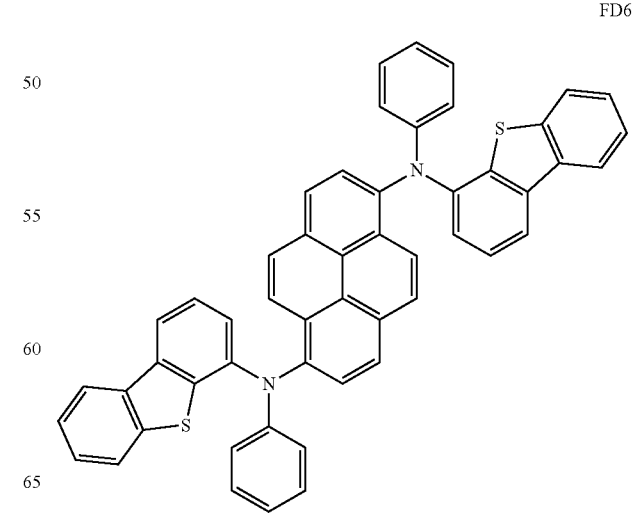

-continued
FD7
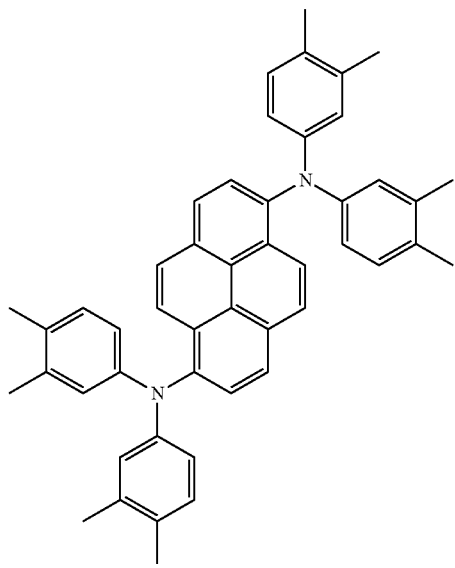
FD8
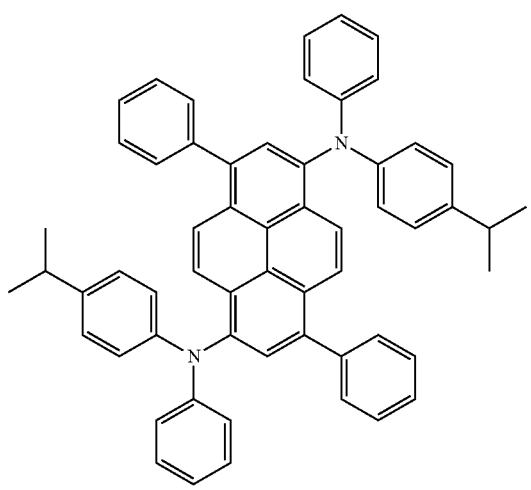
FD9
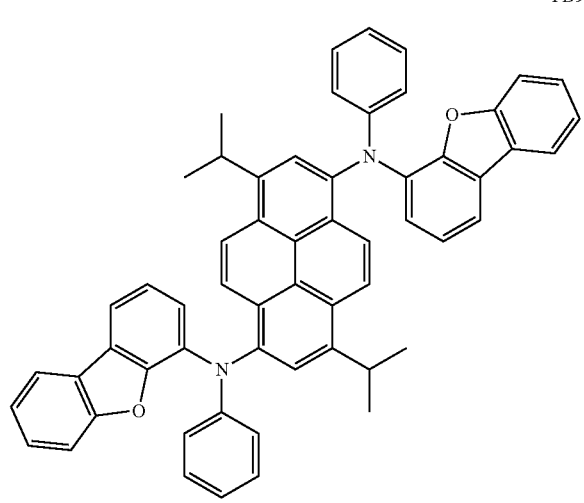
-continued
FD10
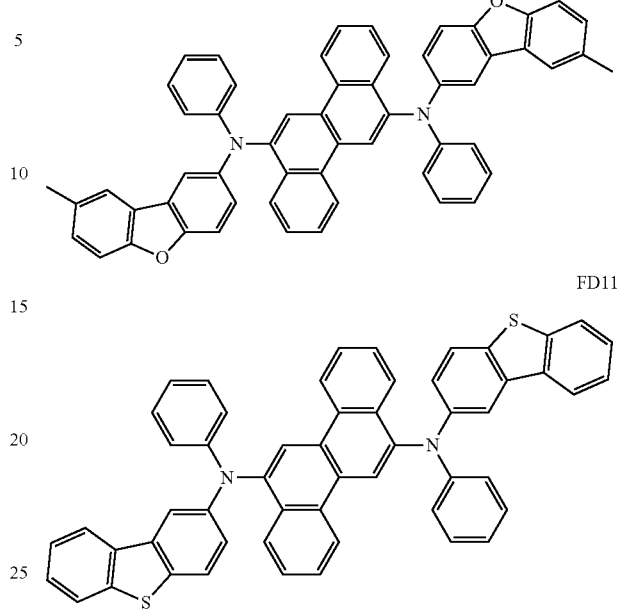
FD11
FD12
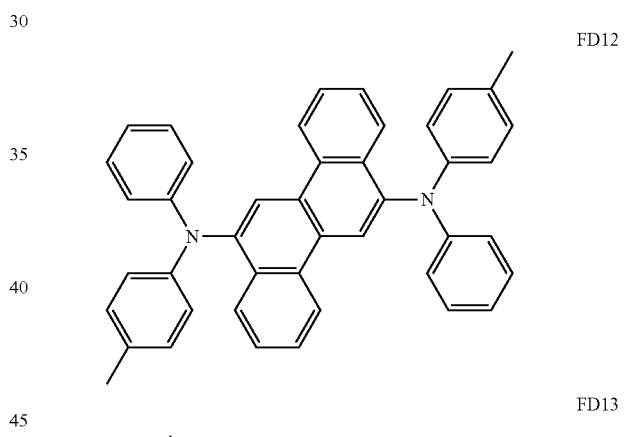
FD13
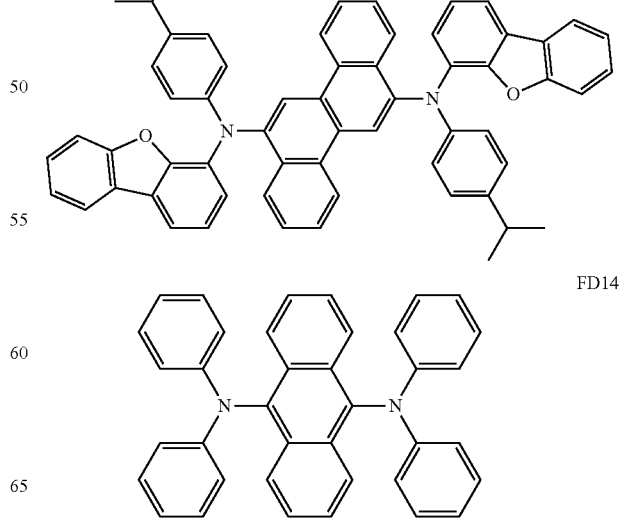
FD14

FD15
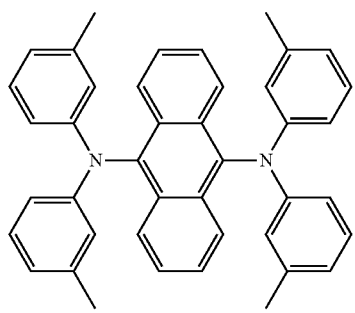
FD16
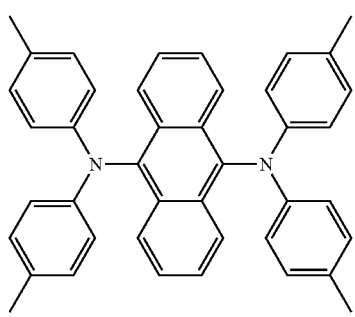
FD17
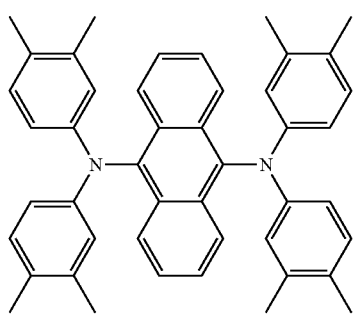
FD18
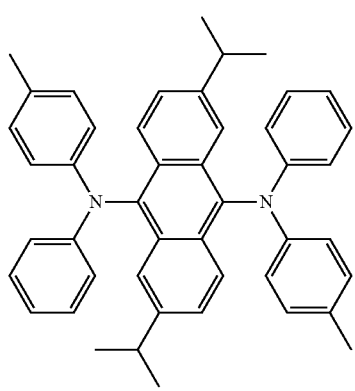
FD19
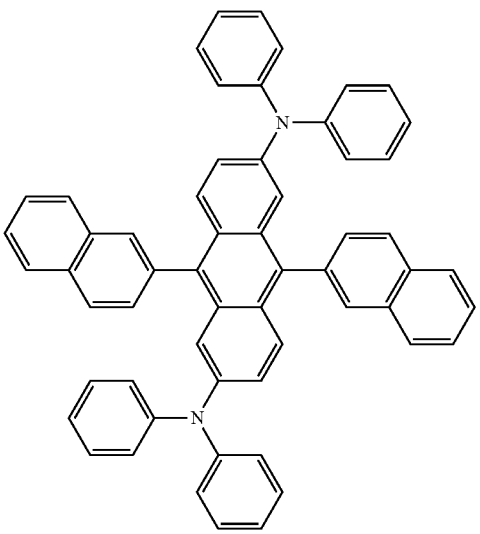
FD20
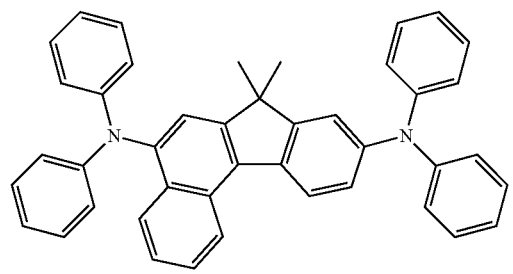
FD21
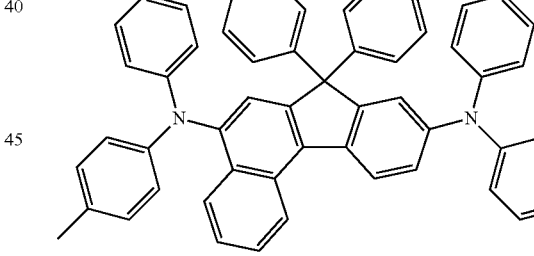
FD22
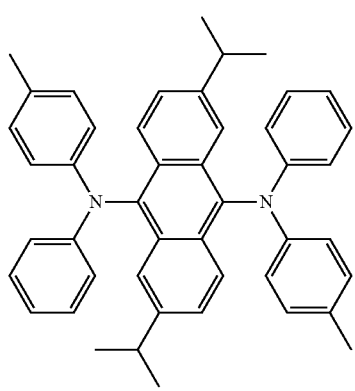
In some embodiments, the fluorescent dopant may be selected from the following compounds, but is not limited thereto:

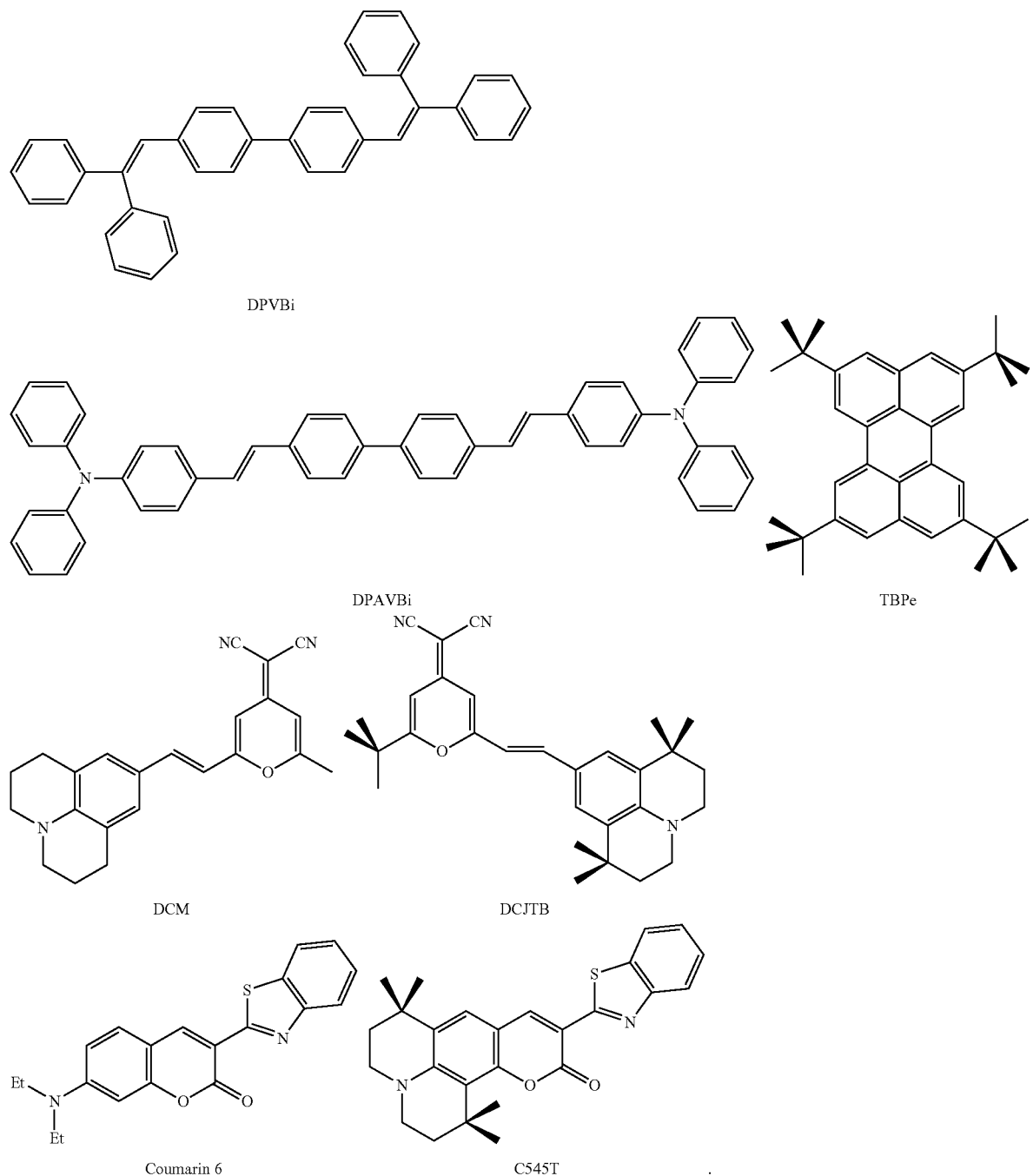

[Electron Transport Region in Organic Layer 150]

The electron transport region may have i) a single layer structure including a single layer having a single material, ii) a single layer structure including a single layer having a plurality of different materials, or iii) a multi-layer including a plurality of layers having a plurality of different materials.

The electron transport region may include at least one layer selected from a buffer layer, a hole blocking layer, an electron controlling layer, an electron transport layer (ETL), and an electron injection layer, but is not limited thereto. For example, the electron transport region may have a structure of an electron transport layer/electron injection layer, a hole blocking layer/electron transport layer/electron injection layer, an electron controlling layer/electron transport layer/electron injection layer, or a buffer layer/electron transport layer/electron injection layer which is laminated from the emission layer, but is not limited thereto.

The electron transport region (for example, the buffer layer, hole blocking layer, electron controlling layer or electron transport layer in the electron transport region) may include a metal-free compound including at least one π electron-depleted nitrogen-containing ring.

The "π electron-depleted nitrogen-containing ring" may be a ring-forming moiety, and means a $C_1$-$C_{60}$ heterocyclic group having at least one *—N=*' moiety.

For example, the "π electron-depleted nitrogen-containing ring" may be i) one selected from a 5-membered to 7-membered heteromonocyclic group, each having at least one *—N=*' moiety, ii) a heteropolycyclic group in which two or more selected from 5-membered to 7-membered heteromonocyclic groups, each having at least one *—N=*' moiety, are condensed with each other or iii) a heteropolycyclic group in which at least one selected from 5-membered to 7-membered heteromonocyclic groups, each having at least one *—N=*' moiety, is condensed with at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzoimidazole, an iso-benzothiazole, a benzoxazole, an isobenzoxazole, a triazole, a tetrazole, an oxadiazole, a triazine, a thiadiazol, an imidazopyridine, an imidazopyrimidine, an azacarbazole, but is not limited thereto.

For example, the electron transport region may include Compounds represented by Formula 601.

$$[Ar_{601}]_{xe11}\text{-}[(L_{601})_{xe1}\text{-}R_{601}]_{xe21}. \quad <\text{Formula 601}>$$

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2 or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group and a substituted, or unsubstituted divalent non-aromatic condensed heteropolycyclic group, xe1 may be an integer of 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), wherein $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer of 1 to 5.

In one embodiment, at least one of xe11 $Ar_{601}$(s) and xe21 $R_{601}$(s) may include the above-described it electron-depleted nitrogen-containing ring.

In one embodiment, the ring $Ar_{601}$ in Formula 601 may be selected from: a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, phenanthroline group, a phenazine group, a benzoimidazole group, an iso-benzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzoimidazole group, an iso-benzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more $Ar_{60i}$(s) may be linked with each other through a single bond.

In some embodiments, $Ar_{601}$ in Formula 601 may be an anthracene group.

In some embodiments, a compound represented by Formula 601 may be represented by Formula 601-1:

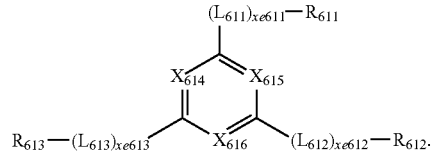

<Formula 601-1>

In Formula 601-1, $X_{614}$ may be N or $C(R_{614})$, $X_{615}$ may be N or $C(R_{615})$, $X_{616}$ may be N or $C(R_{616})$, and at least one of $X_{614}$ to $X_{616}$ may be N, $L_{611}$ to $L_{613}$ may each independently the same as described in connection with $L_{601}$, xe611 to xe613 may each independently the same as described in connection with xe1, $R_{611}$ to $R_{613}$ may each independently the same as described in connection with $R_{601}$, $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from: a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzoimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzoimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but are not limited thereto.

In some embodiments, xe1 and xe611 to xe613 in Formulae 601 and 601-1 may each independently be 0, 1 or 2.

In some embodiments, $R_{601}$ and $R_{611}$ to $R_{613}$ in Formulae 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), wherein Q$_{601}$ and Q$_{602}$ may be the same as described above.

The electron transport region may include at least one compound selected from Compounds ET1 to ET36, but is not limited thereto:

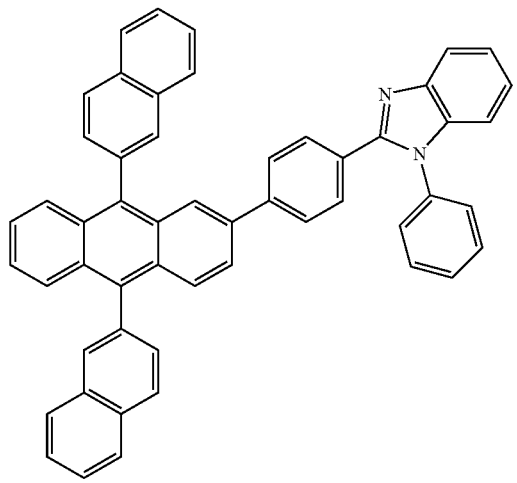

ET1

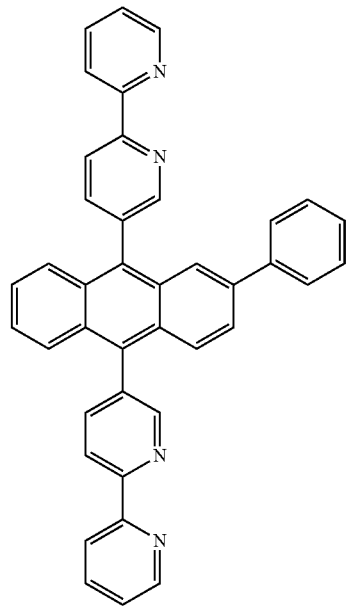

ET2

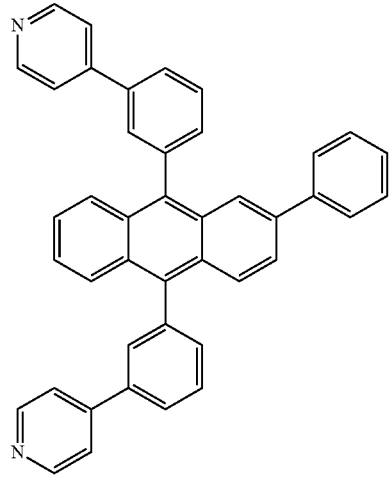

ET3

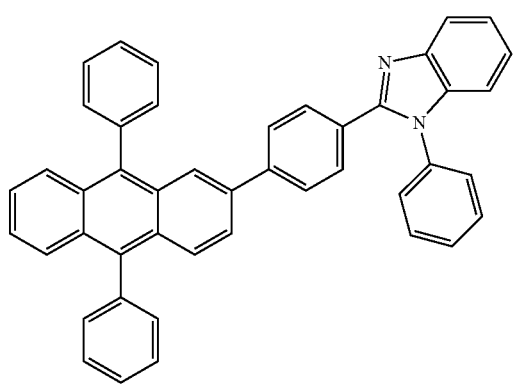
ET4
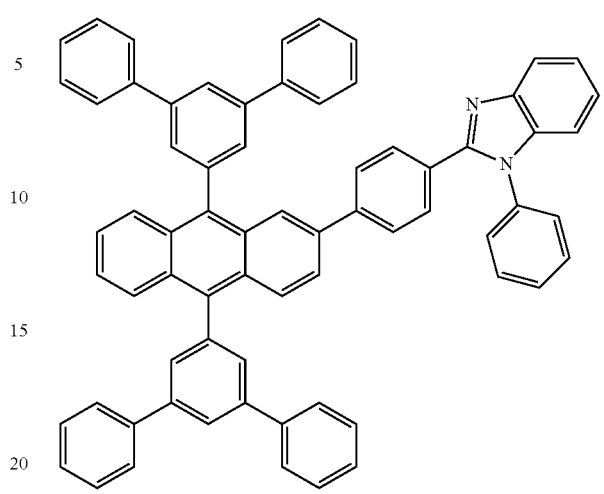
ET7
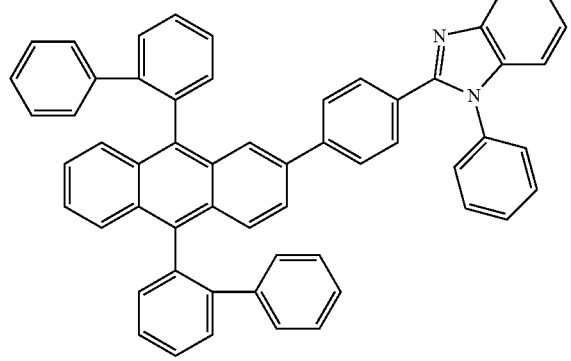
ET5
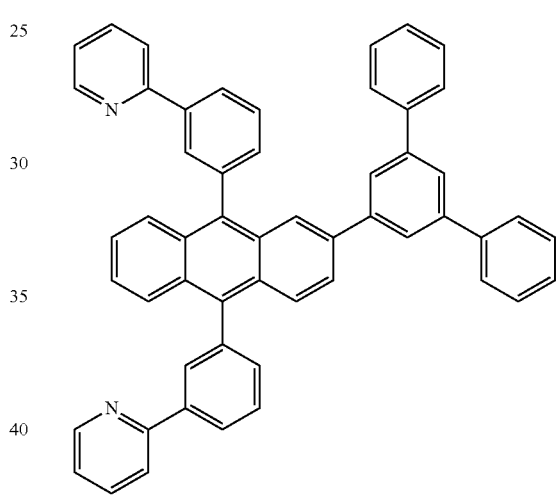
ET8
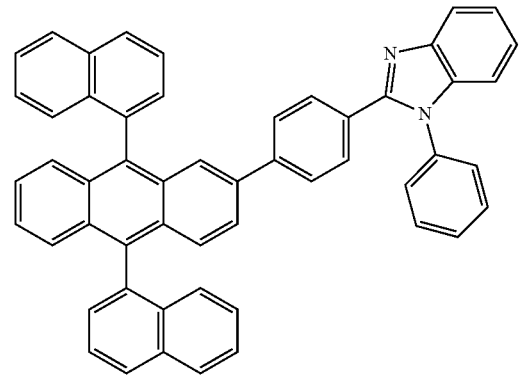
ET6
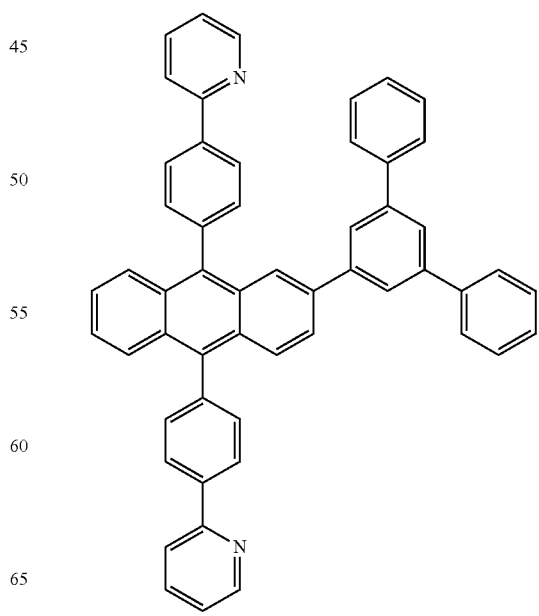
ET9

ET10
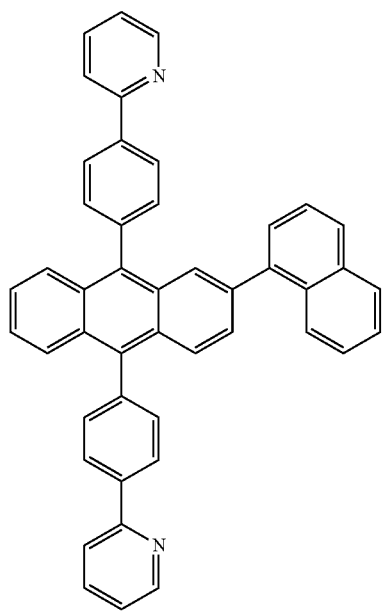
ET11
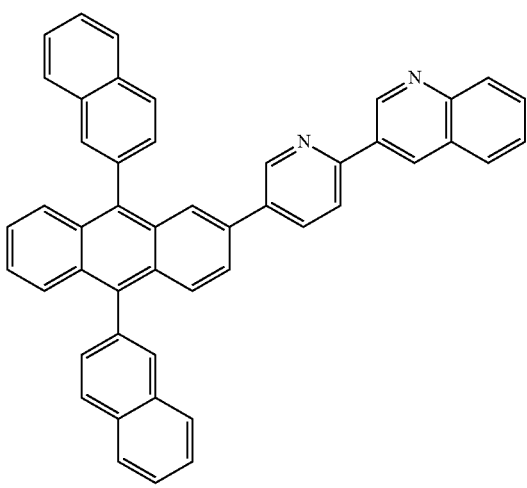
ET12
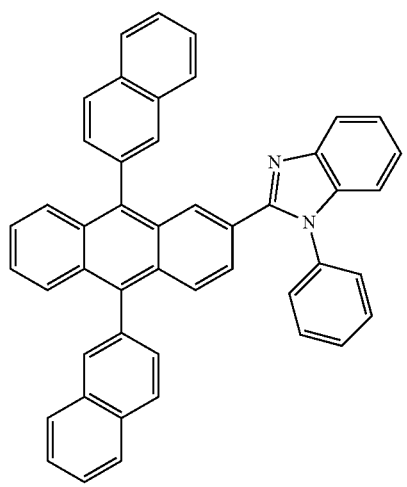
ET13
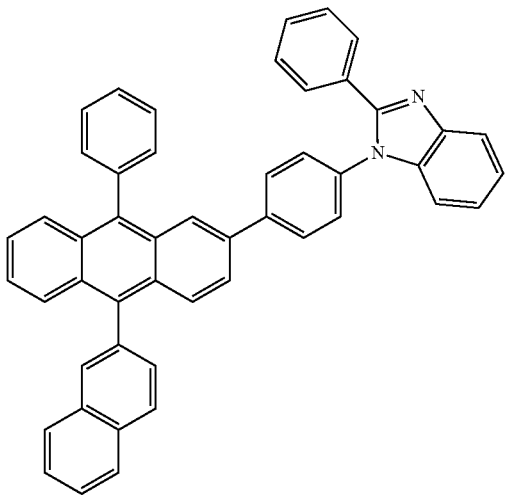
ET14
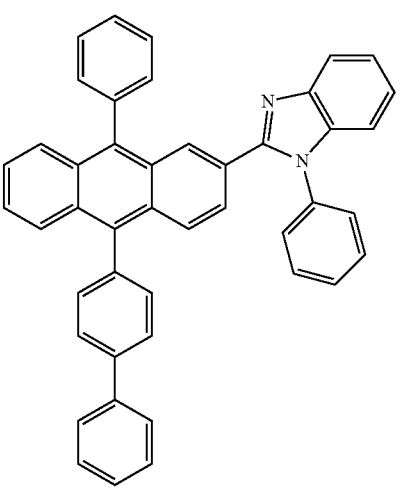
ET15
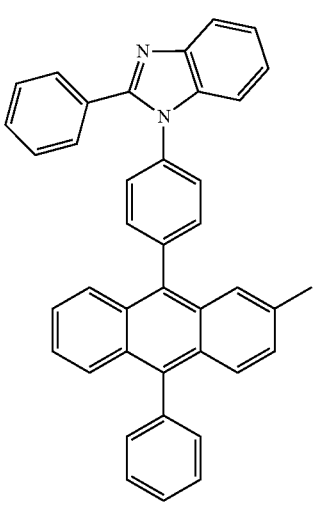

ET16
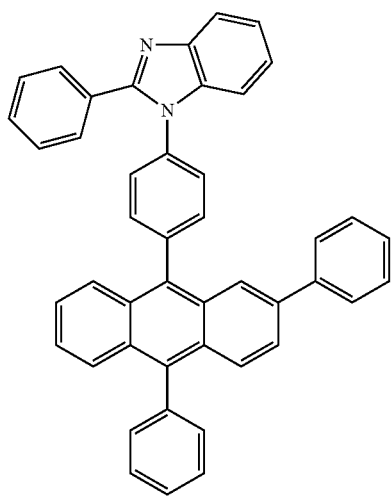
ET17
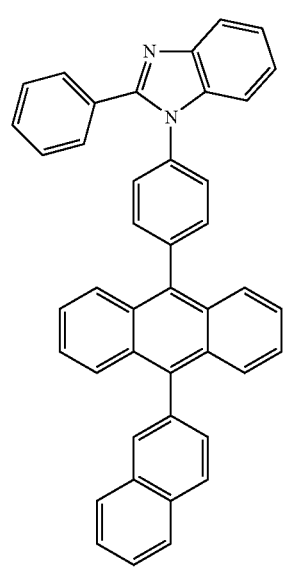
ET18
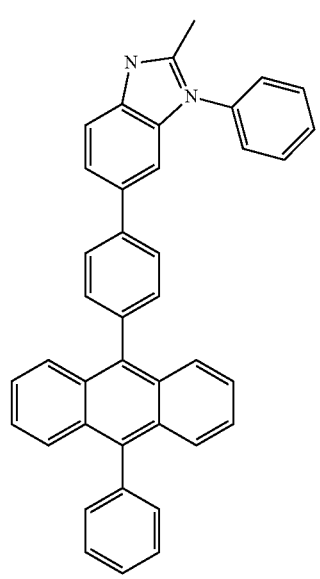
ET19
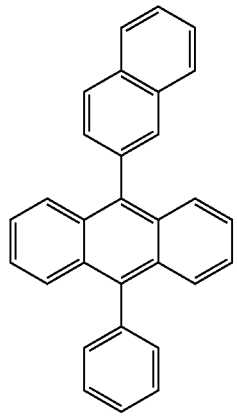
ET20
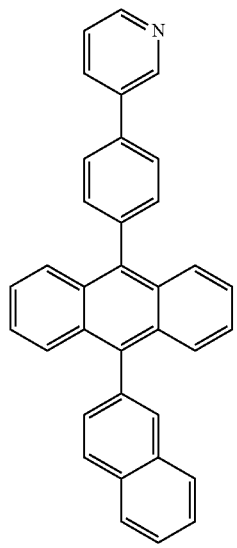
ET21
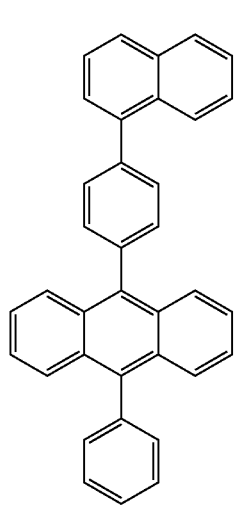

ET22
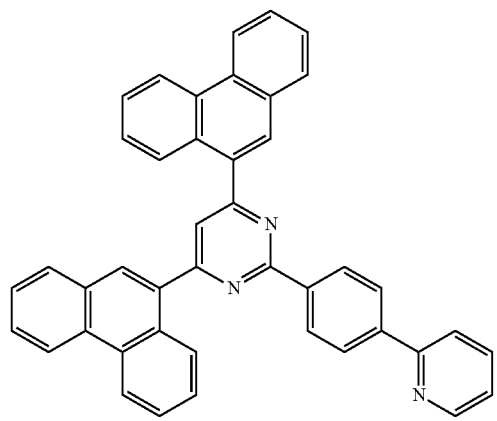
ET25
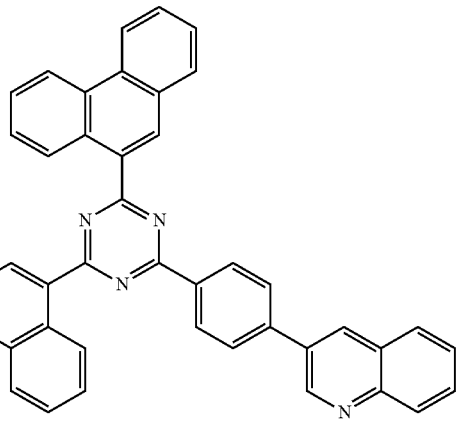
ET23
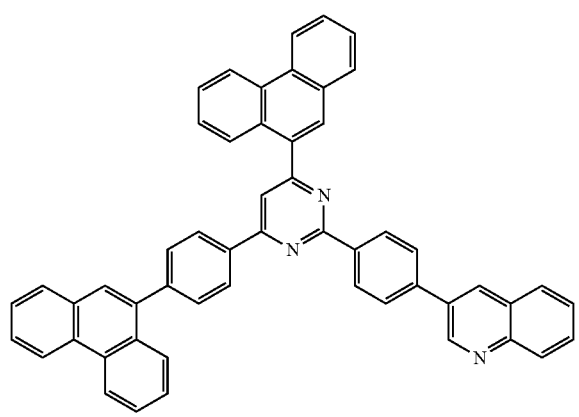
ET26
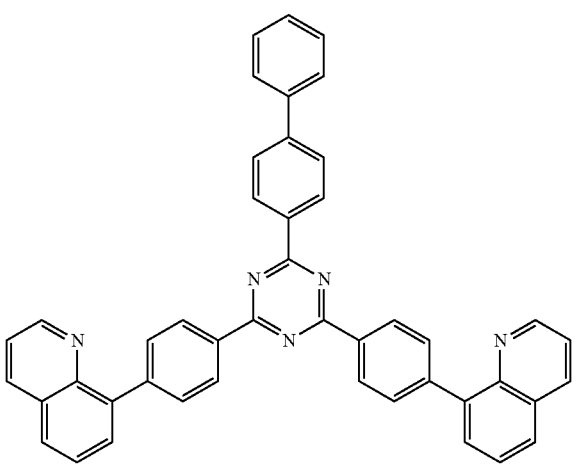
ET24
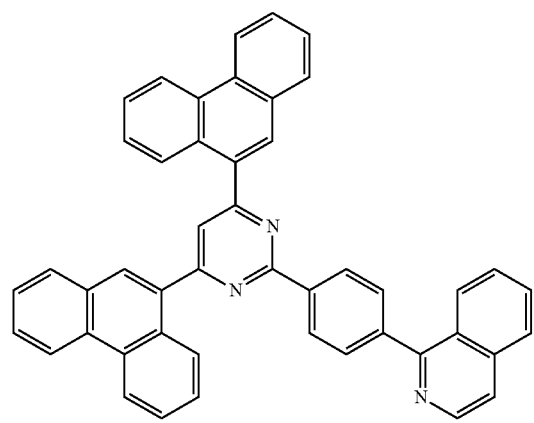
ET27
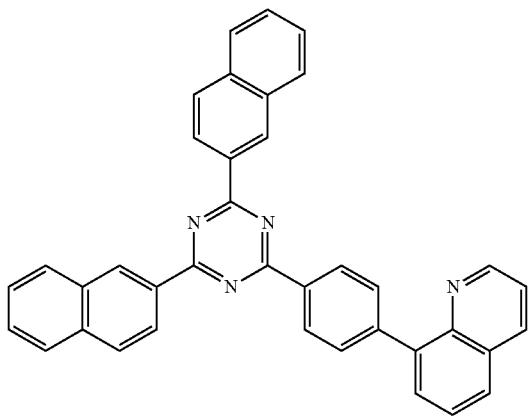

ET28
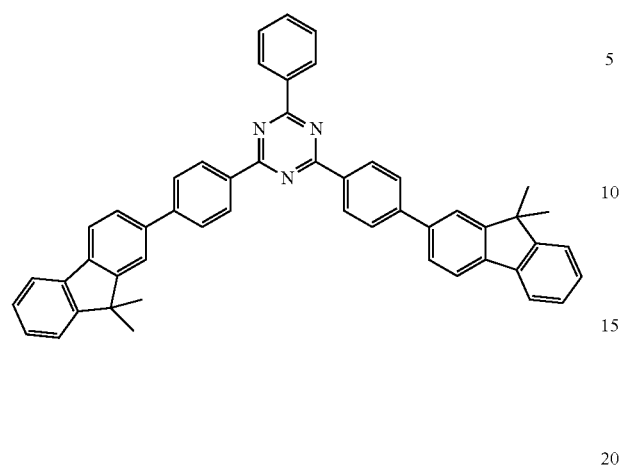
ET29
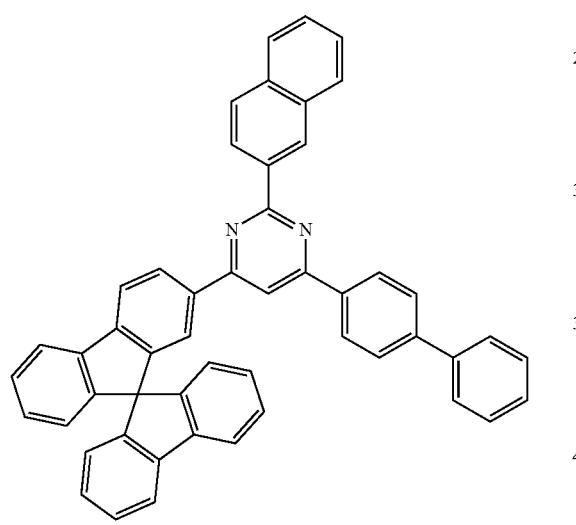
ET30
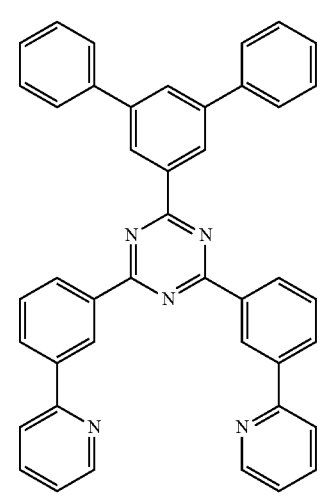
ET31
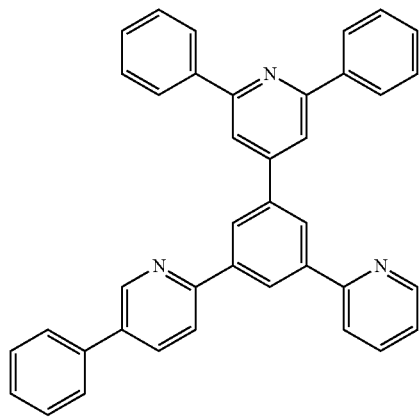
ET32
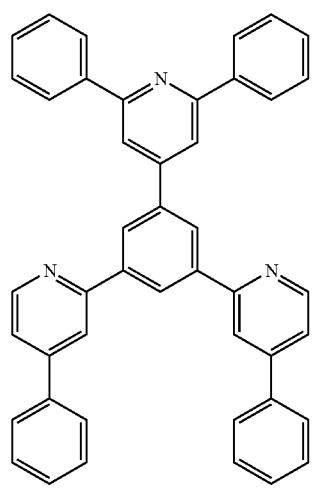
ET33
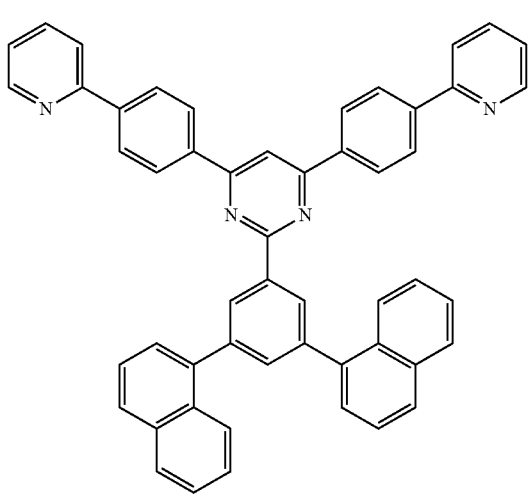

ET34

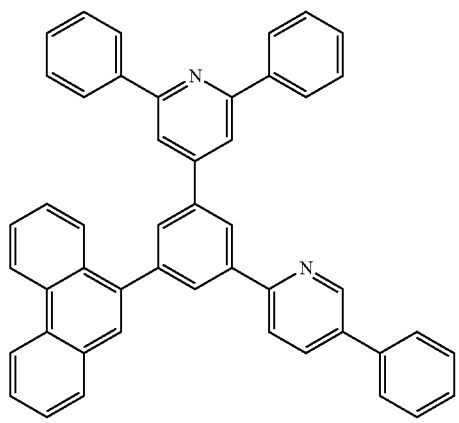

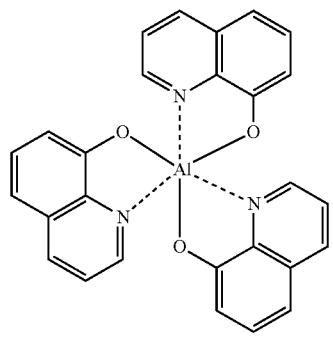

Alq₃

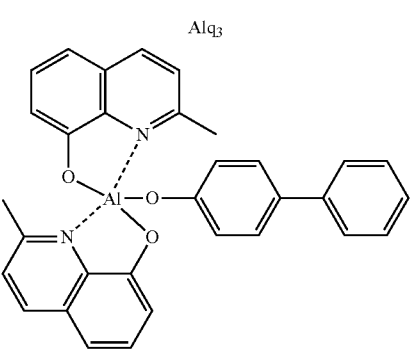

BAlq

ET35

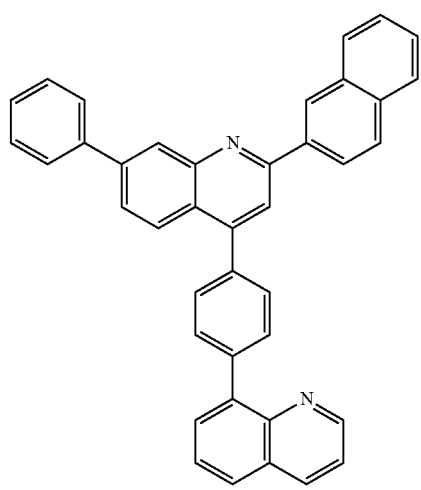

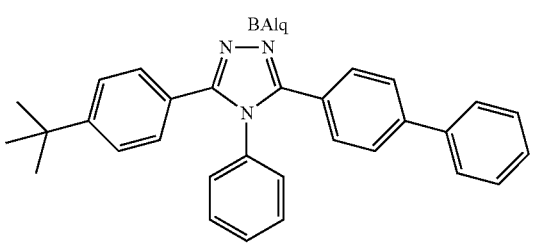

TAZ

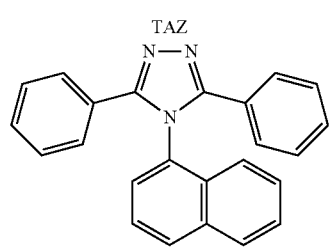

NTAZ

ET36

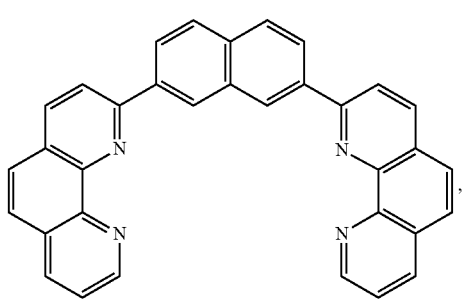

In some embodiments, the electron transport region may include at least one Compound selected from 2,9-dimethyl-4,7-diphenyl-1,10-phenanthroline (BCP), 4,7-diphenyl-1,10-phenanthroline (Bphen), Alq₃, BAlq, 3-(Biphenyl-4-yl)-5-(4-tert-butylphenyl)-4-phenyl-4H-1,2,4-triazole (TAZ), and NTAZ.

Thicknesses of the buffer layer, the hole blocking layer, or the electron controlling layer may each independently be from about 20 Å to about 1,000 Å, for example, about 30 Å to about 300 Å. When the thicknesses of the buffer layer, the hole blocking layer, or the electron controlling layer are within these ranges, excellent hole blocking characteristics or electron controlling characteristics may be obtained without a substantial increase in driving voltage.

A thickness of the electron transport layer may be from about 100 Å to about 1000 Å, for example, about 150 Å to about 500 Å. When the thickness of the electron transport layer is within the range described above, the electron transport layer may have satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from alkaline metal complex and alkaline earth-metal complex. The alkaline metal complex may include a metal ion selected from an Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkaline metal complex or the alkaline earth-metal complex may each independently selected from a hydroxy quinoline, a hydroxy isoquinoline, a hydroxy benzoquinoline, a hydroxy acridine, a hydroxy phenanthridine, a hydroxy phenyl oxazole, a hydroxy phenylthiazole, a hydroxy diphenyl oxadiazole, a hydroxy diphenylthiadiazole, a hydroxy phenylpyridine, a hydroxy phenylbenzoimidazole, a hydroxy phenylbenzothiazole, a bipyridine, a phenanthroline, and a cyclopentadiene, but is not limited thereto.

For example, the metal-containing material may include a Li complex. The Li complex may include, for example, Compound ET-D1 (lithium 8-hydroxyquinolate, LiQ) or ET-D2.

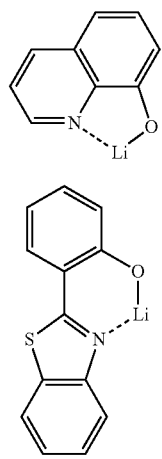

The electron transport region may include an electron injection layer that facilitates injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include alkali metal, alkaline earth metal, rare-earth-metal, alkaline metal compound, alkaline earth-metal compound, rare-earth metal compound, alkaline metal complex, alkaline earth-metal complex, rare-earth metal complex or any combinations thereof.

The alkaline metal may be selected from Li, Na, K, Rb, and Cs. In one embodiment, the alkaline metal may be Li, Na, or Cs. In some embodiments, the alkaline metal may be Li or Cs, but is not limited thereto.

The alkaline earth metal may be selected from Mg, Ca, Sr, and Ba.

The rare-earth metal may be selected from Sc, Y, Ce, Tb, Yb, Gd, and Tb.

The alkaline metal compound, the alkaline earth-metal compound, and the rare-earth metal compound may be selected from oxides and halides (for example, fluorides, chlorides, bromides, or iodides) of the alkali metal, the alkaline earth-metal and rare-earth metal.

The alkaline metal compound may be selected from alkaline metal oxides, such as $Li_2O$, $Cs_2O$, or $K_2O$, and alkaline metal halides, such as LiF, NaF, CsF, KF, LiI, NaI, CsI, or KI. In one embodiment, the alkaline metal compound may be selected from LiF, $Li_2O$, NaF, LiI, NaI, CsI, and KI, but is not limited thereto.

The alkaline earth-metal compound may be selected from alkaline earth-metal oxides, such as BaO, SrO, CaO, $Ba_xSr_{1-3}O(0<x<1)$, or $Ba_xCa_{1-x}O(0<x<1)$. In one embodiment, the alkaline earth-metal compound may be selected from BaO, SrO, and CaO, but is not limited thereto.

The rare-earth metal compound may be selected from $YbF_3$, $ScF_3$, $ScO_3$, $Y_2O_3$, $Ce_2O_3$, $GdF_3$, and $TbF_3$. In one embodiment, the rare-earth metal compound may be selected from $YbF_3$, $ScF_3$, $TbF_3$, $YbI_3$, $ScI_3$, and $TbI_3$, but is not limited thereto.

The alkaline metal complex, the alkaline earth-metal complex, and the rare-earth metal complex may include an ion of alkali metal, alkaline earth-metal, and rare-earth metal as described above, and a ligand coordinated with a metal ion of the alkaline metal complex, the alkaline earth-metal complex, and the rare-earth metal complex may each independently be selected from hydroxy quinoline, hydroxy isoquinoline, hydroxy benzoquinoline, hydroxy acridine, hydroxy phenanthridine, hydroxy phenyl oxazole, hydroxy phenylthiazole, hydroxy diphenyl oxadiazole, hydroxy diphenylthiadiazole, hydroxy phenylpyridine, hydroxy phenylbenzoimidazole, hydroxy phenylbenzothiazole, bipyridine, and a phenanthroline and cyclopentadiene, but is not limited thereto.

The electron injection layer may include only alkali metal, alkaline earth metal, rare-earth-metal, alkaline metal compound, alkaline earth-metal compound, rare-earth metal compound, alkaline metal complex, alkaline earth-metal complex, rare-earth metal complex or any combinations thereof, as described above. In some embodiments, the electron injection layer may further include an organic material. When the electron injection layer further includes an organic material, alkali metal, alkaline earth metal, rare-earth-metal, alkaline metal compound, alkaline earth-metal compound, rare-earth metal compound, alkaline metal complex, alkaline earth-metal complex, rare-earth metal complex, or any combinations thereof may be homogeneously or non-homogeneously dispersed in a matrix including the organic material.

A thickness of the electron injection layer may be from about 1 Å to about 100 Å, for example, about 3 Å to about 90 Å. When the thickness of the electron injection layer is within the range described above, the electron injection layer may have satisfactory electron injection characteristics without a substantial increase in driving voltage.

[Second Electrode 190]

The second electrode 190 may be disposed on the organic layer 150 having such a structure. The second electrode 190 may be a cathode that is an electron injection electrode, and in this regard, a material for forming the second electrode 190 may be a material having a low work function, and such a material may be metal, alloy, an electrically conductive compound, or a mixture thereof.

The second electrode 190 may include at least one selected from lithium (Li), silver (Si), magnesium (Mg), aluminum (Al), aluminum-lithium (Al—Li), calcium (Ca), magnesium-indium (Mg—In), magnesium-silver (Mg—Ag), ITO, and IZO, but is not limited thereto. The second electrode 190 may be a transmissive electrode, a semi-transmissive electrode, or a reflective electrode.

The second electrode 190 may have a single-layer structure, or a multi-layer structure including two or more layers.

Figure 3:
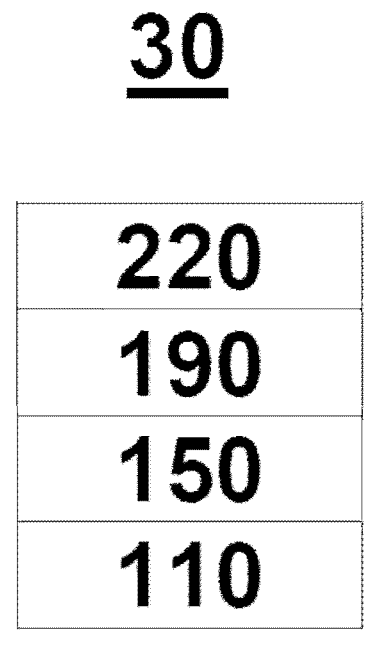
Figure 4:
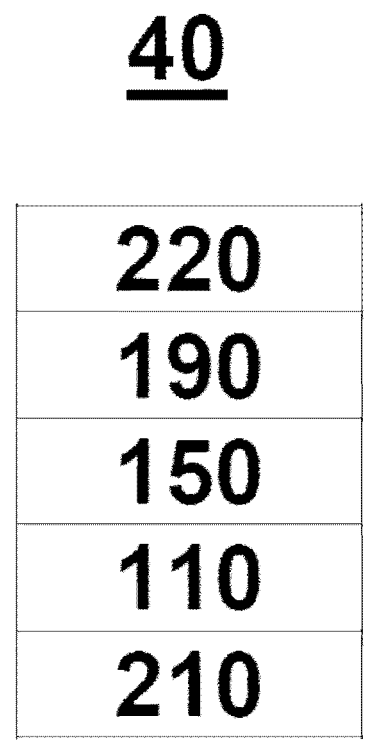

[Description of FIGS. 2 to 4]

Figure 2:
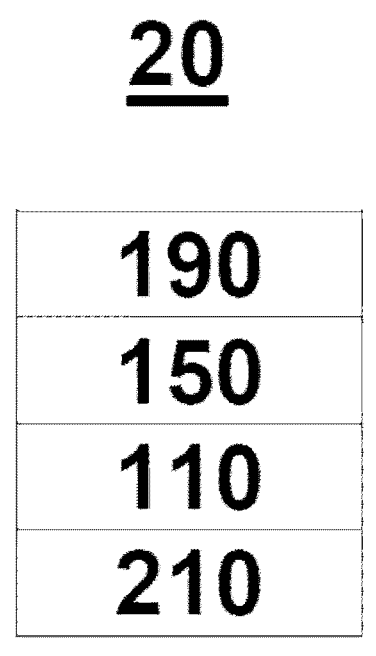

An organic light-emitting device 20 of FIG. 2 includes a first capping layer 210, a first electrode 110, an organic layer 150, and a second electrode 190 which are sequentially stacked in this stated order, an organic light-emitting device 30 of FIG. 3 includes a first electrode 110, an organic layer 150, a second electrode 190, and a second capping layer 220 which are sequentially stacked in this stated order, and an organic light-emitting device 40 of FIG. 4 includes a first capping layer 210, a first electrode 110, an organic layer 150, a second electrode 190, and a second capping layer 220.

Regarding FIGS. 2 to 4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110, which is a semi-transmissive electrode or a transmissive electrode, and the first capping layer 210 toward the outside, and in the organic layer 150 of each of the organic light-emitting devices 30 and 40, light generated in an emission layer may pass through the second electrode 190, which is a semi-transmissive electrode or a transmissive electrode, and the second capping layer 220 toward the outside.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphine derivatives, phthalocyanine derivatives, naphthalocyanine derivatives, alkaline metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I. In one embodiment, at least one selected from the first capping layer 210 and the second capping layer 220 may each independently include an amine-based compound.

In one embodiment, at least one selected from the first capping layer 210 and the second capping layer 220 illustrated in FIG. 4 may include the condensed cyclic compound represented by Formula 1.

In one embodiment, at least one selected from the first capping layer 210 and the second capping layer 220 may each independently include the compound represented by Formula 201 or the compound represented by Formula 202.

In some embodiments, at least one selected from the first capping layer 210 and the second capping layer 220 may each independently include a compound selected from Compounds HT28 to HT33 and Compounds CP1 to CP5, but is not limited thereto.

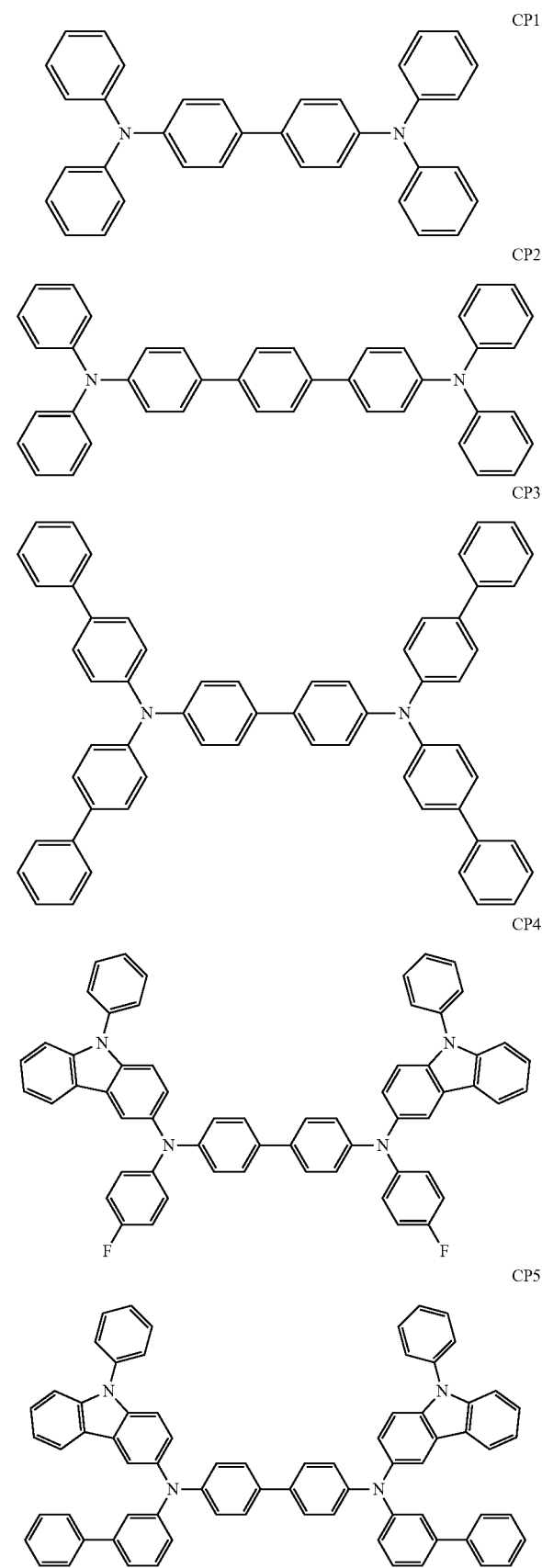 [SMILES: c1ccc(N(c2ccccc2)c2ccc(-c3ccc(N(c4ccccc4)c4ccccc4)cc3)cc2)cc1 ; c1ccc(N(c2ccccc2)c2ccc(-c3ccc(-c4ccc(N(c5ccccc5)c5ccccc5)cc4)cc3)cc2)cc1 ; c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1 ; Fc1ccc(N(c2ccc(-c3ccc(N(c4ccc(F)cc4)c4ccc5c(c4)c4ccccc4n5-c4ccccc4)cc3)cc2)c2ccc3c(c2)c2ccccc2n3-c2ccccc2)cc1 ; c1ccc(-c2cccc(N(c3ccc(-c4ccc(N(c5cccc(-c6ccccc6)c5)c5ccc6c(c5)c5ccccc5n6-c5ccccc5)cc4)cc3)c3ccc4c(c3)c3ccccc3n4-c3ccccc3)c2)cc1]

Hereinbefore, the organic light-emitting device according to an embodiment has been described in connection with FIGS. 1-4. However, embodiments are not limited thereto.

Layers constituting the hole transport region, an emission layer, and layers constituting the electron transport region may be formed in a certain region by using one or more suitable methods selected from vacuum deposition, spin coating, casting, a langmuir-blodgett (LB) deposition, ink-jet printing, laser-printing, and laser-induced thermal imaging.

When the respective layers of the hole transport region, the emission layer, and the respective layers of the electron transport region are formed by deposition, the deposition may be performed at a deposition temperature of about 100 to about 500° C., at a vacuum degree of about $10^{-8}$ to about $10^{-3}$ torr, and at a deposition rate of about 0.01 to about 100 Å/sec by taking into account a compound for forming a layer to be deposited, and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to 200° C. by taking into account a compound to be included in a to-be-formed layer, and the structure of a to-be-formed layer.

[General Definition of Substituents]

The term "$C_1$-$C_{60}$ alkyl group," as used herein, refers to a linear or branched aliphatic saturated hydrocarbon monovalent group having 1 to 60 carbon atoms, and non-limiting examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group," as used herein, refers to a divalent group having the same structure as the $C_1$-$C_{60}$ alkyl group.

The term "$C_2$-$C_{60}$ alkenyl group," as used herein, refers to a hydrocarbon group formed by substituting at least one carbon-carbon double bond in the middle or at the terminal of the $C_2$-$C_{60}$ alkyl group, and non-limiting examples thereof include an ethenyl group, a propenyl group, and a butenyl group. The term "$C_2$-$C_{60}$ alkenylene group," as used herein, refers to a divalent group having the same structure as the $C_2$-$C_{60}$ alkenyl group.

The term "$C_2$-$C_{60}$ alkynyl group," as used herein, refers to a hydrocarbon group formed by substituting at least one carbon trip bond in the middle or at the terminal of the $C_2$-$C_{60}$ alkyl group, and non-limiting examples thereof include an ethynyl group, and a propynyl group. The term "$C_2$-$C_{60}$ alkynylene group," as used herein, refers to a divalent group having the same structure as the $C_2$-$C_{60}$ alkynyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and non-limiting examples thereof include a methoxy group, an ethoxy group, and an isopropyloxy group.

The term "$C_3$-$C_{10}$ cycloalkyl group," as used herein, refers to a monovalent hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having the same structure as the $C_3$-$C_{10}$ cycloalkyl group.

The term "$C_{10}$-$C_{10}$ heterocycloalkyl group," as used herein, refers to a monovalent saturated monocyclic group having at least one heteroatom selected from N, O, Si, P, and S as a ring-forming atom and 1 to 10 carbon atoms, and non-limiting examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having the same structure as the $C_1$-$C_{10}$ heterocycloalkyl group.

The term "$C_3$-$C_{10}$ cycloalkenyl group," as used herein, refers to a monovalent monocyclic group that has 3 to 10 carbon atoms and at least one double bond in the ring thereof and does not have aromaticity, and non-limiting examples thereof include a cyclopentenyl group, a cyclohexenyl group, and a cycloheptenyl group. The term "$C_3$-$C_{10}$ cycloalkenylene group," as used herein, refers to a divalent group having the same structure as the $C_3$-$C_{10}$ cycloalkenyl group.

The term "$C_1$-$C_{10}$ heterocycloalkenyl group," as used herein, refers to a monovalent monocyclic group that has at least one heteroatom selected from N, O, Si, P, and S as a ring-forming atom, 1 to 10 carbon atoms, and at least one double bond in its ring. Non-limiting examples of the $C_1$-$C_{10}$ heterocycloalkenyl group are a 4,5-dihydro-1,2,3,4-oxatriazolyl group, a 2,3-dihydrofuranyl group and a 2,3-dihydrothiophenyl group. The term "$C_1$-$C_1°$ heterocycloalkenylene group," as used herein, refers to a divalent group having the same structure as the $C_1$-$C_1°$ heterocycloalkenyl group.

The term "$C_6$-$C_{60}$ aryl group," as used herein, refers to a monovalent group having a carbocyclic aromatic system having 6 to 60 carbon atoms, and the term "$C_6$-$C_{60}$ arylene group," as used herein, refers to a divalent group having a carbocyclic aromatic system having 6 to 60 carbon atoms. Non-limiting examples of the $C_{60}$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group," as used herein, refers to a monovalent group having a heterocyclic aromatic system that has at least one heteroatom selected from N, O, Si, P, and S as a ring-forming atom, and 1 to 60 carbon atoms. The term "$C_1$-$C_{60}$ heteroarylene group," as used herein, refers to a divalent group having a heterocyclic aromatic system that has at least one heteroatom selected from N, O, Si, P, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group," as used herein, refers to —$OA_{102}$ (wherein $A_{102}$ is the $C_6$-$C_{60}$ aryl group), and a $C_6$-$C_{60}$ arylthio group used herein indicates -$SA_{103}$ (wherein $A_{103}$ is the $C_6$-$C_{60}$ aryl group).

The term "monovalent non-aromatic condensed polycyclic group," as used herein, refers to a monovalent group (for example, having 8 to 60 carbon atoms) that has two or more rings condensed with each other, only carbon atoms as a ring forming atom, and non-aromaticity in the entire molecular structure. A detailed example of the monovalent non-aromatic condensed polycyclic group is a fluorenyl group. The term "divalent non-aromatic condensed polycyclic group," used herein, refers to a divalent group having the same structure as the monovalent non-aromatic condensed polycyclic group.

The term "monovalent non-aromatic condensed heteropolycyclic group," as used herein, refers to a monovalent group (for example, having 1 to 60 carbon atoms) that has two or more rings condensed to each other, has at least one heteroatom selected from N, O, Si, P, and S, other than carbon atoms, as a ring forming atom, and has non-aromaticity in the entire molecular structure. An example of the monovalent non-aromatic condensed heteropolycyclic group is a carbazolyl group. The term "divalent non-aromatic condensed heteropolycyclic group," used herein, refers to a divalent group having the same structure as the monovalent non-aromatic condensed heteropolycyclic group.

The term "$C_5$-$C_{60}$ carbocyclic group," as used herein, refers to a monocyclic or polycyclic group having 5 to 60 carbon atoms in which a ring-forming atom is a carbon atom only. The term "$C_5$-$C_{60}$ carbocyclic group," as used herein refers to an aromatic carbocyclic group or a non-aromatic carbocyclic group. The term "$C_5$-$C_{60}$ carbocyclic group," as used herein, refers to a ring, such as a benzene, a monovalent group, such as a phenyl group, or a divalent group, such as a phenylene group. In some embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group," as used herein, refers to a group having the same structure as the $C_1$-$C_{60}$ carbocyclic group, except that as a ring-forming atom, at least one heteroatom selected from N, O, Si, P, and S is used in addition to carbon (the number of carbon atoms may be from 1 to 60).

At least one substituent of the substituted $C_5$-$C_{60}$ carbocyclic group, substituted $C_1$-$C_{60}$ heterocyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, a substituted divalent non-aromatic condensed polycyclic group, a substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group may be selected from deuterium(-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —SW$_{21}$($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=o)($Q_{31}$), —S(=O)$_2$($Q_{31}$) and —P(=O)($Q_{31}$)($Q_{32}$), wherein $Q_{11}$ to $Q_{13}$, $Q_{21}$ to $Q_{23}$ and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph", as used herein, may refer to a phenyl group; the term "Me", as used herein, may refer to a methyl group; the term "Et", as used herein, may refer to an ethyl group; the terms "ter-Bu" or "But", as used herein, may refer to a tert-butyl group; and the term "OMe," as used herein refers to a methoxy group.

The "biphenyl group" used therein refers to "a phenyl group substituted with a phenyl group." The "biphenyl group" belongs to "a substituted phenyl group" having "a $C_6$-$C_{60}$ aryl group" as a substituent.

The "terphenyl group" used herein refers to "a phenyl group substituted with a biphenyl group." The "terphenyl group" belongs to "a substituted phenyl group" having "a $C_6$-$C_{60}$ aryl group substituted with a $C_6$-$C_{60}$ aryl group."

Symbols * and *' used herein, unless defined otherwise, refer to a binding site to a neighboring atom in a corresponding formula.

Hereinafter, a compound according to embodiments and an organic light-emitting device according to embodiments will be described in detail with reference to Synthesis Examples and Examples. The wording "B was used instead of A" used in describing Synthesis Examples means that a molar equivalent of A was identical to a molar equivalent of B.

EXAMPLE

Synthesis Example 1: Synthesis of Compound 1

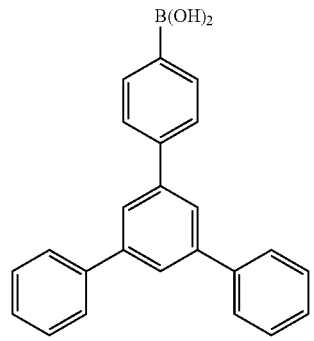

+

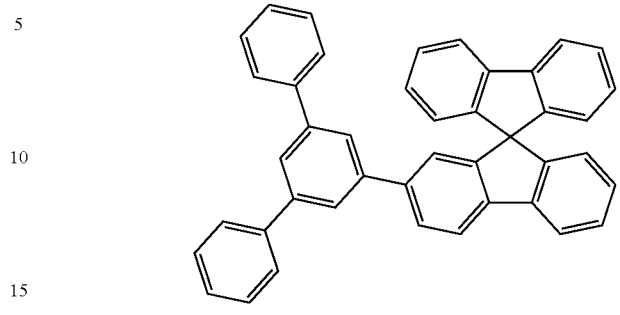

Compound 1

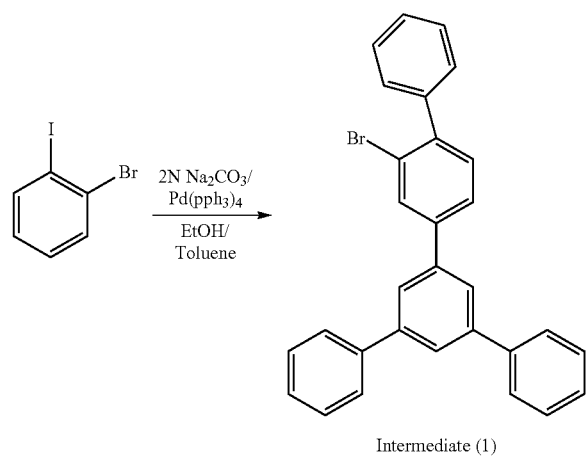

Intermediate (1)

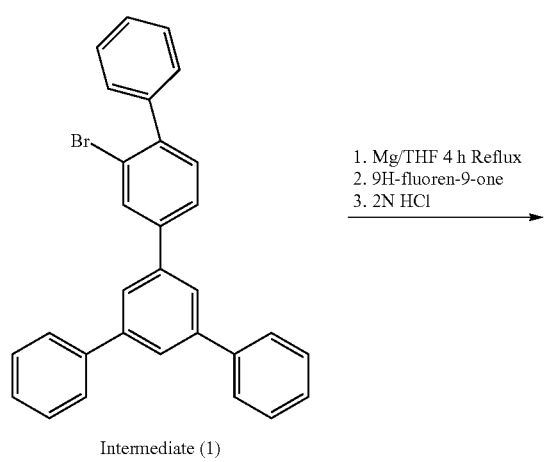

Intermediate (1)

Synthesis of Intermediate (1)

3 g (0.009 mol) of (5'-phenyl-[1,1':3',1''-terphenyl]-4-yl) boronic acid and 2.42 g (0.009 mol) of 1-bromo-2-iodobenzene were added to 100 ml of a 3-neck flask, and 3 ml of 2N $Na_2CO_3$ and a mixed solution including toluene and EtOH were added thereto. Oxygen was removed from the mixture while stirring. Then, nitrogen substitution was performed thereon, and 0.5 g of catalyst $Pd(pph_3)_4$ was added thereto and refluxed at a temperature of 110° C. for 8 hours. The reaction was stopped by using water, and an extraction process was performed three times by using methylene chloride (MC), and then, a solvent was removed therefrom. The result was subjected to column chromatography by using a solvent including ethyl acetate (EA): hexane (Hex) at a ratio of 1:5 to complete the preparation of 2.1 g (51%) of Intermediate (1).

H-NMR ($CDCl_3$): 8.01 (3H, s), 7.85-7.80 (3H, d), 7.59-7.35 (9H, m), 7.21-7.05 (6H, m)

Synthesis of Compound 1

0.12 g (0.005 mol) of Mg was added to a 3-neck flask, and a solution prepared by dissolving 2.1 g (0.005 mol) of Intermediate (1) in THF was slowly added dropwise to the 3-neck flask, and the resultant solution was refluxed at a temperature of 80° C. for 4 hours. Thereafter, the result was dissolved in 0.8 g (0.005 mol) of 9H-fluorene-9-one in a 3-neck flask and a completed Grignard reagent was slowly added thereto, and a reaction was performed overnight. Then, 2N HCl was used to stop the reaction, and the pH of the reaction solution was adjusted to be 7, and then, an extraction process was performed thereon three times by using MC. Then, a solvent was removed therefrom, and column chromatography was performed thereon by using a solvent including EA and Hex at a ratio of 1:5 to obtain 1.8 g (66%) of Compound 1. H-NMR ($CDCl_3$): 7.99 (5H, s), 7.89 (2H, d), 7.66-7.61 (9H, m), 7.59-7.35 (6H, m), 7.21-7.05 (6H, m)

Synthesis Example 2: Synthesis of Compound 2

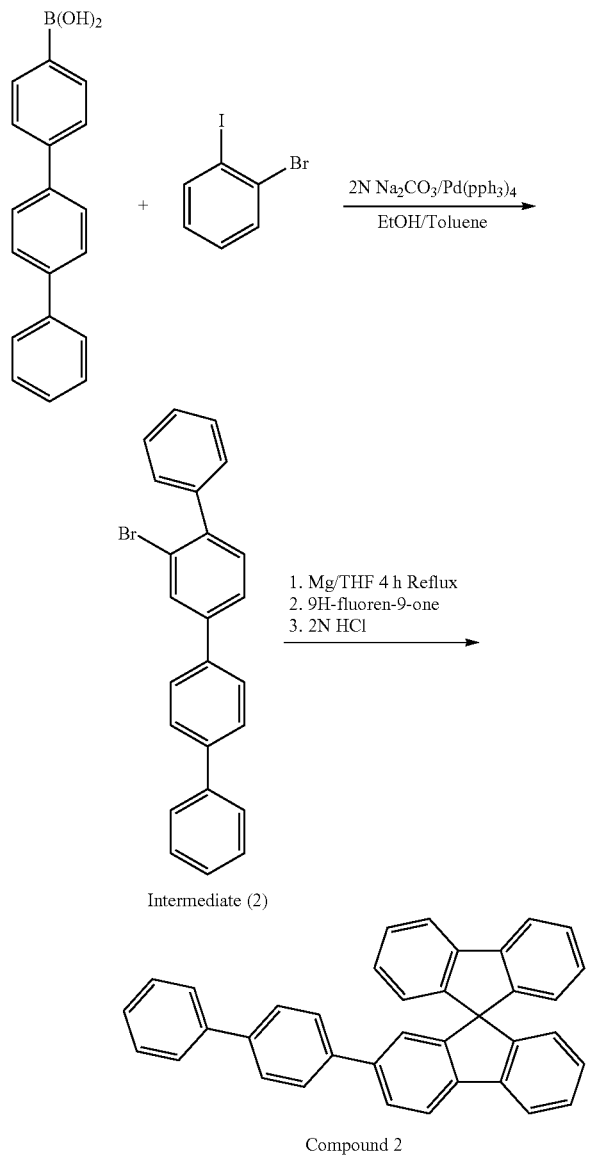

Compound 2

Synthesis of Intermediate (2)

3 g (0.011 mol) of [1,1':4',1''-terphenyl]-4-ylboronic acid and 3.1 g (0.011 mol) of 1-bromo-2-iodobenzene were added to 100 ml of a 3-neck flask, and 3 ml of 2N $Na_2CO_3$ and a mixed solution including toluene and EtOH were added thereto. Oxygen was removed from the mixture while stirring. Nitrogen substitution was performed thereon, and 0.5 g of catalyst $Pd(pph_3)_4$ was added thereto, and the result was refluxed at a temperature of 110° C. for 8 hours. Then, the reaction was stopped by using water, and then, an extraction process was performed thereon three times by using MC, and a solvent was removed from the result. The result was subjected to column chromatography by using a solvent including EA and Hex at a ratio of 1:5 to obtain 2.5 g (59%) of Intermediate (2).

H-NMR (CDCl3): 7.85 (1H, d), 7.64 (4H, m), 7.49-7.38 (6H, m), 7.20-7.05 (6H, m)

Synthesis of Compound 2

0.3 g (0.012 mol) of Mg was added to a 3-neck flask, and a solution prepared by dissolving 2.5 g (0.006 mol) of Intermediate (2) in THF was slowly added dropwise to the 3-neck flask, and the resultant solution was refluxed at a temperature of 80° C. for 4 hours. The mixture was dissolved in 1.08 g (0.012 mol) of 9H-fluoren-9-one in a 3 neck flask, and then, a completed Grignard reagent was slowly added thereto, and a reaction was performed overnight. The reaction was stopped by using 2N HCl, and a pH of the result was adjusted to be 7, and then, an extraction process was performed thereon three times by using MC. A solvent was removed from the resultant product, and then column chromatography was performed thereon by using a solvent including EA and Hex at a ratio of 1:5 to complete the preparation of 1.5 g (53%) of Compound 2.

H-NMR ($CDCl_3$): 7.81 (2H, d), 7.66-7.61 (12H, m), 7.59-7.35 (4H, m), 7.21-7.05 (6H, m)

Evaluation Example 1: Evaluation on HOMO, LUMO, and $T_1$ Energy Levels

HOMO, LUMO, and triplet ($T_1$) energy levels of Compound 1 and 2, mCP, Firpic, and Compound A were evaluated by using the methods shown in Table 2, and results thereof are shown in Table 3.

TABLE 2

| | |
|---|---|
| HOMO energy level evaluation method | A potential (V)-current (A) graph of each compound was obtained by using cyclic voltammetry (CV) (electrolyte: 0.1M $Bu_4NPF_6$/solvent: $CH_2Cl_2$/electrode: 3-electrode system (working electrode: Pt disc (in a diameter of 1 mm), reference electrode: Pt wire, auxiliary electrode: Pt wire)), and then, from reduction onset of the graph, a HOMO energy level of the compound was calculated. |
| LUMO energy level evaluation method | Each compound was diluted at a concentration of $1 \times 10^{-5}$M in $CHCl_3$, and an UV absorption spectrum thereof was measured at room temperature by using a shimadzu UV-350 spectrometer, and a LUMO energy level thereof was calculated by using an optical band gap (Eg) and HOMO energy levels from an edge of the absorption spectrum. |
| $T_1$ energy level evaluation method | A mixture (each compound was dissolved in an amount of 1 mg in 3 cc of toluene) of toluene and each compound was loaded into a quartz cell, and then, the resultant quartz cell was loaded into liquid nitrogen (77 K) and a photoluminescence spectrum thereof was measured by using a device for measuring photoluminescence, and the obtained spectrum was compared with a photoluminescence spectrum measured at room temperature, and peaks observed only at low temperature were analyzed to calculate $T_1$ energy levels. |

TABLE 3

| | HOMO (eV) (found) | LUMO (eV) (found) | $T_1$ (eV) (found) | Difference with respect to $T_1$ energy level of Firpic |
|---|---|---|---|---|
| Compound 1 | −6.1 | −2.8 | 2.82 | 0.12 |
| Compound 2 | −5.9 | −2.9 | 2.75 | 0.05 |
| mCP | −6.4 | −2.4 | 2.9 | 0.2 |
| Firpic | −5.8 | −3.2 | 2.7 | — |
| Compound A | — | — | 2.56 | 0.14 |

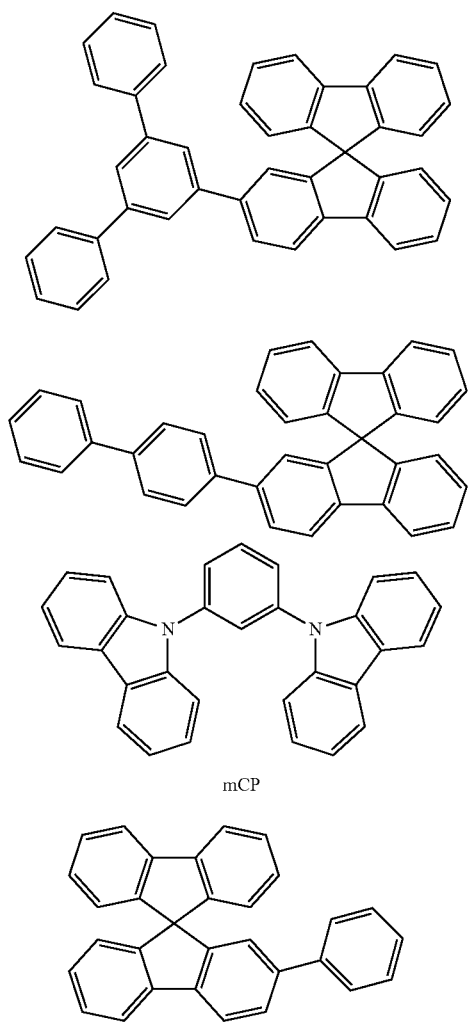

Example 1

As a substrate and an anode, a Corning 15 Ω/cm² (1,200 Å) ITO glass substrate was cut to a size of 50 mm×50 mm×0.7 mm, and then, sonicated with isopropyl alcohol and pure water, each for 5 minutes, and then washed by irradiation of ultraviolet ray for 30 minutes and ozone, and the resultant glass substrate was provided to a vacuum deposition apparatus.

2-TNATA was vacuum-deposited on the ITO anode to form a hole injection layer having a thickness of 600 Å, and 4,4'-bis[N-(1-naphthyl)-N-phenylamino]biphenyl (NPB) was vacuum-deposited on the hole injection layer to form a hole transport layer having a thickness of 300 Å.

Compound 1(host) and Firpic(dopant) were co-deposited on the hole transport layer at a weight ratio of 90:10 to form an emission layer having a thickness of 20 nm.

Compound ET1 was deposited on the emission layer to form an electron transport layer having a thickness of 300 Å, and LiF was deposited on the electron transport layer to form an electron injection layer having a thickness of 10 Å, and Al was vacuum-deposited on the electron injection layer to form a cathode having a thickness of 3,000 Å, thereby completing manufacture of an organic light-emitting device.

Examples 2 to 4 and Comparative Example 1

Organic light-emitting devices were manufactured in the same manner as in Example 1, except that in forming an emission layer, for use as a host, corresponding compounds shown in Table 4 were used instead of Compound 1 and a weight ratio for co-depositing of the host to the dopant shown in Table 4 were used.

Evaluation Example 2

The driving voltage, current density, luminance, and efficiency of the organic light-emitting devices manufactured according to Examples 1 to 4, and Comparative Examples 1 and 2 were measured by using Keithley SMU 236 and a brightness photometer PR650, and results thereof are shown in Table 4. Lifespan ($T_{90}$) data in Table 4 indicates an amount of time (hr) that lapsed when 100% of the initial luminance was decreased to 90%.

TABLE 4

| | Host | Dopant | Weight ratio of host to dopant | Driving voltage (V) | Current density (mA/cm²) | Efficiency (cd/A) | Lifespan ($T_{90}$) (time) |
|---|---|---|---|---|---|---|---|
| Example 1 | Compound 1 | Firpic | 90:10 | 5.22 | 5 | 20.4 | 40 |
| Example 2 | Compound 2 | Firpic | 80:20 | 5.21 | 5 | 23.3 | 62 |
| Example 3 | Compound 1 | Firpic | 90:10 | 5.18 | 5 | 21.5 | 52 |
| Example 4 | Compound 2 | Firpic | 80:20 | 5.16 | 5 | 24.5 | 77 |
| Comparative Example 1 | mCP | Firpic | 90:10 | 5.44 | 5 | 17.5 | 5 |
| Comparative Example 2 | mCP | Firpic | 80:20 | 5.42 | 5 | 19.2 | 15 |

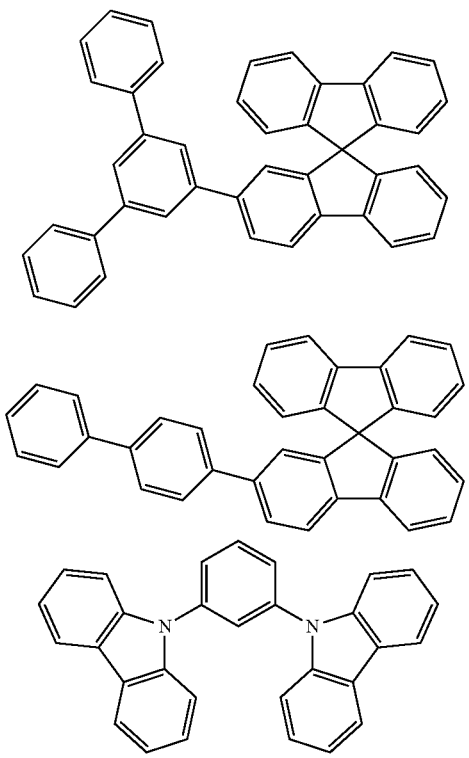

mCP

From Table 4, it is seen that the organic light-emitting devices of Examples 1 to 4 have a lower driving voltage, higher efficiency, and longer lifespan than those of Comparative Examples 1 and 2.

The organic light-emitting device including the condensed cyclic compound may have a low driving voltage, high efficiency and long lifespan.

It should be understood that example embodiments described herein should be considered in a descriptive sense only and not for purposes of limitation. Descriptions of features or aspects within each example embodiment should typically be considered as available for other similar features or aspects in other example embodiments.

While one or more example embodiments have been described with reference to the figures, it will be understood by those of ordinary skill in the art that various changes in form and details may be made therein without departing from the spirit and scope as defined by the following claims.

What is claimed is:

1. A compound represented by one of Formulae 1-1 to 1-4:

Formula 1-1

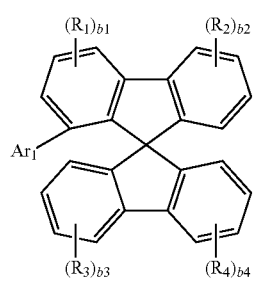

Formula 1-2

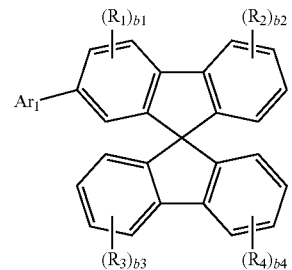

Formula 1-3

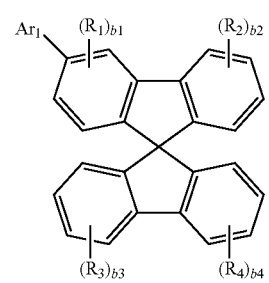

Formula 1-4

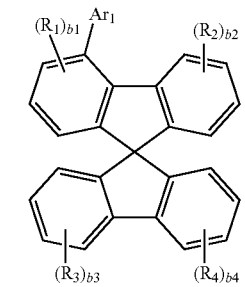

wherein $R_1$ to $R_4$ are each independently selected from hydrogen, deuterium, a $C_1$-$C_{60}$ alkyl group, a $C_1$-$C_{60}$ alkoxy group, an unsubstituted phenyl group, a $C_1$-$C_{60}$ alkyl group substituted with at least one deuterium, a $C_1$-$C_{60}$ alkoxy group substituted with at least one deuterium, and a phenyl group substituted with at least one deuterium, b1 to b4 are each independently an integer of 0 to 4, and $Ar_1$ is selected from groups represented by Formulae 2-9, 2-10, 2-14 to 2-20, 2-24 to 2-30, 2-34 to 2-40, and 2(42) to 2(54):

Formula 2-9

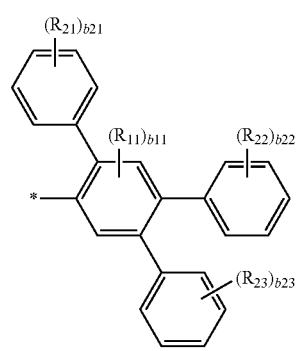

-continued
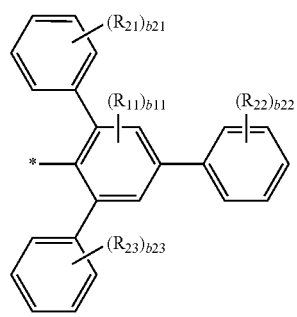
Formula 2-10
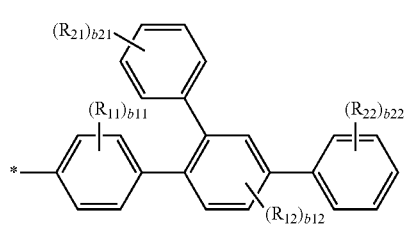
Formula 2-14
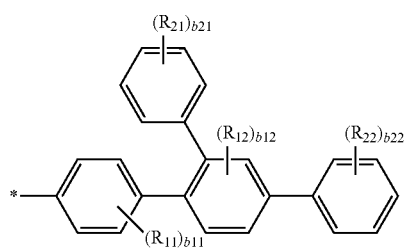
Formula 2-15
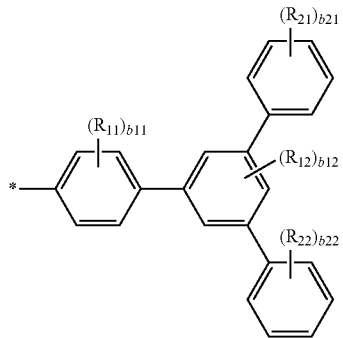
Formula 2-16
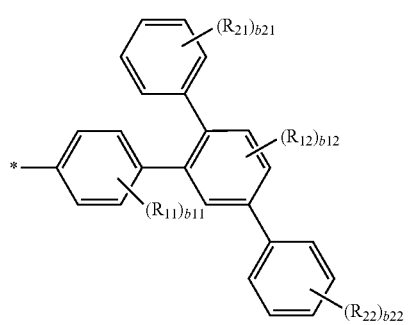
Formula 2-17
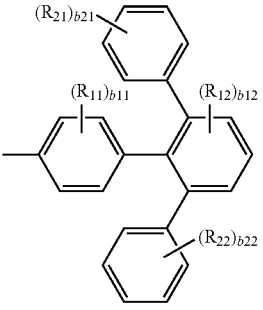
Formula 2-18
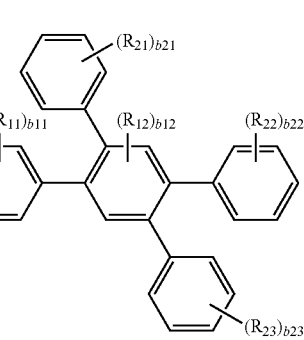
Formula 2-19
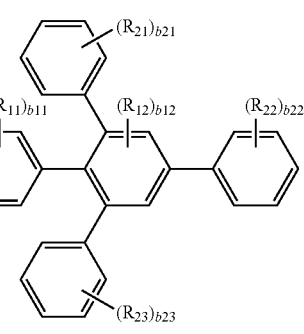
Formula 2-20
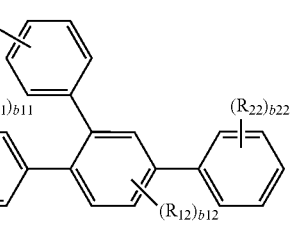
Formula 2-24
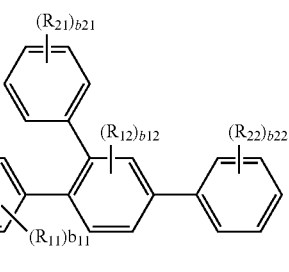
Formula 2-25

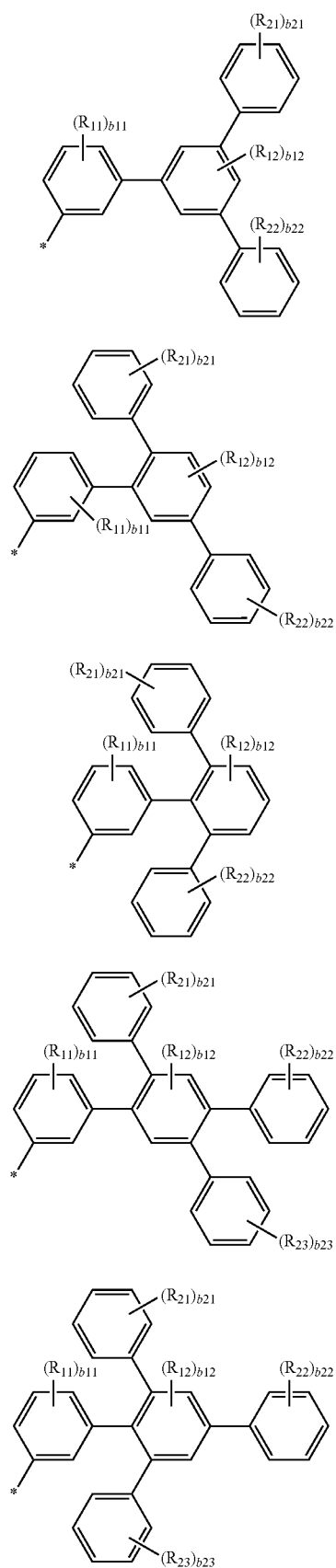
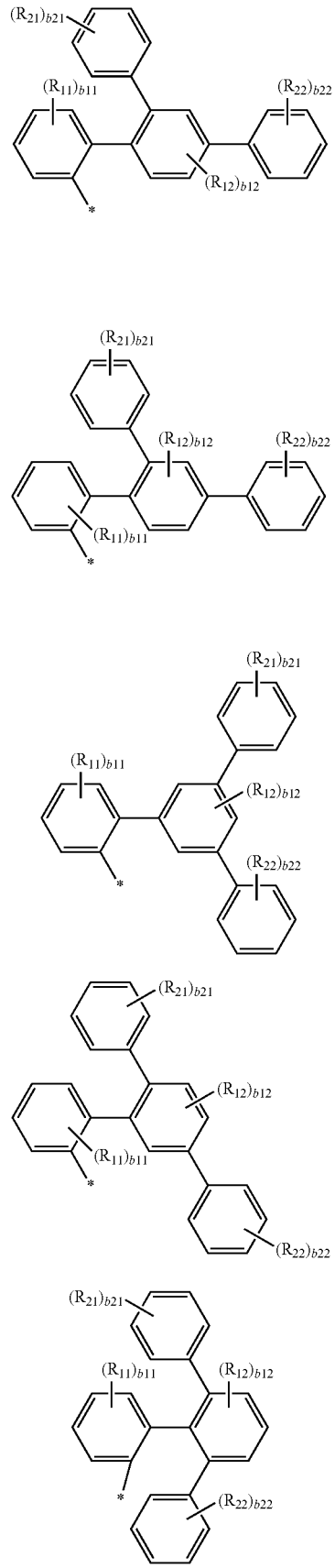

Formula 2-39
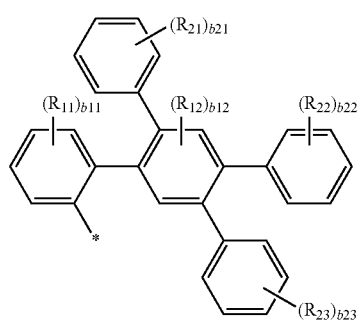
Formula 2-40
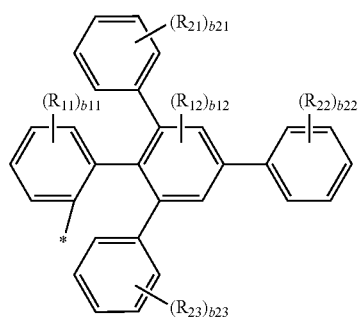
Formula 2(42)
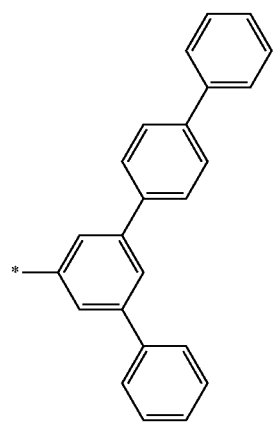
Formula 2(43)
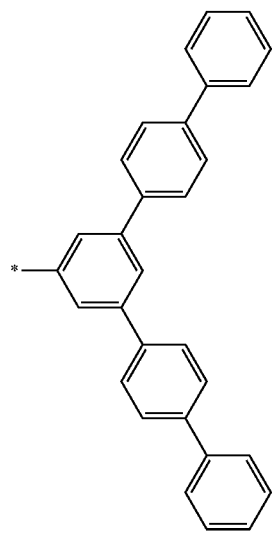
Formula 2(44)
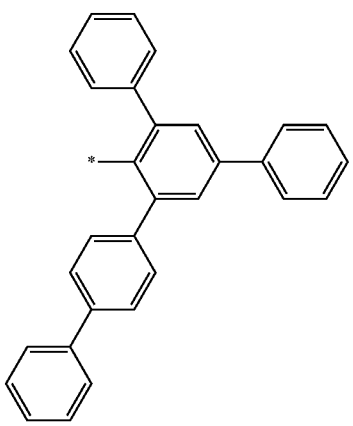
Formula 2(45)
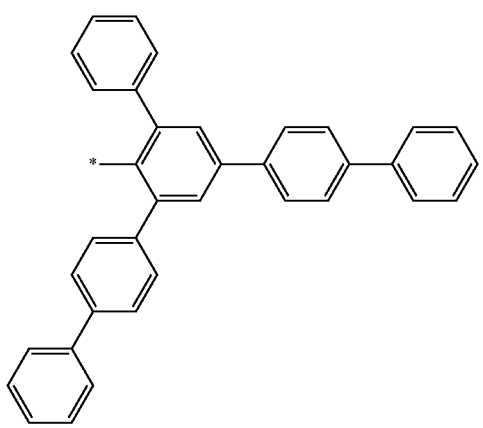

Formula 2(46)
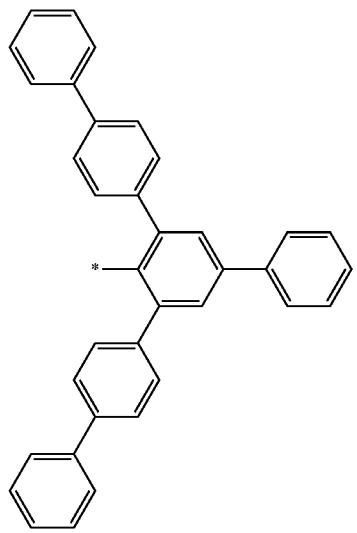
Formula 2(47)
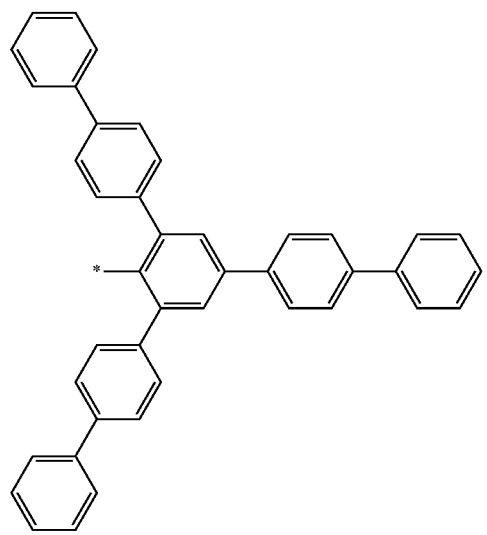
Formula 2(48)
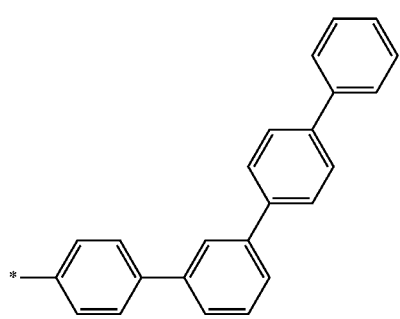
Formula 2(49)
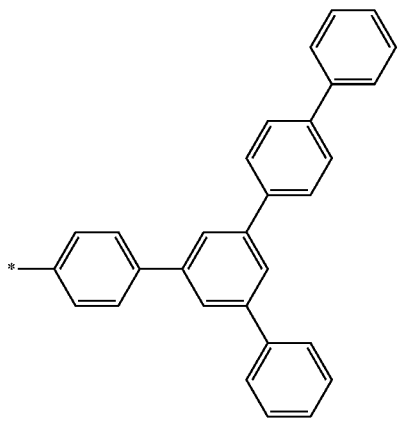
Formula 2(50)
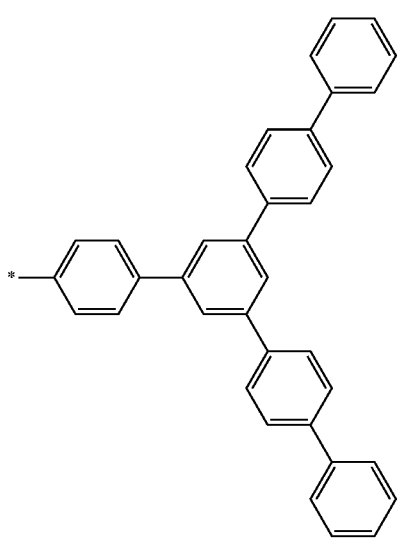
Formula 2(51)
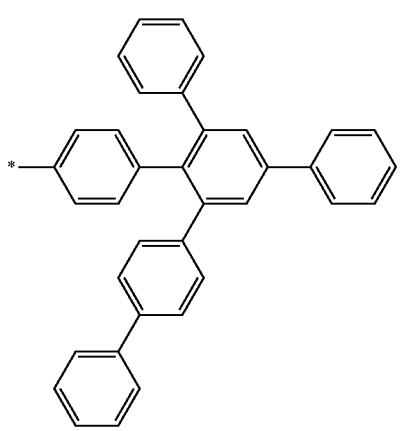

-continued

Formula 2(52)

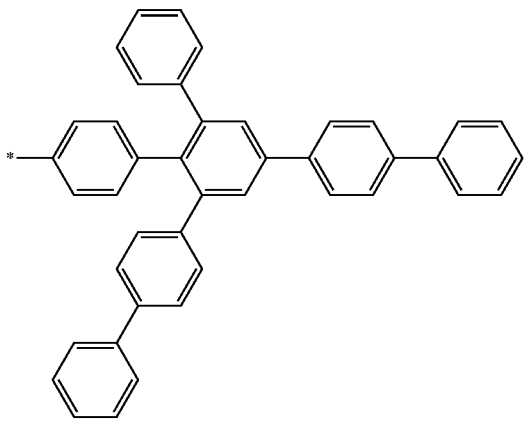

Formula 2(53)

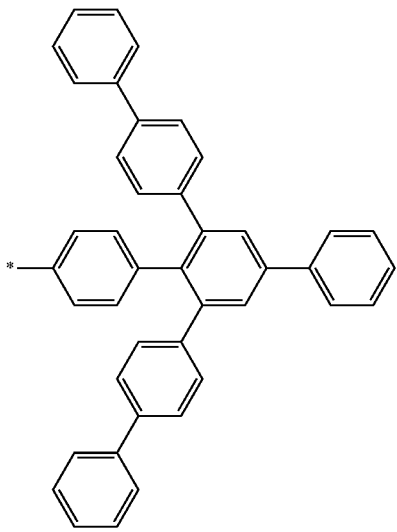

Formula 2(54)

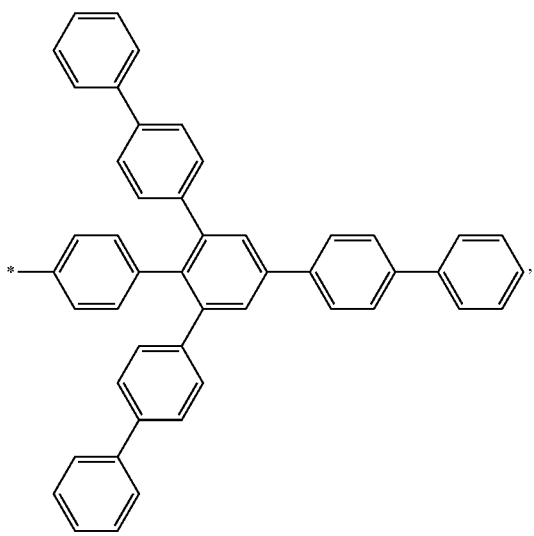

wherein in Formulae 2-9, 2-10, 2-14 to 2-20, 2-24 to 2-30, and 2-34 to 2-40, $R_{11}$, $R_{12}$, and $R_{21}$ to $R_{23}$ are each independently selected from hydrogen, deuterium, a $C_1$-$C_{60}$ alkyl group, a $C_1$-$C_{60}$ alkoxy group, an unsubstituted phenyl group, a $C_1$-$C_{60}$ alkyl group substituted with at least one deuterium, a $C_1$-$C_{60}$ alkoxy group substituted with at least one deuterium, and a phenyl group substituted with at least one deuterium;

b11, b12, and b21 to b23 are each independently 0, 1 or 2; and

* is a binding site of a neighboring atom.

2. The compound of claim 1, wherein $R_1$ to $R_4$, $R_{11}$, and $R_{21}$ are each independently selected from hydrogen, deuterium, an unsubstituted phenyl group, and a phenyl group substituted with at least one deuterium.

3. The compound of claim 1, wherein $R_1$ to $R_4$, $R_{11}$, and $R_{21}$ are each independently selected from hydrogen, —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CH DCH$_3$, —CHDCD$_2$H, —CHDCDH$_2$, —CHDCD$_3$, —CD$_2$CD$_3$, —CD$_2$CD$_2$H, and —CD$_2$CDH$_2$; an n-propyl group, an iso-propyl group, an n-butyl group, an isobutyl group, a sec-butyl group, a tert-butyl group, an n-pentyl group, an isopentyl group, a sec-pentyl group, a tert-pentyl group, a methoxy group, an ethoxy group, a propoxy group, butoxy group, a pentoxy group and an unsubstituted phenyl group, an n-propyl group substituted with at least one deuterium, an iso-propyl group substituted with at least one deuterium, an n-butyl group substituted with at least one deuterium, an isobutyl group substituted with at least one deuterium, a sec-butyl group substituted with at least one deuterium, a tert-butyl group substituted with at least one deuterium, an n-pentyl group substituted with at least one deuterium, an isopentyl group substituted with at least one deuterium, a sec-pentyl group substituted with at least one deuterium, a tert-pentyl group substituted with at least one deuterium, a methoxy group substituted with at least one deuterium, an ethoxy group substituted with at least one deuterium, a propoxy group substituted with at least one deuterium, butoxy group substituted with at least one deuterium, a pentoxy group substituted with at least one deuterium, and a phenyl group substituted with at least one deuterium.

4. The compound of claim 1, wherein $R_{11}$, $R_{12}$, and $R_{21}$ to $R_{23}$ are each independently hydrogen, deuterium, or an unsubstituted phenyl group.

5. The compound of claim 1, wherein $Ar_1$ is selected from groups represented by Formulae 2(9), 2(10), 2(14) to 2(20), 2(24) to 2(30), 2(34) to 2(40), and 2(42) to 2(54):

Formula 2(9)

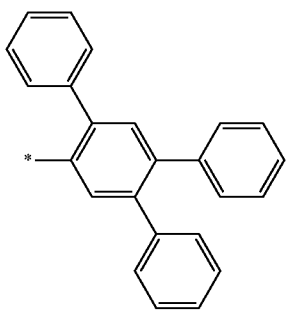

Formula 2(10)
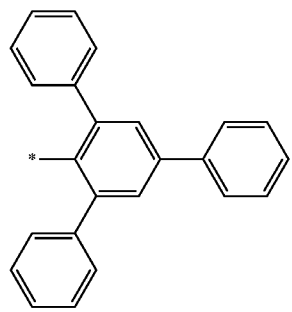
Formula 2(14)
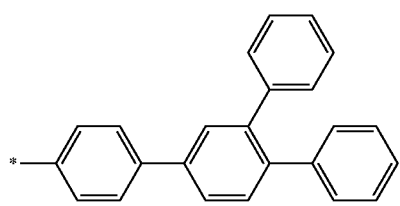
Formula 2(15)
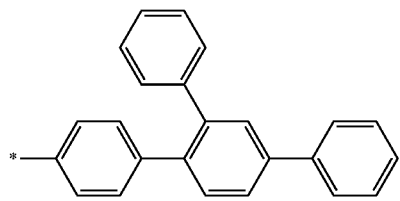
Formula (16)
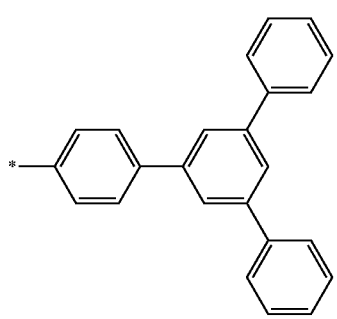
Formula 2(17)
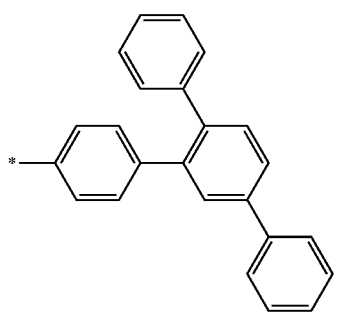
Formula 2(18)
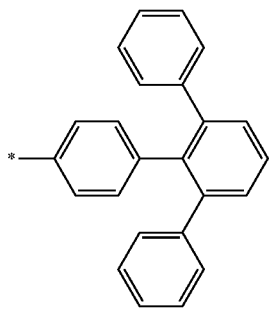
Formula 2(19)
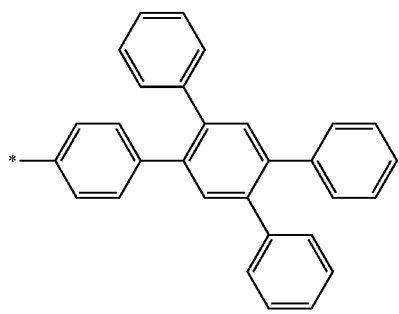
Formula 2(20)
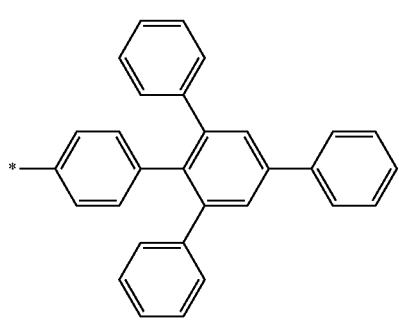
Formula 2(24)
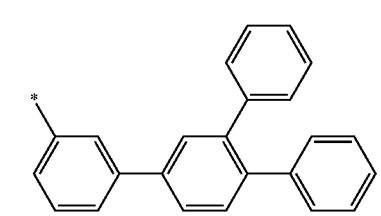
Formula 2(25)
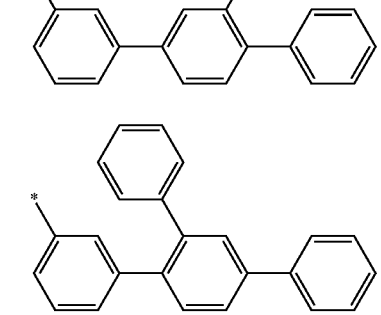

Formula 2(26)
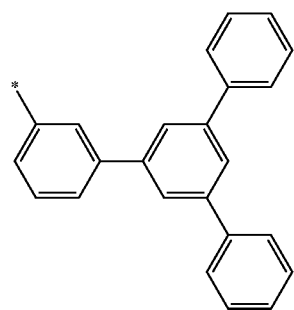
Formula 2(27)
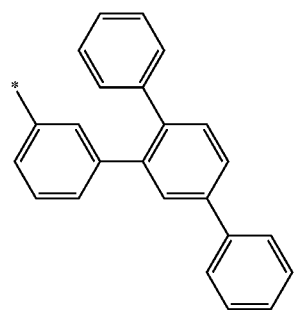
Formula 2(28)
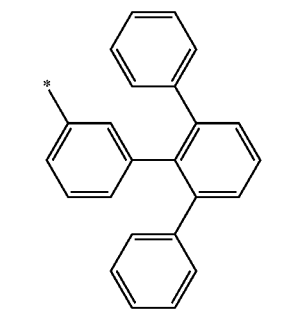
Formula 2(29)
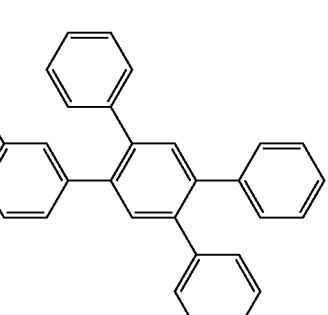
Formula 2(30)
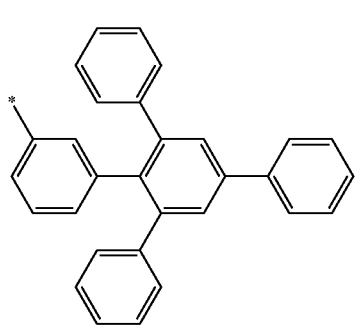
Formula 2(34)
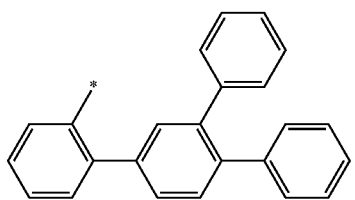
Formula 2(35)
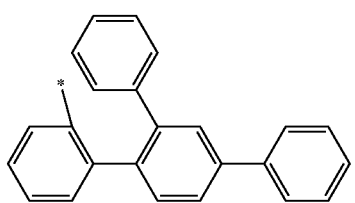
Formula 2(36)
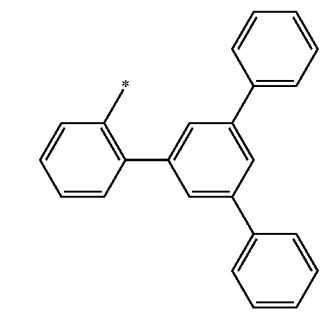
Formula 2(37)
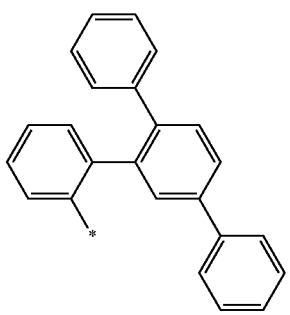
Formula 2(38)
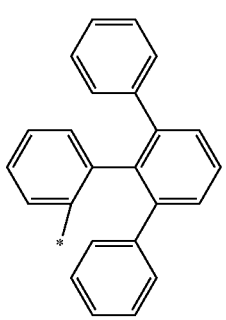

Formula 2(39)
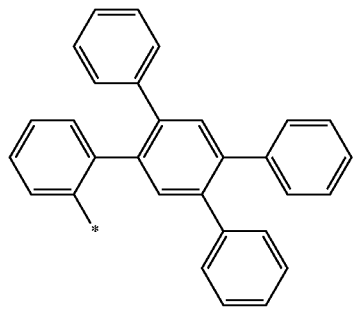
Formula 2(40)
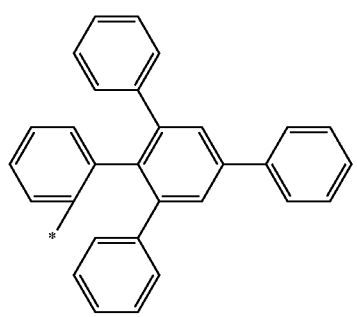
Formula 2(42)
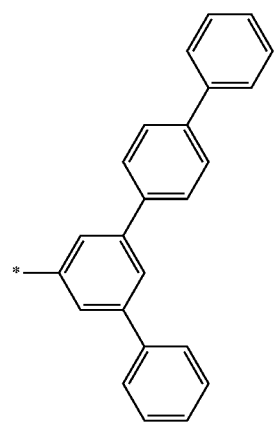
Formula 2(43)
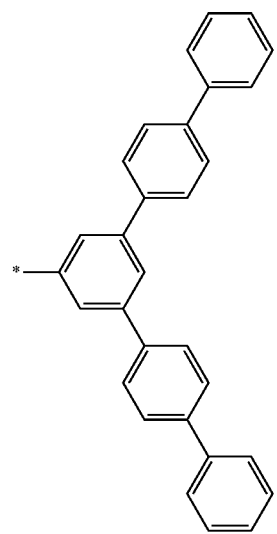
Formula 2(44)
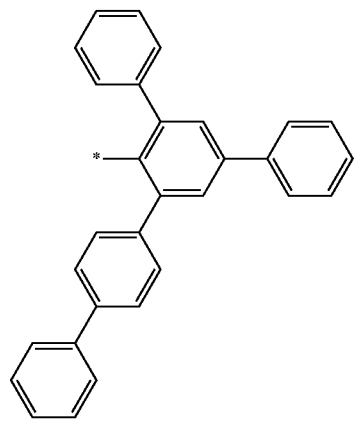
Formula 2(45)
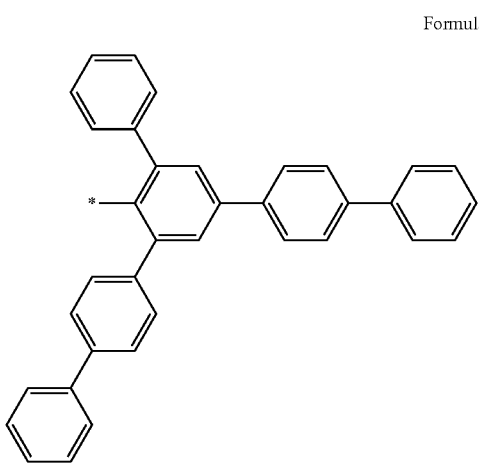
Formula 2(46)
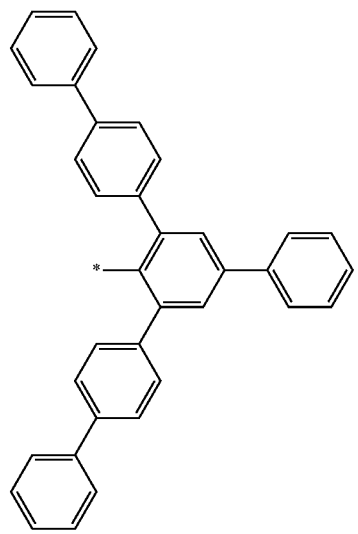

-continued
Formula 2(47)
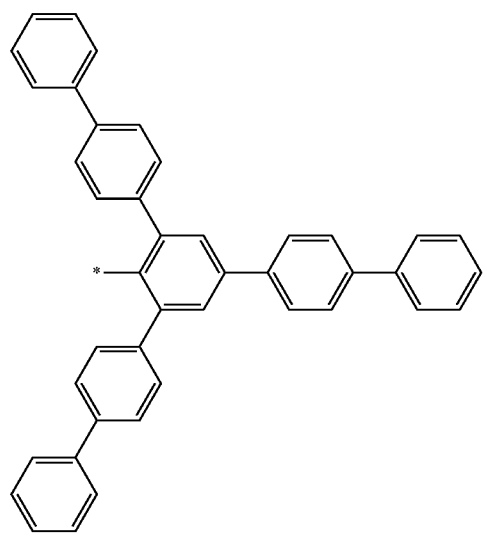
Formula 2(48)
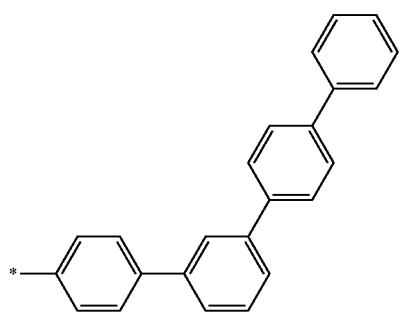
Formula 2(49)
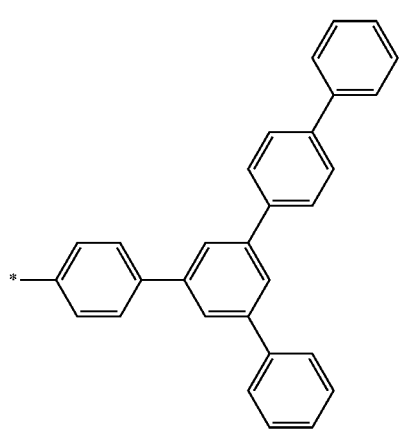
-continued
Formula 2(50)
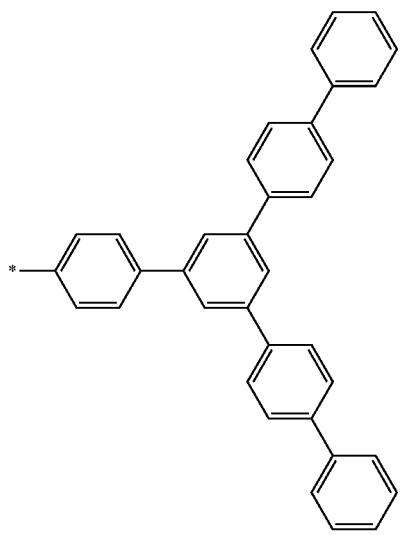
Formula 2(51)
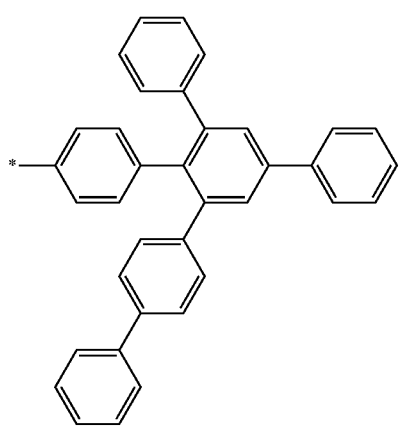
Formula 2(52)
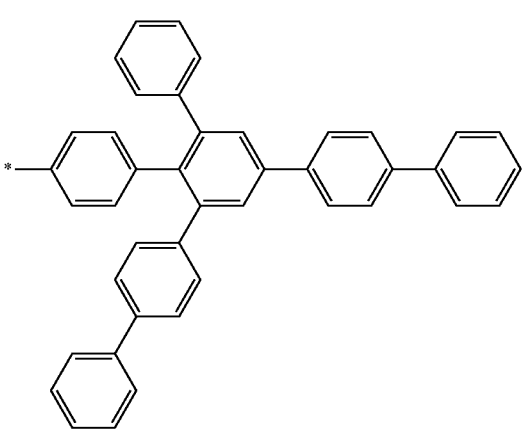

Formula 2(53)

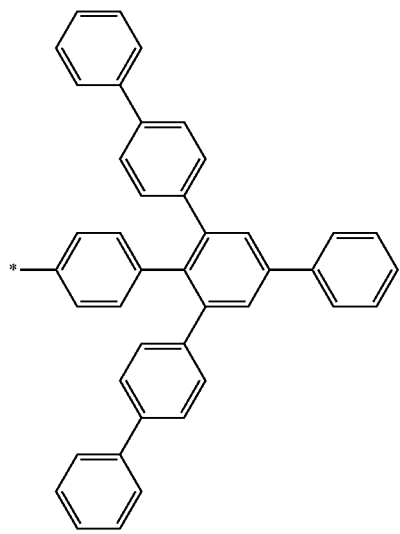

Formula 2(54)

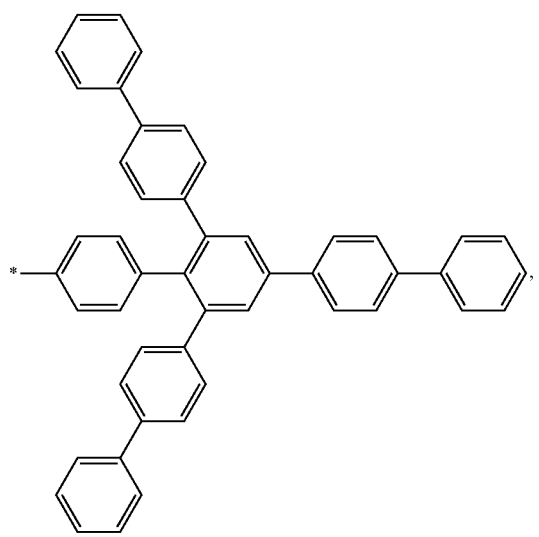

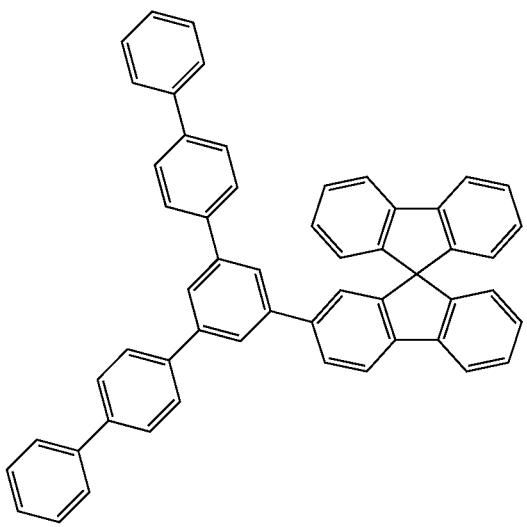

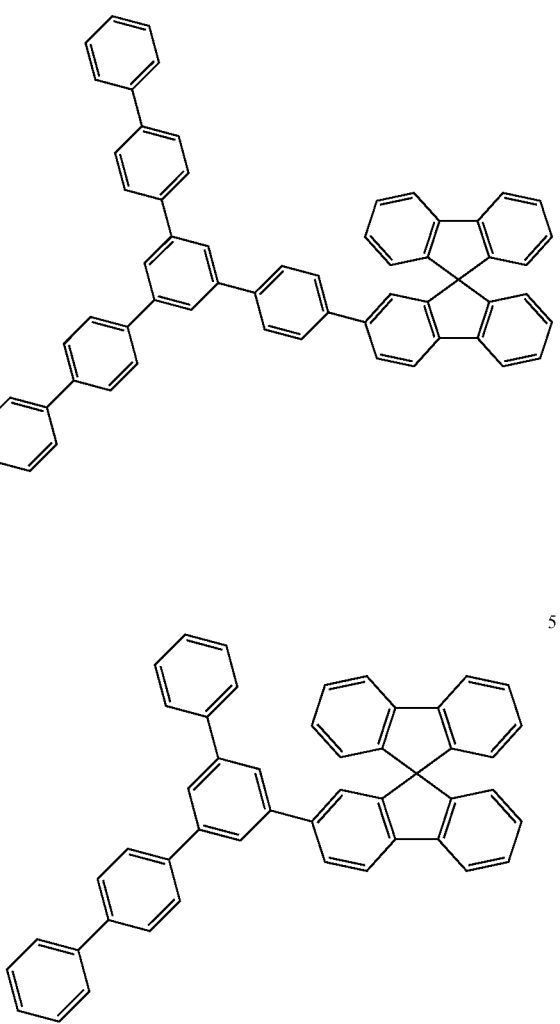

wherein * in Formulae 2(9), 2(10), 2(14) to 2(20), 2(24) to 2(30), 2(34) to 2(40), and 2(42) to 2(54) indicates a binding site to a neighboring atom.

6. The compound of claim 1, wherein the compound has a triplet ($T_1$) energy level from 2.7 eV to 3.0 eV.

7. The compound of claim 1, wherein the compound has a lowest unoccupied molecular orbital (LUMO) energy level less than −2.4 eV.

8. The compound of claim 1, wherein the compound is selected from Compounds 3 to 14:

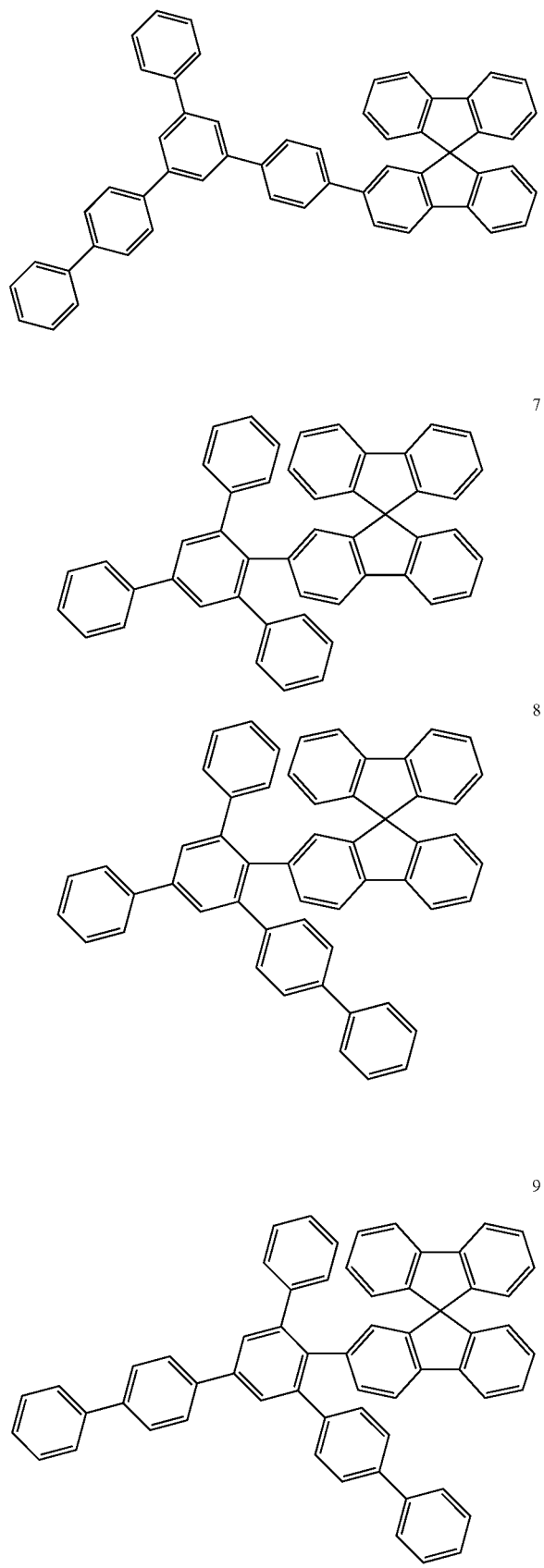
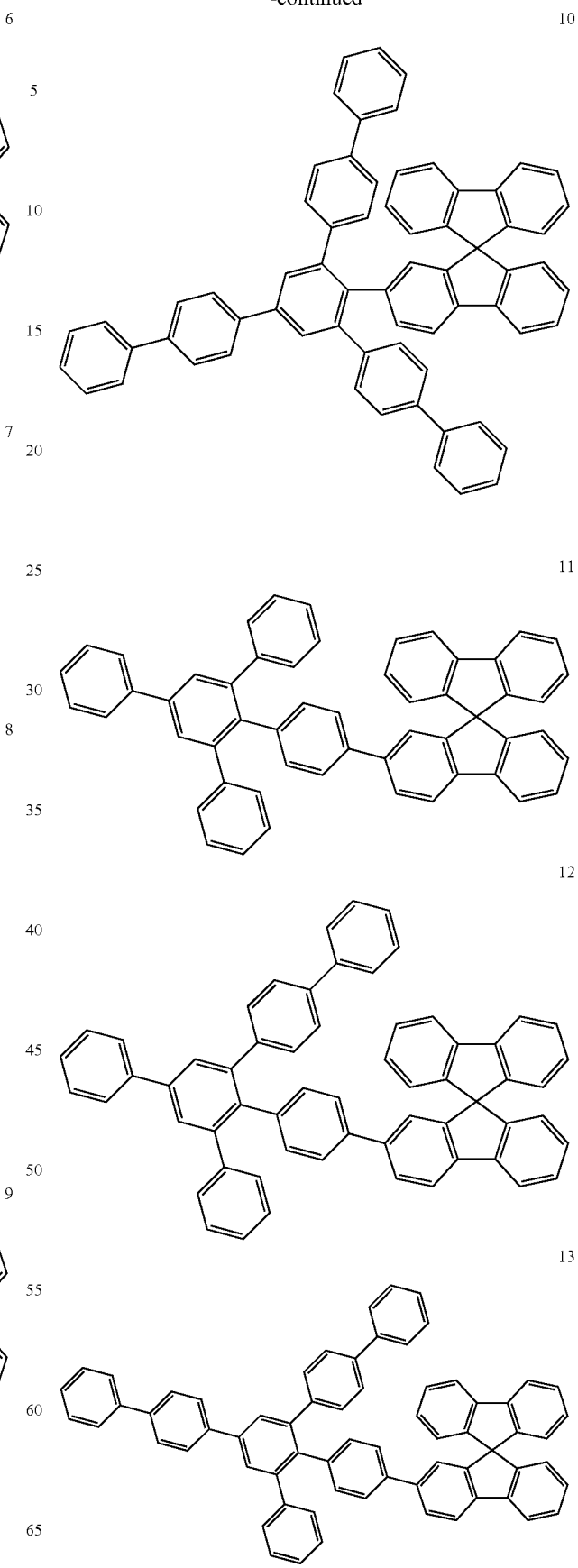

-continued

14

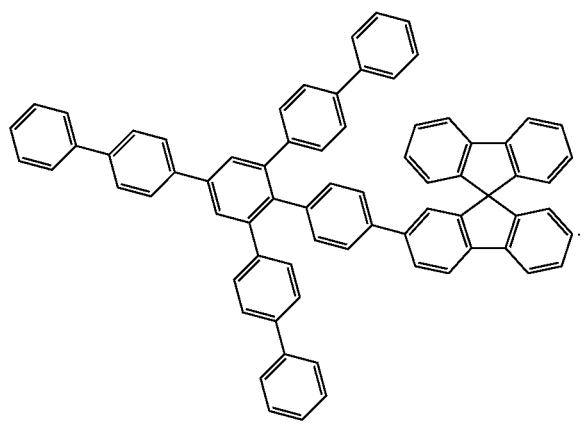

9. An organic light-emitting device comprising:
a first electrode;
a second electrode facing the first electrode; and
an organic layer between the first electrode and the second electrode, the organic layer comprising an emission layer, wherein the organic layer comprises one or more compounds represented by
one of Formulae 1-1 to 1-4:

Formula 1-1

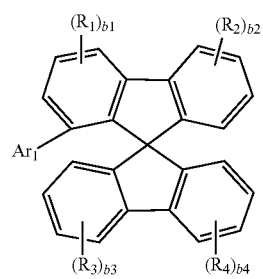

Formula 1-2

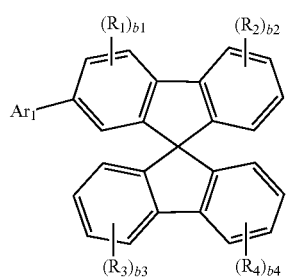

Formula 1-3

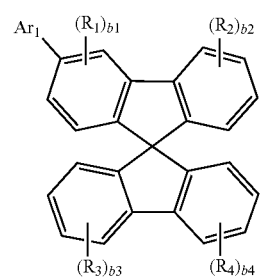

-continued

Formula 1-4

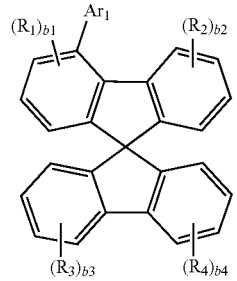

wherein $R_1$ to $R_4$ are each independently selected from hydrogen, deuterium, a $C_1$-$C_{60}$ alkyl group, a $C_1$-$C_{60}$ alkoxy group, an unsubstituted phenyl group, a $C_1$-$C_{60}$ alkyl group substituted with at least one deuterium, a $C_1$-$C_{60}$ alkoxy group substituted with at least one deuterium, and a phenyl group substituted with at least one deuterium, b1 to b4 are each independently an integer of 0 to 4, and $Ar_1$ is selected from groups represented by Formulae 2-9, 2-10, 2-14 to 2-20, 2-24 to 2-30, 2-34 to 2-40, and 2(42) to 2(54):

Formula 2-9

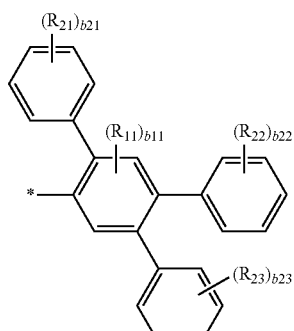

Formula 2-10

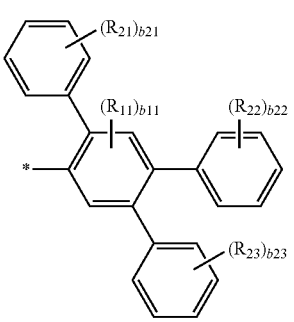

Formula 2-14

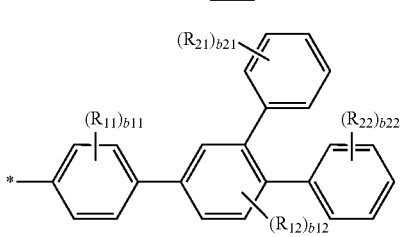

Formula 2-15
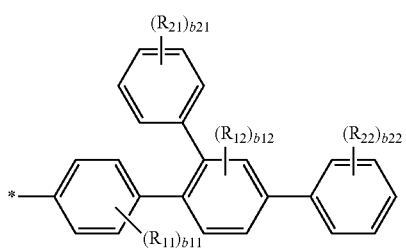
Formula 2-16
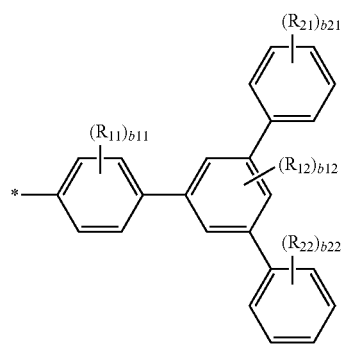
Formula 2-17
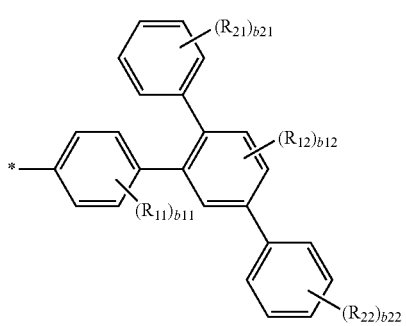
Formula 2-18
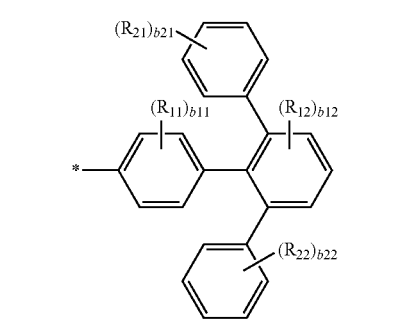
Formula 2-19
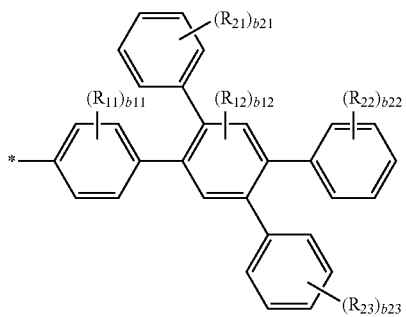
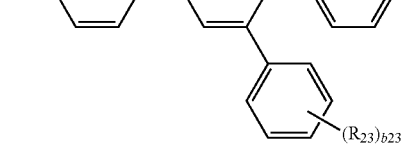
Formula 2-20
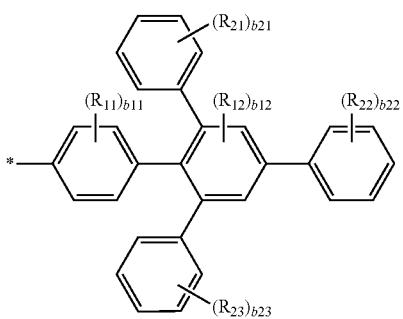
Formula 2-24
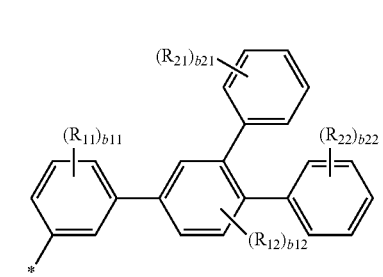
Formula 2-25
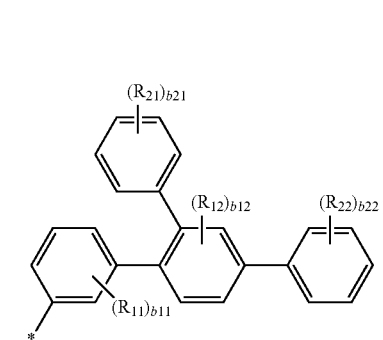
Formula 2-26
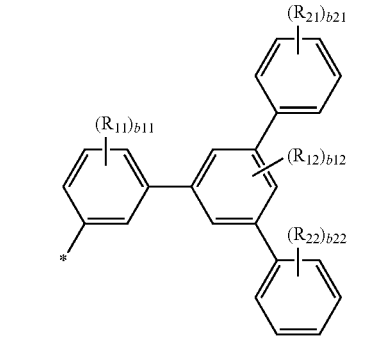
Formula 2-27
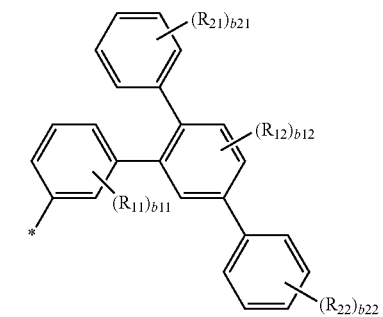

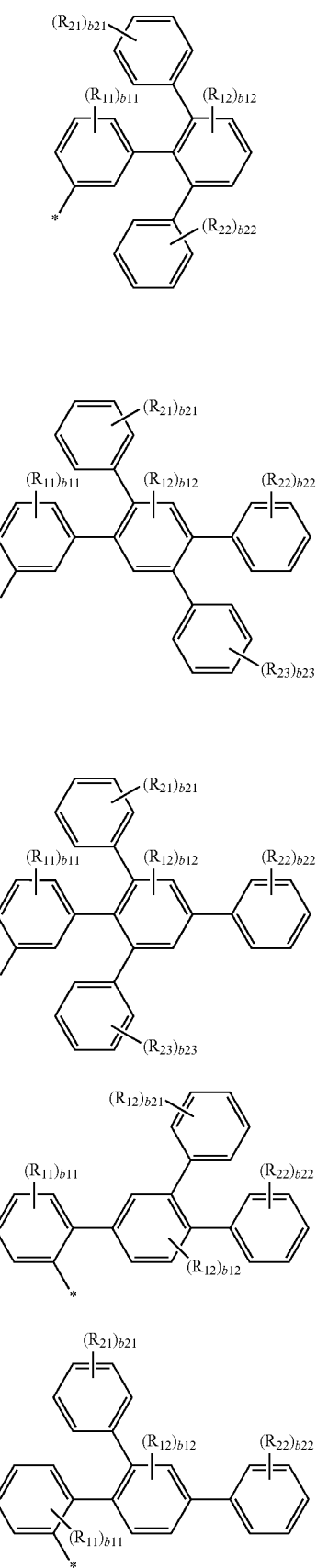
Formula 2-28
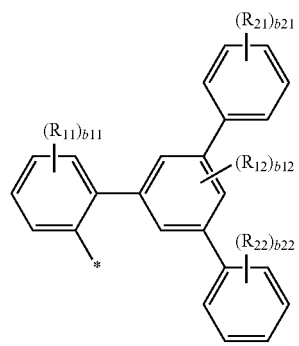
Formula 2-29
Formula 2-30
Formula 2-34
Formula 2-35
Formula 2-36
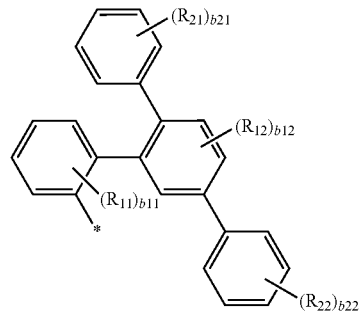
Formula 2-37
Formula 2-38
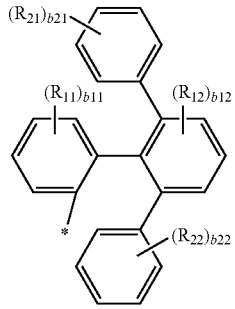
Formula 2-39
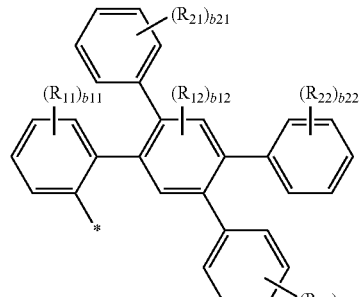
Formula 2-40
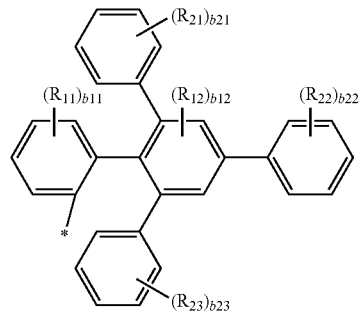

-continued
Formula 2(42)
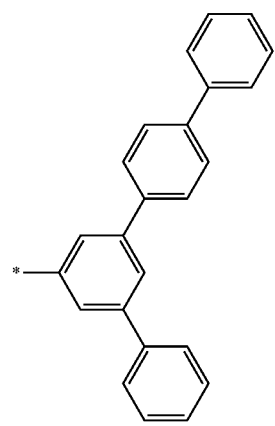
Formula 2(43)
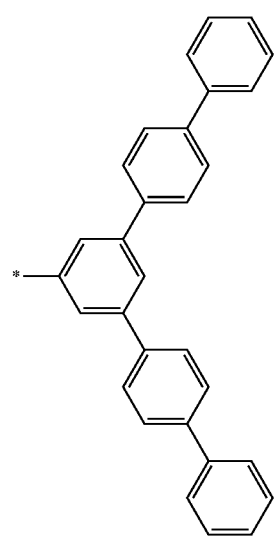
Formula 2(44)
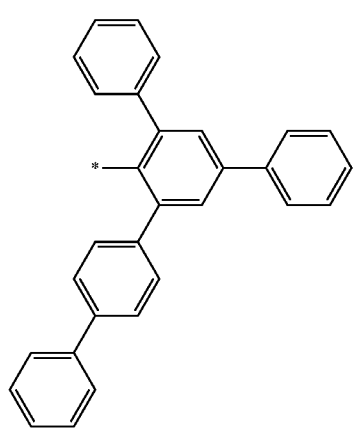
Formula 2(45)
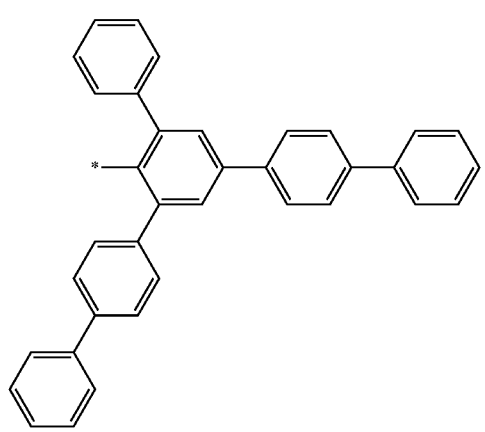
Formula 2(46)
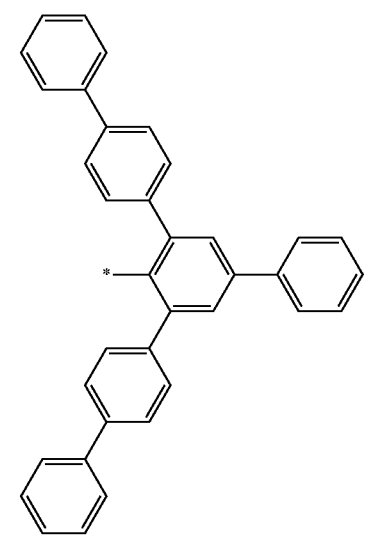
Formula2(47)
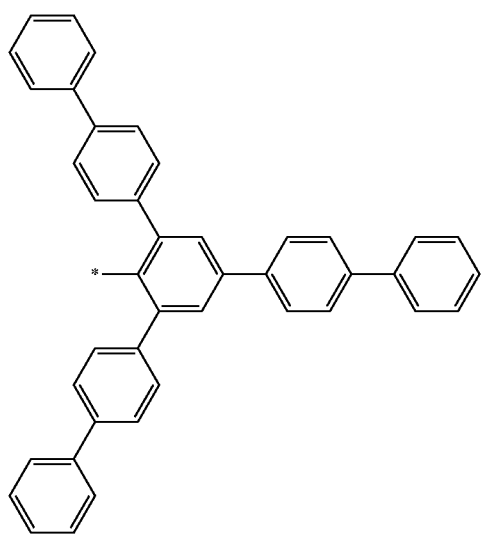

Formula 2(48)
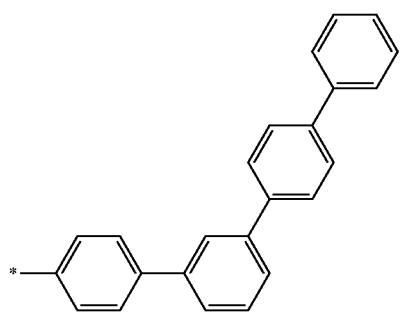
Formula 2(51)
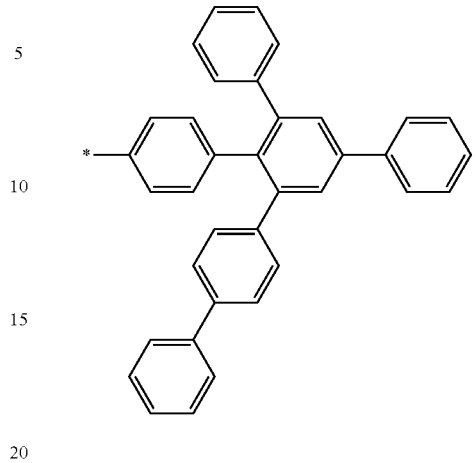
Formula 2(49)
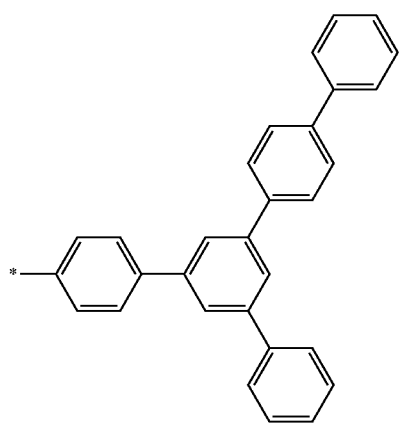
Formula 2(52)
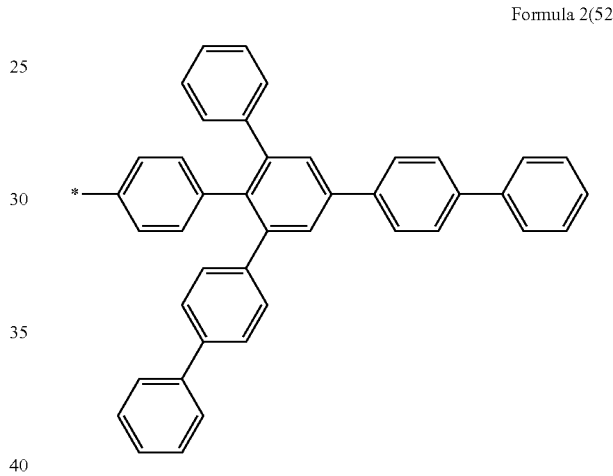
Formula 2(50)
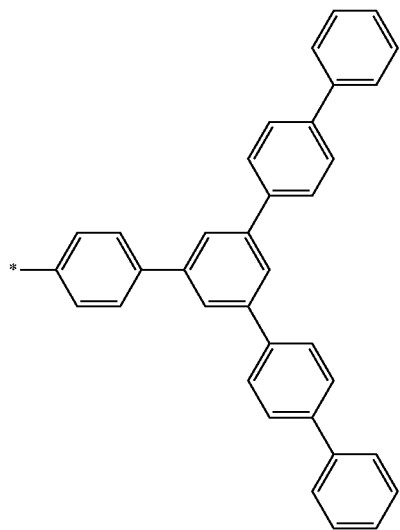
Formula 2(53)
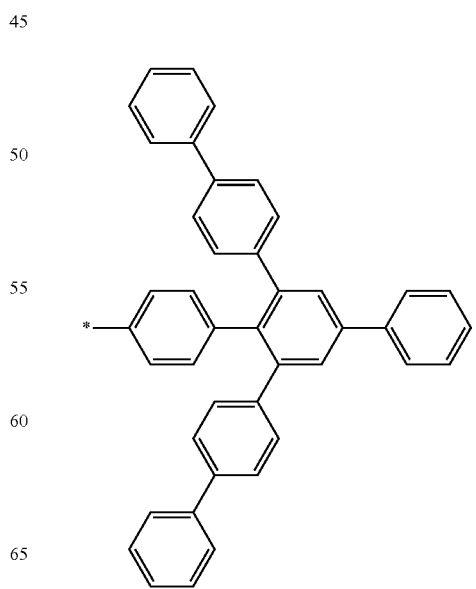

-continued

Formula 2(54)

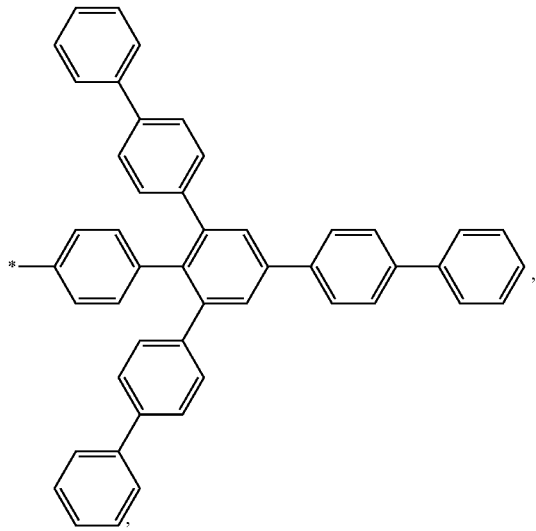

wherein in Formulae 2-9, 2-10, 2-14 to 2-20, 2-24 to 2-30, and 2-34 to 2-40, $R_{11}$, $R_{12}$, and $R_{21}$ to $R_{23}$ are each independently selected from hydrogen, deuterium, a $C_1$-$C_{60}$ alkyl group, a $C_1$-$C_{60}$ alkoxy group, an unsubstituted phenyl group, a $C_1$-$C_{60}$ alkyl group substituted with at least one deuterium, a $C_1$-$C_{60}$ alkoxy group substituted with at least one deuterium, and a phenyl group substituted with at least one deuterium;

b11, b12, and b21 to b23 are each independently 0, 1 or 2; and

* is a binding site of a neighboring atom.

10. The organic light-emitting device of claim 9, wherein the first electrode is an anode,
the second electrode is a cathode,
the organic layer further comprises a hole transport region between the first electrode and the emission layer, and an electron transport region between the emission layer and the second electrode,
the hole transport region comprises a hole injection layer, a hole transport layer, an emission auxiliary layer, an electron blocking layer, or any combination thereof, and
the electron transport region comprises a hole blocking layer, a buffer layer, an electron transport layer, an electron controlling layer, an electron injection layer, or any combination thereof.

11. The organic light-emitting device of claim 9, wherein the compound represented by Formula 1 is included in the emission layer, and the emission layer further comprises a blue phosphorescent dopant.

12. The organic light-emitting device of claim 11, wherein the triplet energy level of the compound represented by Formula 1 is larger than that of the blue phosphorescent dopant, and
a difference between the triplet energy level of the compound represented by Formula 1 and that of the blue phosphorescent dopant is less than about 0.2 eV.

13. The organic light-emitting device of claim 11, wherein the triplet energy level of the blue phosphorescent dopant is about 2.7 eV or more and about 2.9 eV or less.

14. The organic light-emitting device of claim 10, wherein the hole transport region comprises the emission auxiliary layer, and the compound represented by Formula 1 is included in the emission auxiliary layer.

15. The organic light-emitting device of claim 10, wherein the hole transport region comprises the emission auxiliary layer,
the compound represented by Formula 1 is included in each of the emission layer and the emission auxiliary layer,
the compound represented by Formula 1 included in the emission layer is the same as the compound represented by Formula 1 included in the emission auxiliary layer, and
the emission layer further comprises a blue phosphorescent dopant.

16. A compound represented by one of Formulae 1-1 to 1-4:

Formula 1-1

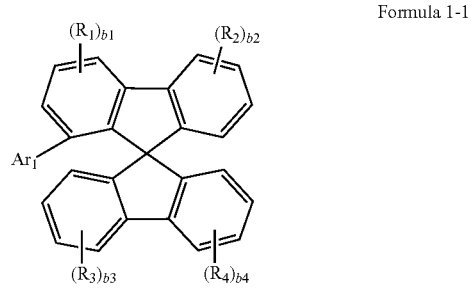

Formula 1-2

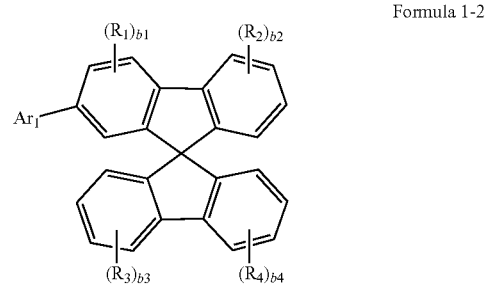

Formula 1-3

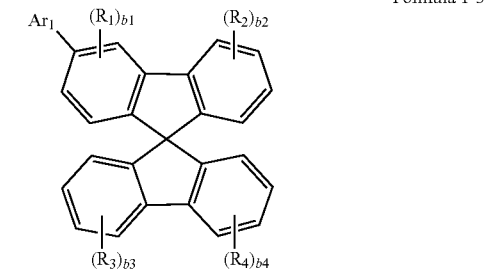

Formula 1-4

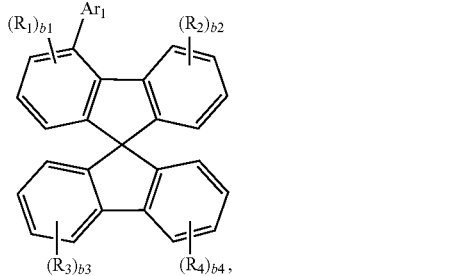

wherein $Ar_1$ is a group represented by Formula 2,

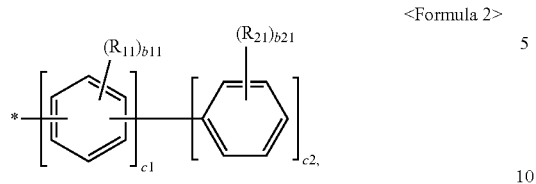

<Formula 2> wherein $R_1$ to $R_4$, $R_{11}$, and $R_{21}$ are each independently selected from hydrogen, deuterium, a $C_1$-$C_{60}$ alkyl group, a $C_1$-$C_{60}$ alkoxy group, an unsubstituted phenyl group, a $C_1$-$C_{60}$ alkyl group substituted with at least one deuterium, a $C_1$-$C_{60}$ alkoxy group substituted with at least one deuterium, and a phenyl group substituted with at least one deuterium, b1 to b4, b11, and b21 are each independently an integer of 0 to 4, c1 and c2 are each independently an integer of 1 to 5, and the sum of c1 and c2 is at least 5.

17. The compound of claim 16, wherein c1 and c2 are each independently 2 or 3.

* * * * *